(12) United States Patent
Sagehashi et al.

(10) Patent No.: US 9,086,624 B2
(45) Date of Patent: Jul. 21, 2015

(54) MONOMER, POLYMER, RESIST COMPOSITION, AND PATTERNING PROCESS

(71) Applicant: SHIN-ETSU CHEMICAL CO., LTD., Tokyo (JP)

(72) Inventors: Masayoshi Sagehashi, Joetsu (JP); Jun Hatakeyama, Joetsu (JP); Koji Hasegawa, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 13/957,175

(22) Filed: Aug. 1, 2013

(65) Prior Publication Data
US 2014/0045123 A1    Feb. 13, 2014

(30) Foreign Application Priority Data

Aug. 10, 2012 (JP) ................................. 2012-177800

(51) Int. Cl.
| | | |
|---|---|---|
| *G03F 7/004* | (2006.01) |
| *G03F 7/38* | (2006.01) |
| *C07C 69/54* | (2006.01) |
| *C07C 69/74* | (2006.01) |
| *C07C 69/75* | (2006.01) |
| *C07C 69/78* | (2006.01) |
| *C08F 220/10* | (2006.01) |
| *C08F 220/14* | (2006.01) |
| *C08F 220/16* | (2006.01) |
| *C08F 220/24* | (2006.01) |
| *C08F 222/10* | (2006.01) |
| *C08F 222/14* | (2006.01) |
| *C08F 228/02* | (2006.01) |
| *G03F 7/038* | (2006.01) |
| *C07C 57/26* | (2006.01) |
| *G03F 7/20* | (2006.01) |
| *G03F 7/039* | (2006.01) |

(52) U.S. Cl.
CPC .............. *G03F 7/0382* (2013.01); *C07C 57/26* (2013.01); *C07C 69/54* (2013.01); *C07C 69/74* (2013.01); *C07C 69/75* (2013.01); *C07C 69/78* (2013.01); *C08F 220/10* (2013.01); *C08F 220/14* (2013.01); *C08F 220/16* (2013.01); *C08F 220/24* (2013.01); *C08F 222/10* (2013.01); *C08F 222/14* (2013.01); *C08F 228/02* (2013.01); *G03F 7/038* (2013.01); *G03F 7/0397* (2013.01); *G03F 7/20* (2013.01); *G03F 7/38* (2013.01)

(58) Field of Classification Search
CPC ......... G03F 7/0382; G03F 7/38; C08F 10/00; C08F 24/00; C08F 210/00; C08F 224/00; C07C 69/54; C07C 69/608

USPC ....... 430/270.1, 325, 330, 907, 910; 526/270, 308, 243, 245, 287, 323.2, 526/326; 560/220, 183, 205

See application file for complete search history.

(56) References Cited

U.S. PATENT DOCUMENTS

| | | | |
|---|---|---|---|
| 6,136,500 A | 10/2000 | Kobayashi et al. | |
| 6,777,160 B2 | 8/2004 | Sato et al. | |
| 7,537,880 B2 | 5/2009 | Harada et al. | |
| 7,759,047 B2 | 7/2010 | Hatakeyama et al. | |
| 7,771,913 B2 | 8/2010 | Kaneko et al. | |
| 8,017,298 B2 * | 9/2011 | Tsubaki ................... 430/270.1 |
| 8,034,547 B2 | 10/2011 | Tsubaki et al. | |
| 8,071,272 B2 | 12/2011 | Tsubaki | |
| 8,227,183 B2 | 7/2012 | Tsubaki et al. | |
| 8,323,872 B2 | 12/2012 | Hatakeyama et al. | |
| 2008/0090172 A1 | 4/2008 | Hatakeyama et al. | |
| 2008/0153030 A1 | 6/2008 | Kobayashi et al. | |
| 2011/0177462 A1 | 7/2011 | Hatakeyama et al. | |
| 2012/0148945 A1 | 6/2012 | Hasegawa et al. | |
| 2014/0030654 A1 * | 1/2014 | Masuyama et al. ........ 430/281.1 |

FOREIGN PATENT DOCUMENTS

| | | |
|---|---|---|
| JP | 2002-314539 A | 11/2002 |
| JP | 3790649 B2 | 6/2006 |
| JP | 2007-025634 A | 2/2007 |
| JP | 3991462 B2 | 10/2007 |
| JP | 2007-297590 A | 11/2007 |
| JP | 2007-316448 A | 12/2007 |
| JP | 2008-003569 A | 1/2008 |
| JP | 2008-111103 A | 5/2008 |
| JP | 2008-122932 A | 5/2008 |
| JP | 2008-158339 A | 7/2008 |
| JP | 2008-281974 A | 11/2008 |
| JP | 2008-281975 A | 11/2008 |
| JP | 2008-281980 A | 11/2008 |

(Continued)

OTHER PUBLICATIONS

V. Truffert et al., "Ultimate contact hole resolution using immersion lithography with line/space imaging", Proc. of SPIE, vol. 7274, 2009, pp. 7274on1-12.

D.C. Owe-Yang et al., "Double exposure for the contact layer of the 65-nm node", Proc. of SPIE, vol. 5753, 2005, pp. 171-180.

(Continued)

*Primary Examiner* — John Chu

(74) *Attorney, Agent, or Firm* — Westerman, Hattori, Daniels & Adrian, LLP

(57) ABSTRACT

A polymer comprising recurring units derived from a (meth) acrylate monomer of tertiary ester type having branched alkyl on alicycle is used to form a resist composition. When subjected to exposure, PEB and organic solvent development, the resist composition is improved in dissolution contrast.

12 Claims, 1 Drawing Sheet

(56) References Cited

FOREIGN PATENT DOCUMENTS

| | | |
|---|---|---|
| JP | 2008-309879 A | 12/2008 |
| JP | 4554665 B2 | 9/2010 |
| JP | 4590431 B2 | 12/2010 |
| JP | 2011-170316 A | 9/2011 |

OTHER PUBLICATIONS

H. Nakamura et al., "Contact Hole Formation by Multiple Exposure Technique in Ultra-low k1 Lithography", Proc of SPIE, vol. 5377, 2004, pp. 255-263.

S. Nakao et al. "0.12μm Hole Pattern Formation by KrF Lithography for Giga Bit DRAM", IEEE IEDM Tech, pp. 61-64.

* cited by examiner

MONOMER, POLYMER, RESIST COMPOSITION, AND PATTERNING PROCESS

CROSS REFERENCE TO RELATED APPLICATIONS

This non-provisional application claims priority under 35 U.S.C. §119(a) on Patent Application No. 2012-177800 filed in Japan on Aug. 10, 2012, the entire contents of which are hereby incorporated by reference.

TECHNICAL FIELD

This invention relates to a monomer useful as a starting reactant for functional, pharmaceutical and agricultural chemicals, a polymer comprising recurring units derived from the monomer, a photoresist composition comprising the polymer, and a pattern forming process using the photoresist composition. The monomer is useful for the preparation of a polymer that finds use as a base resin in a resist composition which is processed by steps of exposure of resist film, deprotection reaction with the aid of acid and heat, and development with an organic solvent to form a negative tone pattern in which the unexposed region is dissolved and the exposed region is not dissolved.

BACKGROUND ART

In the recent drive for higher integration and operating speeds in LSI devices, the pattern rule is made drastically finer. The photolithography which is currently on widespread use in the art is approaching the essential limit of resolution determined by the wavelength of a light source. As the light source used in the lithography for resist pattern formation, g-line (436 nm) or i-line (365 nm) from a mercury lamp was widely used in 1980's. Reducing the wavelength of exposure light was believed effective as the means for further reducing the feature size. For the mass production process of 64 MB dynamic random access memories (DRAM, processing feature size 0.25 μm or less) in 1990's and later ones, the exposure light source of i-line (365 nm) was replaced by a KrF excimer laser having a shorter wavelength of 248 nm. However, for the fabrication of DRAM with a degree of integration of 256 MB and 1 GB or more requiring a finer patterning technology (processing feature size 0.2 μm or less), a shorter wavelength light source was required. Over a decade, photolithography using ArF excimer laser light (193 nm) has been under active investigation. It was expected at the initial that the ArF lithography would be applied to the fabrication of 180-nm node devices. However, the KrF excimer lithography survived to the mass-scale fabrication of 130-nm node devices. So, the full application of ArF lithography started from the 90-nm node. The ArF lithography combined with a lens having an increased numerical aperture (NA) of 0.9 is considered to comply with 65-nm node devices. For the next 45-nm node devices which required an advancement to reduce the wavelength of exposure light, the $F_2$ lithography of 157 nm wavelength became a candidate. However, for the reasons that the projection lens uses a large amount of expensive $CaF_2$ single crystal, the scanner thus becomes expensive, hard pellicles are introduced due to the extremely low durability of soft pellicles, the optical system must be accordingly altered, and the etch resistance of resist is low; the development of $F_2$ lithography was stopped and instead, the ArF immersion lithography was introduced.

In the ArF immersion lithography, the space between the projection lens and the wafer is filled with water having a refractive index of 1.44. The partial fill system is compliant with high-speed scanning and when combined with a lens having a NA of 1.3, enables mass production of 45-nm node devices.

One candidate for the 32-nm node lithography is lithography using extreme ultraviolet (EUV) radiation with wavelength 13.5 nm. The EUV lithography has many accumulative problems to be overcome, including increased laser output, increased sensitivity, increased resolution and minimized edge roughness (LER, LWR) of resist film, defect-free MoSi laminate mask, reduced aberration of reflection mirror, and the like.

Another candidate for the 32-nm node lithography is high refractive index liquid immersion lithography. The development of this technology was stopped because LUAG, a high refractive index lens candidate had a low transmittance and the refractive index of liquid did not reach the goal of 1.8.

The process that now draws attention under the above-discussed circumstances is a double patterning process involving a first set of exposure and development to form a first pattern and a second set of exposure and development to form a pattern between the first pattern features. A number of double patterning processes are proposed. One exemplary process involves a first set of exposure and development to form a photoresist pattern having lines and spaces at intervals of 1:3, processing the underlying layer of hard mask by dry etching, applying another layer of hard mask thereon, a second set of exposure and development of a photoresist film to form a line pattern in the spaces of the first exposure, and processing the hard mask by dry etching, thereby forming a line-and-space pattern at a half pitch of the first pattern. An alternative process involves a first set of exposure and development to form a photoresist pattern having spaces and lines at intervals of 1:3, processing the underlying layer of hard mask by dry etching, applying a photoresist layer thereon, a second set of exposure and development to form a second space pattern on the remaining hard mask portion, and processing the hard mask by dry etching. In either process, the hard mask is processed by two dry etchings.

As compared with the line pattern, the hole pattern is difficult to reduce the feature size. In order for the prior art method to form fine holes, an attempt is made to form fine holes by under-exposure of a positive resist film combined with a hole pattern mask. This, however, results in the exposure margin being extremely narrowed. It is then proposed to form holes of greater size, followed by thermal flow or RELACS® method to shrink the holes as developed. However, there is a problem that control accuracy becomes lower as the pattern size after development and the size after shrinkage differ greater and the quantity of shrinkage is greater. With the hole shrinking method, the hole size can be shrunk, but the pitch cannot be narrowed.

It is then proposed in Non-Patent Document 1 that a pattern of X-direction lines is formed in a positive resist film using dipole illumination, the resist pattern is cured, another resist material is coated thereon, and a pattern of Y-direction lines is formed in the other resist film using dipole illumination, leaving a grid line pattern, spaces of which provide a hole pattern. Although a hole pattern can be formed at a wide margin by combining X and Y lines and using dipole illumination featuring a high contrast, it is difficult to etch vertically staged line patterns at a high dimensional accuracy. It is proposed in Non-Patent Document 2 to form a hole pattern by exposure of a negative resist film through a Levenson phase shift mask of X-direction lines combined with a Levenson phase shift mask of Y-direction lines. However, the crosslinking negative resist film has the drawback that the resolving power is low as compared with the positive resist film, because the maximum resolution of ultrafine holes is determined by the bridge margin.

A hole pattern resulting from a combination of two-exposures of X- and Y-direction lines and subsequent image reversal into a negative pattern can be formed using a high-contrast line pattern of light. Thus holes having a narrow pitch and fine size can be opened as compared with the prior art.

Non-Patent Document 3 reports three methods for forming hole patterns via image reversal. The three methods are: method (1) involving subjecting a positive resist composition to two double-dipole exposures of X and Y lines to form a dot pattern, depositing a $SiO_2$ film thereon by LPCVD, and effecting $O_2$-RIE for reversal of dots into holes; method (2) involving forming a dot pattern by the same steps as in (1), but using a resist composition designed to turn alkali-soluble and solvent-insoluble upon heating, coating a phenol-base overcoat film thereon, effecting alkaline development for image reversal to form a hole pattern; and method (3) involving double dipole exposure of a positive resist composition and organic solvent development for image reversal to form holes.

The organic solvent development to form a negative pattern is a traditional technique. A resist composition comprising cyclized rubber is developed using an alkene such as xylene as the developer. An early chemically amplified resist composition comprising poly(tert-butoxycarbonyloxystyrene) is developed with anisole as the developer to form a negative pattern.

Recently a highlight is put on the organic solvent development again. It would be desirable if a very fine hole pattern, which is not achievable with the positive tone, is resolvable through negative tone exposure. To this end, a positive resist composition featuring a high resolution is subjected to organic solvent development to form a negative pattern. An attempt to double a resolution by combining two developments, alkaline development and organic solvent development is under study.

As the ArF resist composition for negative tone development with organic solvent, positive ArF resist compositions of the prior art design may be used. Such pattern forming processes are described in Patent Documents 1 to 3. These patent documents disclose resist compositions for organic solvent development comprising a copolymer of hydroxyadamantane methacrylate, a copolymer of norbornane lactone methacrylate, and a copolymer of methacrylate having acidic groups including carboxyl, sulfo, phenol and thiol groups substituted with two or more acid labile groups, and pattern forming processes using the same.

Further, Patent Document 4 discloses a process for forming a pattern through organic solvent development in which a protective film is applied onto a resist film. Patent Document 5 discloses a topcoatless process for forming a pattern through organic solvent development in which an additive is added to a resist composition so that the additive may segregate at the resist film surface after spin coating to provide the surface with improved water repellency.

The positive development system involving deprotection reaction to generate a carboxyl group and subsequent neutralization reaction with aqueous alkaline developer to improve a dissolution rate achieves a high dissolution contrast in that the dissolution rate differs between the unexposed and exposed regions by a factor of more than 1,000. In contrast, the negative development system via organic solvent development provides a low contrast because the dissolution rate in the unexposed region due to solvation is low, and the dissolution rate thus differs between the unexposed and exposed regions by a factor of less than 100. For the negative development system via organic solvent development, it is desired to seek for a novel material which can offer a high dissolution contrast. Patent Document 6 describes an acid labile group of tertiary ester type having isopropyl directly attached to cyclohexyl ring. Although this example is to be applied to a positive resist composition compatible with alkaline developer, this acid labile group has never been used in positive resists because the branched alkyl group directly attached to ring undergoes swell in the developer, with an increased propensity that the pattern collapses and bridges form between pattern features after development.

CITATION LIST

Patent Document 1: JP-A 2008-281974
Patent Document 2: JP-A 2008-281975
Patent Document 3: JP 4554665
Patent Document 4: JP 4590431
Patent Document 5: JP-A 2008-309879
Patent Document 6: JP-A 2002-341539
Non-Patent Document 1: Proc. SPIE Vol. 5377, p. 255 (2004)
Non-Patent Document 2: IEEE IEDM Tech. Digest 61 (1996)
Non-Patent Document 3: Proc. SPIE Vol. 7274, p. 72740N (2009)

DISCLOSURE OF INVENTION

The organic solvent development is low in dissolution contrast, as compared with the positive resist system adapted to be dissolved in alkaline developer when deprotection reaction takes place to produce acidic carboxyl or phenol groups. Specifically, in the case of alkaline developer, the alkali dissolution rate differs more than 1,000 times between unexposed and exposed regions, whereas the difference in the case of organic solvent development is at most 100 times, and only about 10 times for certain materials. No sufficient margin is available. In the case of aqueous alkaline development, the dissolution rate is improved by neutralization reaction with carboxyl groups. In the case of organic solvent development with no accompanying reaction, the dissolution rate is low because dissolution is solely due to solvation. It is necessary not only to improve the dissolution rate of the unexposed region, but also to reduce the dissolution rate of the exposed region that is a remaining portion of resist film. If the dissolution rate of the exposed region is high, the thickness of the remaining film is so reduced that the underlying substrate may not be processed by etching through the pattern as developed. Further it is important to enhance the gradient or gamma (γ) at the dose corresponding to dissolution/non-dissolution conversion. A low γ value is prone to form an inversely tapered profile and allows for pattern collapse in the case of a line pattern. To obtain a perpendicular pattern, the resist must have a dissolution contrast having a γ value as high as possible.

While prior art photoresist compositions of the alkaline aqueous solution development type are described in Patent Documents 1 to 3, they have a low dissolution contrast upon organic solvent development. It would be desirable to have a novel material having a significant difference in dissolution rate between the exposed and unexposed regions and capable of achieving a high dissolution contrast (γ) upon organic solvent development.

When an attempt is made to form a hole pattern through negative development, regions surrounding the holes receive light so that excess acid is generated therein. Since the holes are not opened if the acid diffuses inside the holes, control of acid diffusion is also important.

An object of the invention is to provide a negative pattern-forming resist composition which has a significant dissolution contrast and a high sensitivity upon organic solvent development. Another object is to provide a pattern forming process capable of forming a hole or trench pattern via positive/negative reversal by organic solvent development.

The inventors have found that a polymer comprising recurring units derived from a (meth)acrylate monomer of tertiary ester type having a substituent group of branched structure on alicycle is effective as a base resin and that a resist composition comprising the polymer, which is processed by exposure, PEB and organic solvent development, is improved in dissolution contrast upon organic solvent development.

Accordingly, in a first aspect, the invention provides a monomer having the general formula (1):

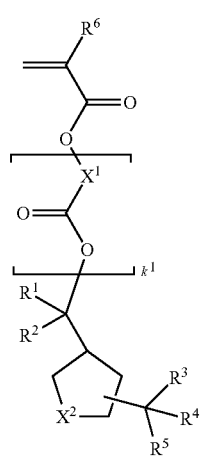

(1)

wherein $R^1$ and $R^2$ are each independently straight, branched or cyclic $C_1$-$C_{10}$ alkyl, $R^1$ and $R^2$ may bond together to form a ring with the carbon atom to which they are attached, $R^3$, $R^4$ and $R^5$ are each independently hydrogen, methyl or ethyl, excluding that at least two of $R^3$, $R^4$ and $R^5$ are hydrogen at the same time, $R^6$ is hydrogen or methyl, $X^1$ is a $C_1$-$C_{10}$ alkylene group which may have an ether radical, ester radical, lactone ring or hydroxyl radical, or $C_6$-$C_{10}$ arylene group, $X^2$ is methylene or ethylene, and $k^1$ is 0 or 1.

In a second aspect, the invention provides a polymer comprising recurring units having the general formula (A1):

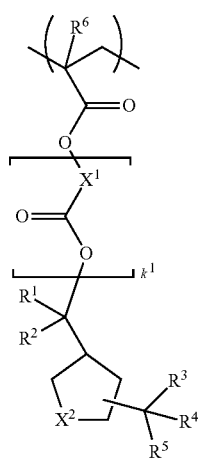

(A1)

wherein $R^1$ to $R^6$, $X^1$, $X^2$, and $k^1$ are as defined above.

In a third aspect, the invention provides a pattern forming process comprising the steps of applying a resist composition comprising the polymer of the second aspect and an optional acid generator onto a substrate, prebaking the composition to form a resist film, exposing a selected region of the resist film to high-energy radiation, baking, and developing the exposed film in an organic solvent-based developer to form a negative pattern wherein the unexposed region of resist film is dissolved away and the exposed region of resist film is not dissolved.

Typically, the developer comprises at least one organic solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the step of exposing the resist film to high-energy radiation includes KrF excimer laser lithography of wavelength 248 nm, ArF excimer laser lithography of wavelength 193 nm, EUV lithography of wavelength 13.5 nm or EB lithography.

In another embodiment, the pattern forming process is defined as comprising the steps of applying a resist composition onto a substrate, the resist composition comprising the polymer defined above, an optional acid generator, and an organic solvent, prebaking the composition to form a resist film, forming a protective film on the resist film, exposing a selected region of the resist film to high-energy radiation, baking, and applying an organic solvent-based developer to dissolve away the protective film and the unexposed region of resist film for forming a negative pattern wherein the exposed region of resist film is not dissolved.

In a fourth aspect, the invention provides a negative pattern-forming resist composition comprising a polymer, an acid generator, and an organic solvent wherein the polymer comprising recurring units having formula (A1) defined above is dissolvable in a developer selected from the same list as above.

ADVANTAGEOUS EFFECTS OF INVENTION

When an acid labile group having branched alkyl as mentioned above is applied to a positive resist film adapted for alkaline development, the resist swells in the developer due to high lipophilicity of branched alkyl group, giving rise to problems of pattern collapse and pattern feature bridging. When the acid labile group is applied to negative pattern formation via organic solvent development, a high dissolution contrast is available because developer solubility is improved by the branched alkyl group. Since the resist does not swell in the organic solvent developer, neither pattern collapse nor bridging occurs.

BRIEF DESCRIPTION OF DRAWINGS

The only FIGURE, FIG. 1 is a cross-sectional view of a patterning process according one embodiment of the invention.

DESCRIPTION OF EMBODIMENTS

Figure 1A:
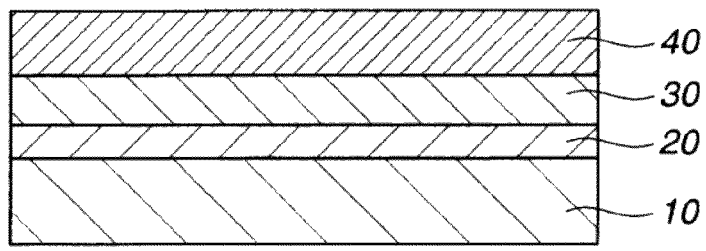
FIG. 1A shows a photoresist film disposed on a substrate.

The terms "a" and "an" herein do not denote a limitation of quantity, but rather denote the presence of at least one of the referenced item. "Optional" or "optionally" means that the subsequently described event or circumstances may or may not occur, and that description includes instances where the event, or circumstance occurs and instances where it does not. As used herein, the notation ($C_n$-$C_m$) means a group containing from n to m carbon atoms per group. As used herein, the term "film" is used interchangeably with "coating" or "layer." The term "processable layer" is interchangeable with patternable layer and refers to a layer that can be processed such as by etching to form a pattern therein. The term "(meth)acrylate" refers collectively to acrylate and methacrylate.

The abbreviations and acronyms have the following meaning.

Mw: weight average molecular weight
Mn: number average molecular weight
Mw/Mn: molecular weight distribution or dispersity
GPC: gel permeation chromatography
PEB: post-exposure bake
PAG: photoacid generator Briefly stated, the invention pertains to a resist composition comprising a polymer comprising recurring units derived from a (meth)acrylate monomer of tertiary ester type having a substituent group of branched structure on alicycle, an optional acid generator, and an organic solvent; and a pattern forming process comprising the steps of applying the resist composition onto a substrate, prebaking to remove the unnecessary solvent and form a resist film, exposing a selected region of the resist film to high-energy radiation, PEB, and developing the exposed film in an organic solvent-based developer to form a negative pattern.

For the purpose of enhancing the dissolution rate of the unexposed region during organic solvent development, it is effective to introduce an acid labile group having alkyl group of branched structure. Solvation takes place in the branched portion, accelerating the dissolution rate. On the other hand, an acid labile group having cyclic structure is effective for suppressing acid diffusion.

When a tertiary ester type acid labile group having a branched substituent group (e.g., isopropyl, tert-butyl or tert-amyl) on alicycle is incorporated, the solvent solubility is improved over the tertiary ester type acid labile group free of a branched substituent group. On the other hand, the cyclic structure is effective for suppressing acid diffusion. A negative pattern featuring low diffusion and a high contrast can be formed via organic solvent development.

The first, embodiment is a monomer having a branched substituent group on alicycle, represented by the general formula (1).

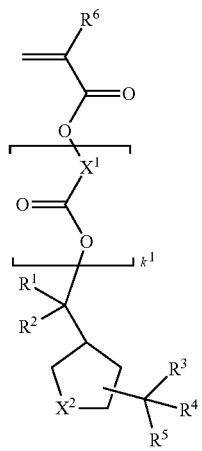

(1)

Herein $R^1$ and $R^2$ are each independently a straight, branched or cyclic $C_1$-$C_{10}$ alkyl group, $R^1$ and $R^2$ may bond together to form a ring with the carbon atom to which they are attached. $R^3$, $R^4$ and $R^5$ are each independently hydrogen, methyl or ethyl. It is excluded that at least two of $R^3$, $R^4$ and $R^5$ are hydrogen at the same time. $R^6$ is hydrogen or methyl. $X^1$ is a $C_1$-$C_{10}$ alkylene group which may have an ether radical, ester radical, lactone ring or hydroxyl radical, or a $C_6$-$C_{10}$ arylene group, $X^2$ is methylene or ethylene, and $k^1$ is 0 or 1.

In formula (1), $X^1$ is a $C_1$-$C_{10}$ alkylene group which may have an ether radical, ester radical, lactone ring or hydroxyl radical, or a $C_6$-$C_{10}$ arylene group, examples of which are shown below.

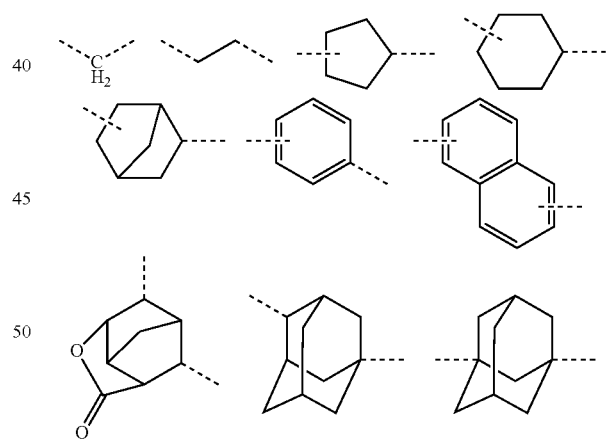

(The broken line denotes a valence bond.)

In formula (1), $X^2$ is methylene or ethylene, indicating that the monomer of formula (1) has a cyclopentane or cyclohexane ring as the alicyclic group. For the purpose of enhancing the dissolution rate of unexposed region on organic solvent development, a more carbon count in the alicycle, combined with the inclusion of a branched substituent group, provides a higher dissolution rate in organic solvent. It is thus preferred that $X^2$ be ethylene, that is, the alicycle in the monomer be a cyclohexane ring.

Examples of the monomer having formula (1) are shown below, but not limited thereto.
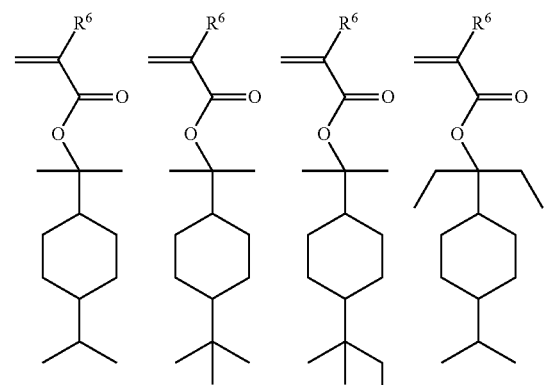
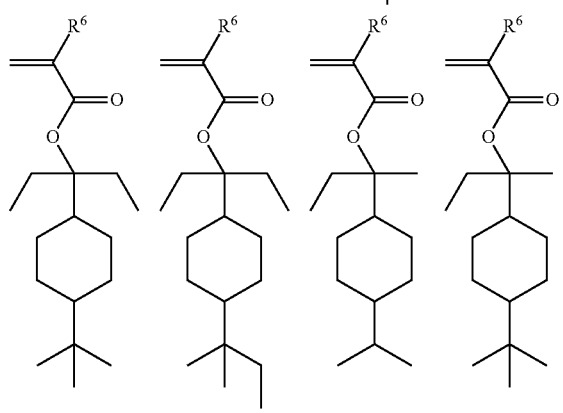
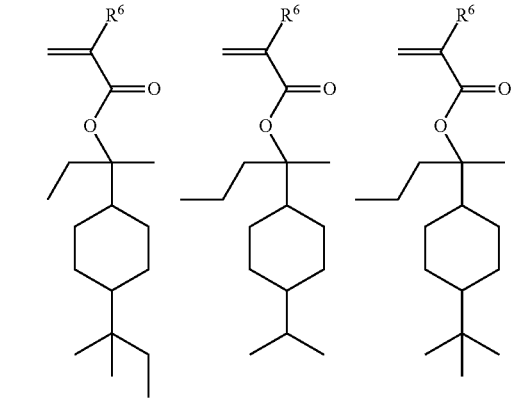
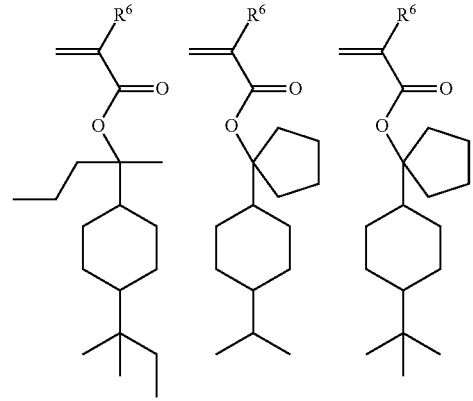
-continued
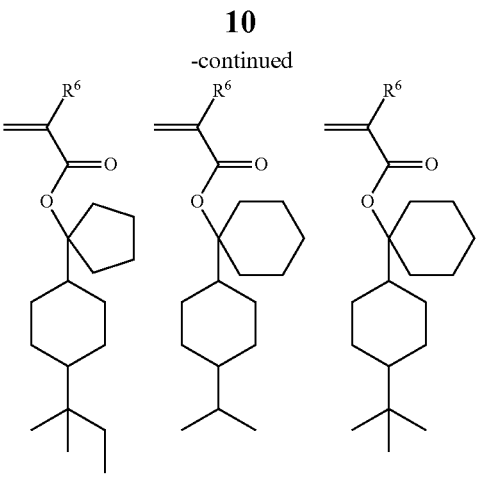
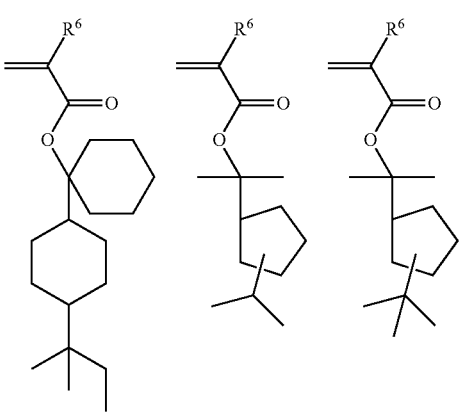
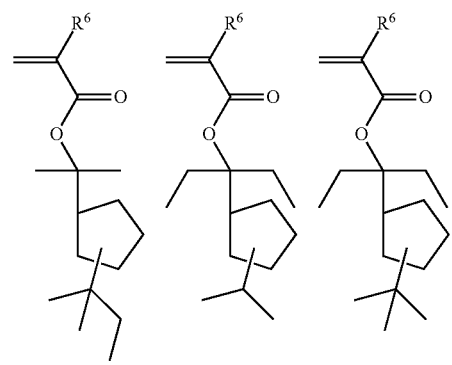
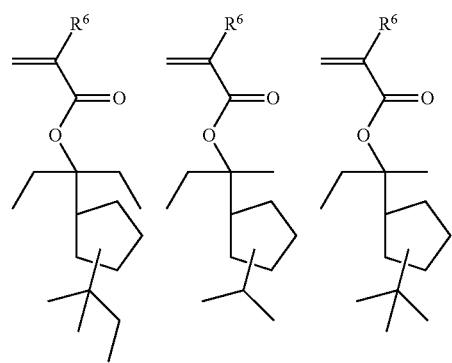

-continued
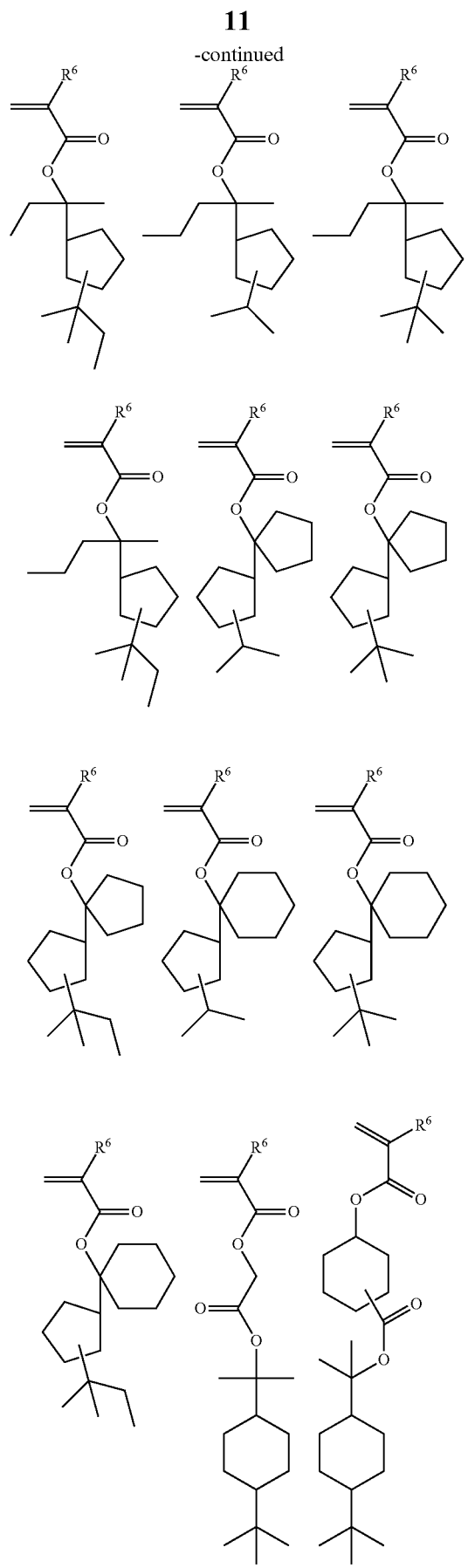
-continued
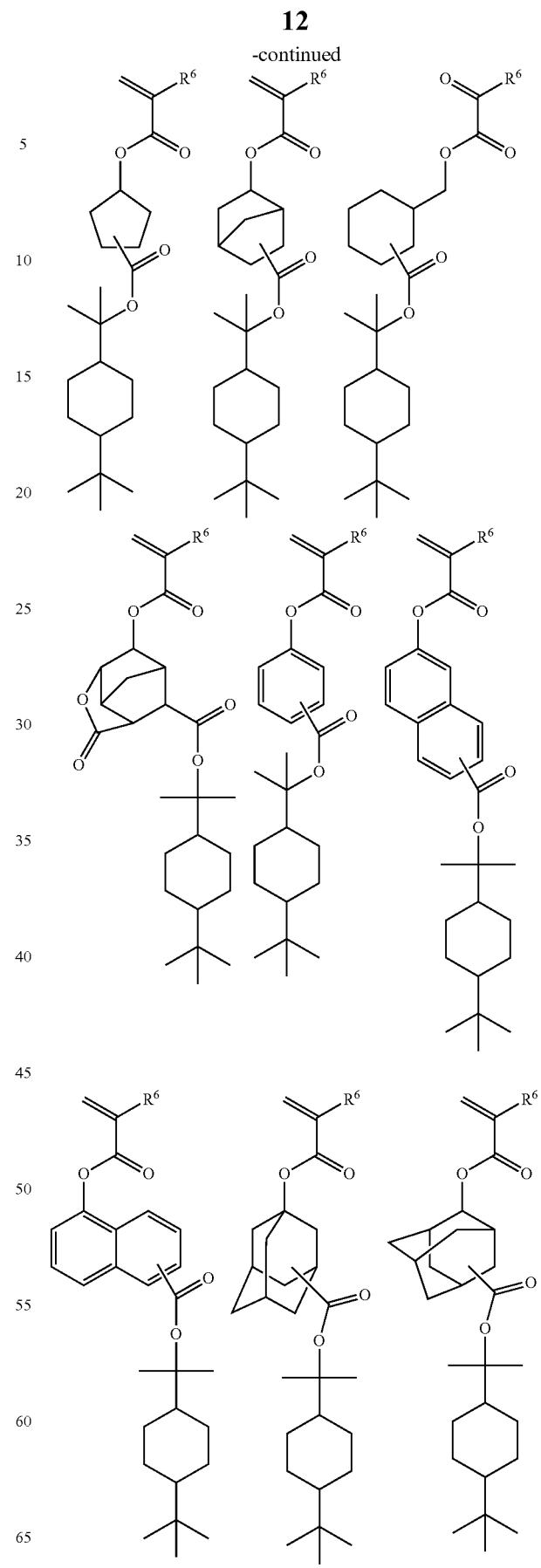

Notably, $R^6$ is as defined above.

The monomer having formula (1) may be prepared by any well-known methods. One exemplary scheme is shown below, although the preparation method is not limited thereto.

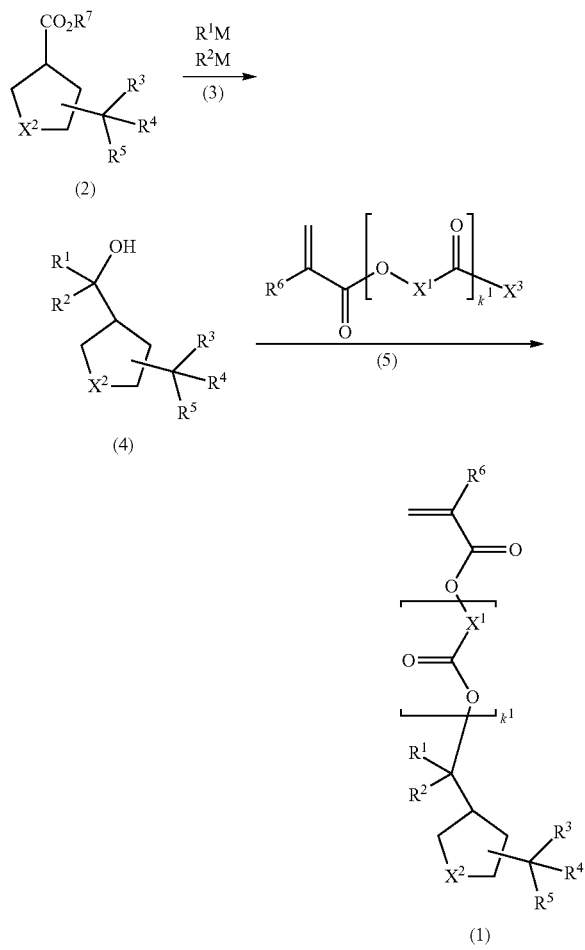

Herein $R^1$ to $R^6$, $X^1$, $X^2$ and $k^1$ are as defined above, $R^7$ is $C_1$-$C_5$ alkyl, $X^3$ is a halogen atom, hydroxyl or acyloxy group, M is optionally substituted Li, Na, K, MgHal or ZnHal, and Hal is a halogen atom.

The method for synthesizing the monomer according to the illustrated reaction scheme is described in detail.

Step i) starts with ester (2) and carries out addition reaction with alkyl metal reagent (3) to form tertiary alcohol (4). The reaction may be carried out by the standard technique. For example, once ester (2) is dissolved in an ether solvent (e.g., tetrahydrofuran or diethyl ether), alkyl metal reagent (3) corresponding to substituents $R^1$ and $R^2$ such as a Grignard reagent (e.g., methylmagnesium chloride or ethylmagnesium chloride) or alkyl lithium reagent (e.g., methyllithium) is added thereto, yielding tertiary alcohol (4). The reaction system may be cooled or heated as desired. Typically the reaction is conducted at a temperature of 0° C. to near the boiling point of the solvent. The reaction time is determined as appropriate by monitoring the reaction process by gas chromatography (GC) or silica gel thin layer chromatography (TLC) because it is desirable from the yield aspect to drive the reaction to completion. Usually the reaction time is about 0.5 to about 24 hours. The tertiary alcohol (4) may be recovered from the reaction mixture by ordinary aqueous work-up. If necessary, it may be purified by standard techniques like distillation, chromatography and recrystallization.

Step ii) is a reaction of tertiary alcohol (4) with esterifying agent (5) to form the desired monomer (1). The reaction of step ii) may readily proceed in a well-known manner. Suitable esterifying agents (5) include acid chlorides of formula (5) wherein $X^3$ is chlorine, carboxylic acids of formula (5) wherein $X^3$ is hydroxyl, and acid anhydrides of formula (5) wherein $X^3$ is acyloxy. In one embodiment wherein the esterifying agent (5) used is an acid chloride such as methacryloyl chloride, the tertiary alcohol (4), the acid chloride, and a base (e.g., triethylamine, pyridine or 4-dimethylaminopyridine) may be successively or simultaneously added to a solventless system or to a solvent (e.g., methylene chloride, acetonitrile, toluene or hexane) while the reaction system may be cooled or heated as desired. In another embodiment wherein the esterifying agent (5) used is a carboxylic acid such as methacrylic acid, the tertiary alcohol (4) and the carboxylic acid may be heated in a solvent (e.g., toluene or hexane) in the presence of an acid catalyst, while water formed during reaction may be removed out of the system if desired. Suitable acid catalysts used herein include mineral acids such as hydrochloric acid, sulfuric acid, nitric acid and perchloric acid and organic acids such as p-toluenesulfonic acid and benzenesulfonic acid. In a further embodiment wherein the esterifying agent (5) used is an acid anhydride such as methacrylic anhydride, the tertiary alcohol (4), the acid anhydride, and a base (e.g., triethylamine, pyridine or 4-dimethylaminopyridine) may be successively or simultaneously added to a solventless system or to a solvent (e.g., methylene chloride, acetonitrile, toluene or hexane) while the reaction system may be cooled or heated as desired. The reaction time is determined as appropriate by monitoring the reaction process by GC or silica gel TLC because it is desirable from the yield aspect to drive the reaction to completion. Usually the reaction time is about 0.5 to about 24 hours. The desired monomer (1) may be recovered from the reaction mixture by ordinary aqueous work-up. If necessary, the monomer (1) may be purified by standard techniques like distillation, chromatography and recrystallization.

A second embodiment is a polymer comprising recurring units derived from the monomer having formula (1), the recurring units being represented by the general formula (A1).

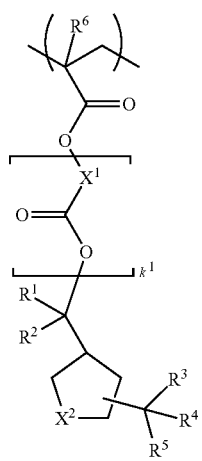

Herein, $R^1$, $R^2$, $R^3$, $R^4$, $R^5$, $R^6$, $X^1$, $X^2$, and $k^1$ are as defined above.

The polymer may have further copolymerized therein recurring units substituted with an acid labile group other than the acid labile group in the recurring units of formula (A1), the additional recurring units being represented by the general formula (A2).

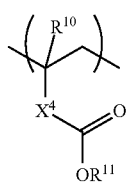

Herein, $R^{10}$ is hydrogen or methyl, $R^{11}$ is an acid labile group, and $X^4$ is a single bond, phenylene, naphthylene, or —C(=O)—O—$R^{12}$— wherein $R^{12}$ is a straight, branched or cyclic $C_1$-$C_{10}$ alkylene group which may contain an ether radical, ester radical, lactone ring or hydroxyl radical, or a phenylene or naphthylene group.

$X^4$ may be selected from the same structures as exemplified for $X^1$. The acid labile group $R^{11}$ will be described later.

In addition to the recurring units (A1) and (A2), the polymer may have further copolymerized therein recurring units having a hydroxyl group substituted with an acid labile group. Suitable recurring units having an acid labile group-substituted hydroxyl group include those units having the general formulae (B1) to (B4).

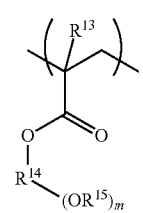

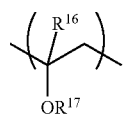

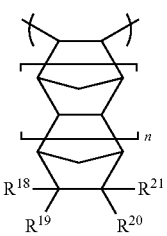

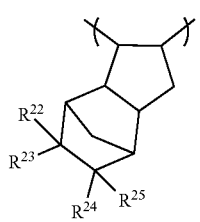

Herein $R^{13}$ and $R^{16}$ are each independently hydrogen or methyl; $R^{14}$ is a di- to pentavalent, straight, branched or cyclic $C_1$-$C_{16}$ aliphatic hydrocarbon group which may contain an ether or ester radical; $R^{15}$ and $R^{17}$ each are an acid labile group; $R^{18}$ to $R^{21}$ and $R^{22}$ to $R^{25}$ are each independently hydrogen, cyano, a straight, branched or cyclic $C_1$-$C_6$ alkyl group, alkoxycarbonyl, or a group having an ether radical or lactone ring, at least, one of $R^{18}$ to $R^{21}$ and $R^{22}$ to $R^{25}$ has a hydroxyl group substituted with an acid labile group; m is an integer of 1 to 4, and n is 0 or 1.

Examples of the monomers from which recurring units (B1) and (B2) are derived are shown below wherein $R^{13}$, $R^{15}$, $R^{16}$ and $R^{17}$ are as defined above.

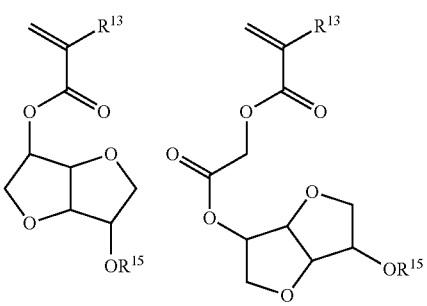

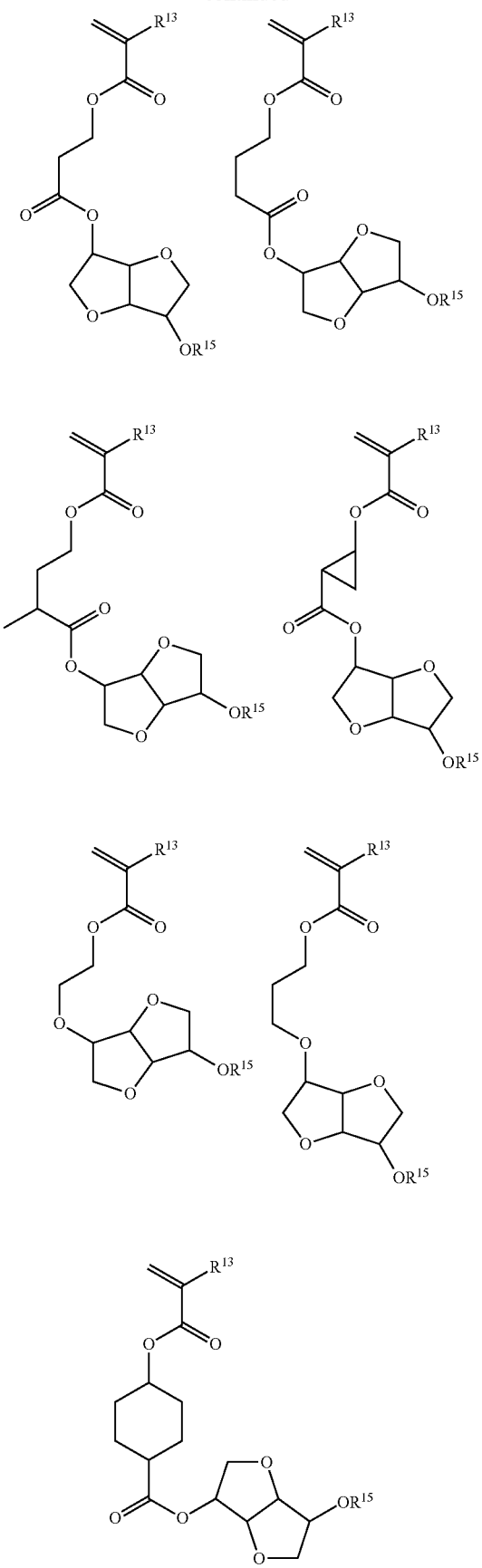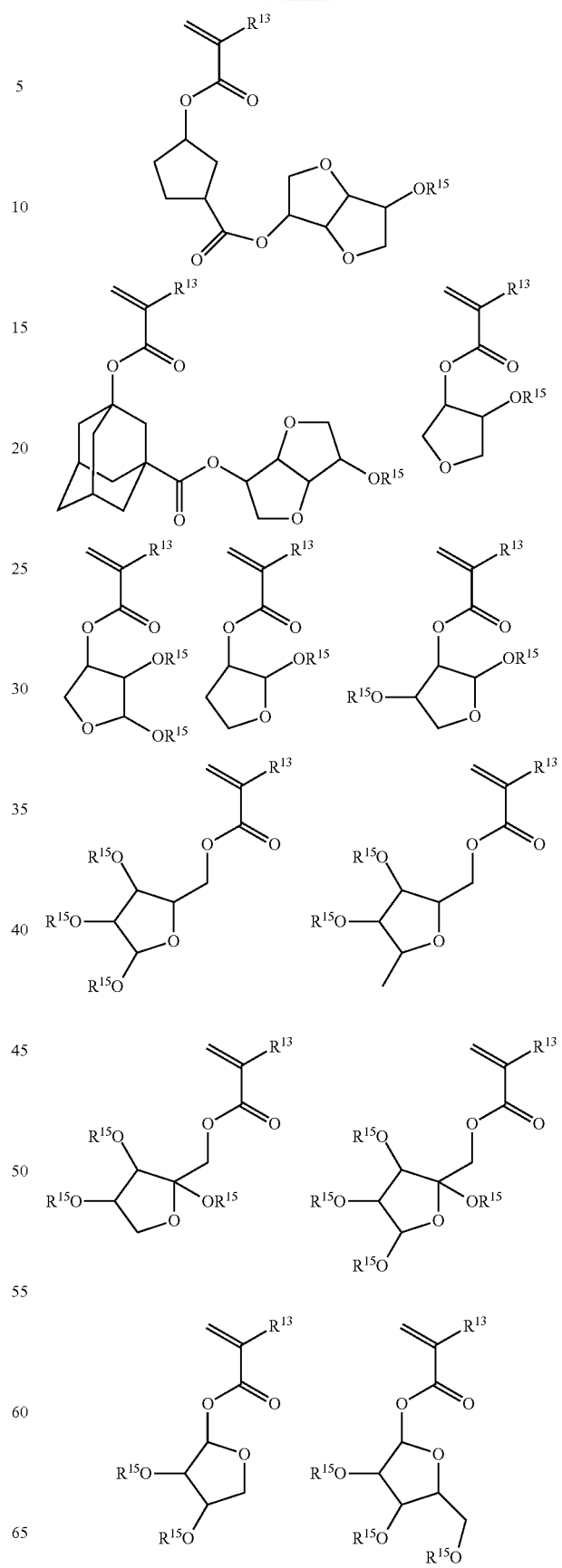

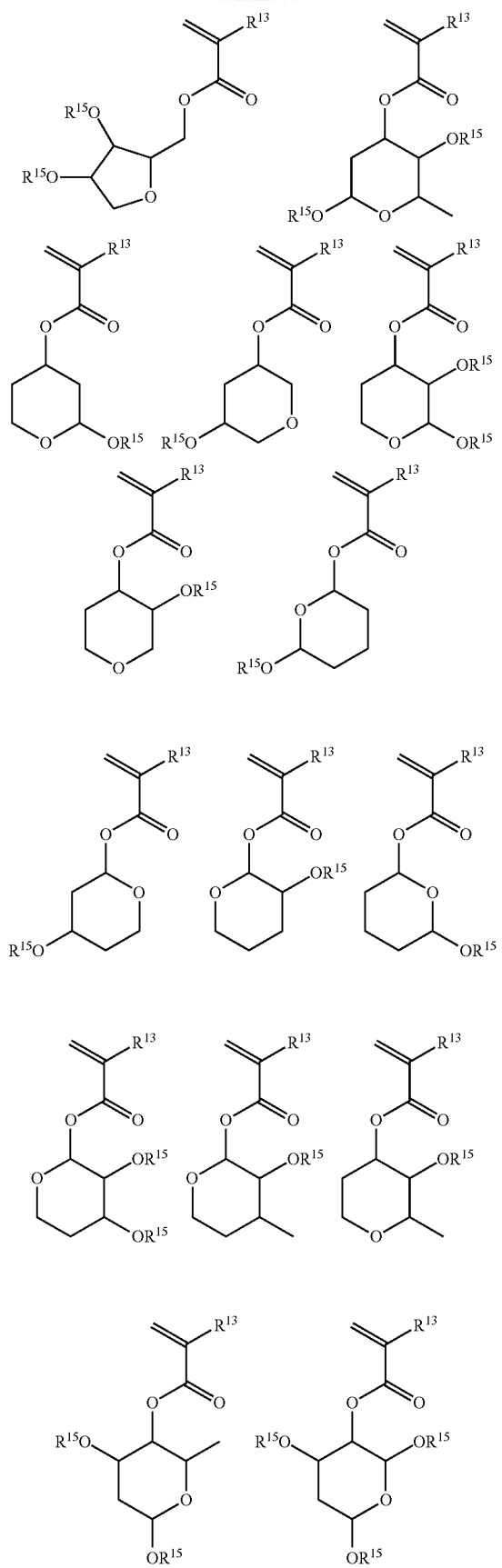
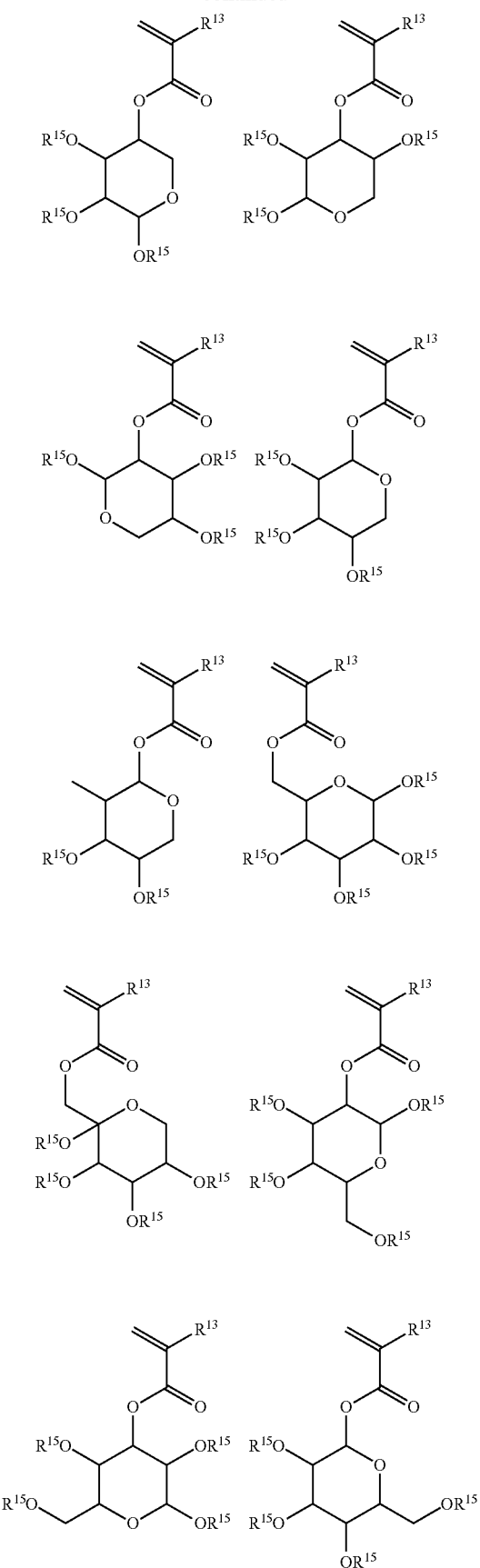

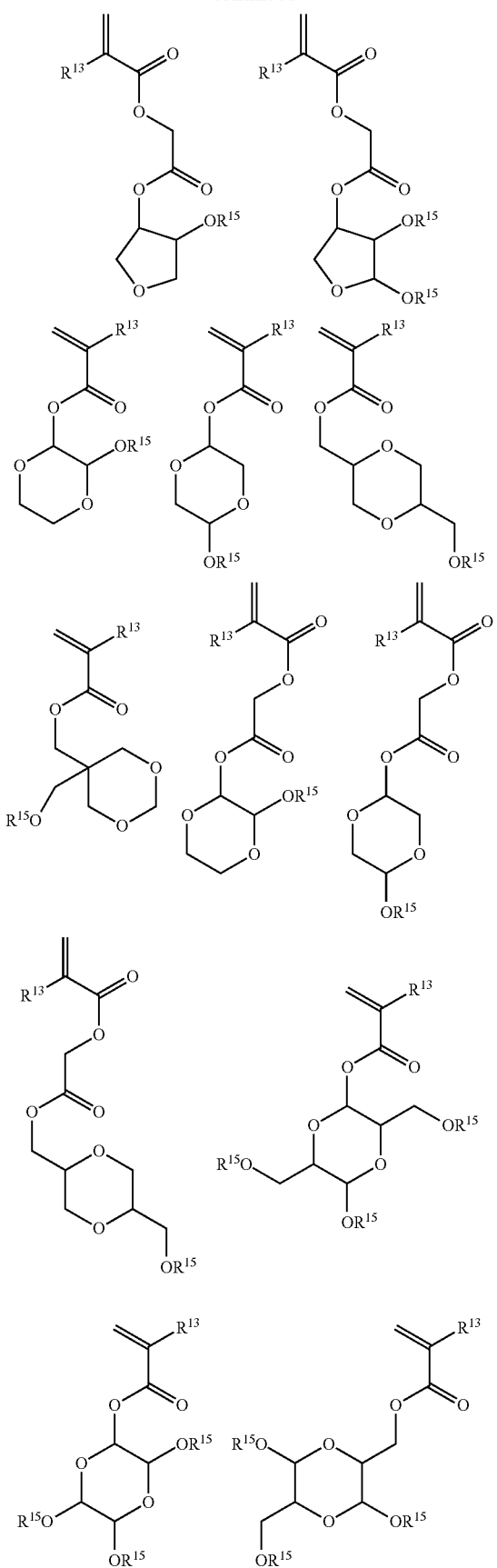
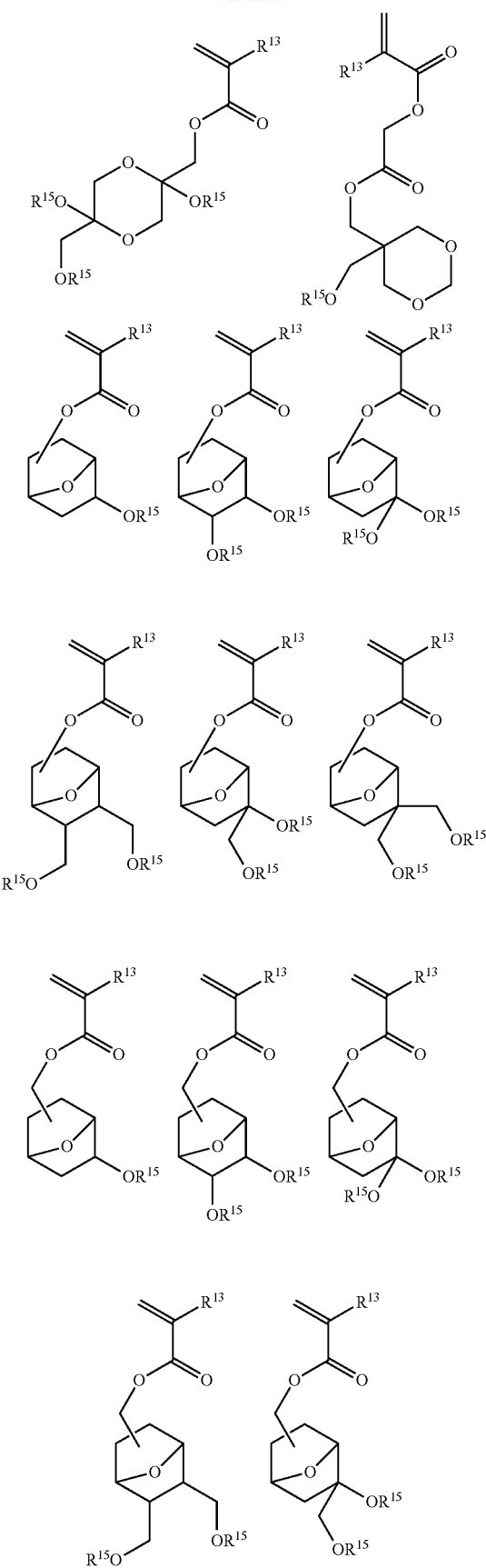

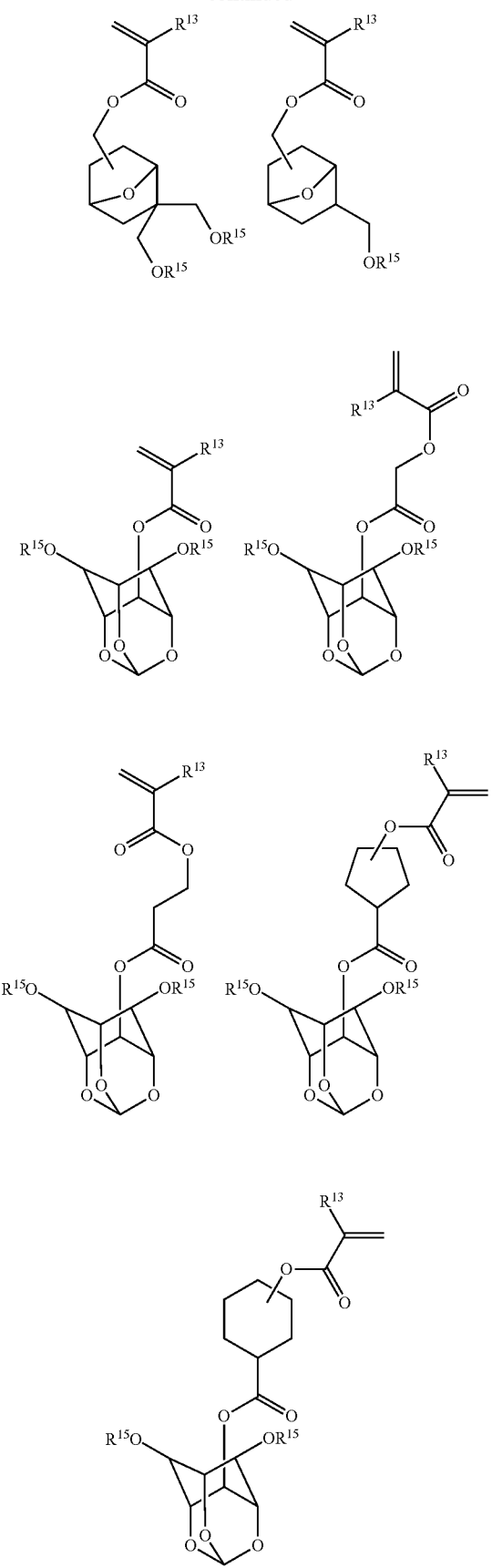
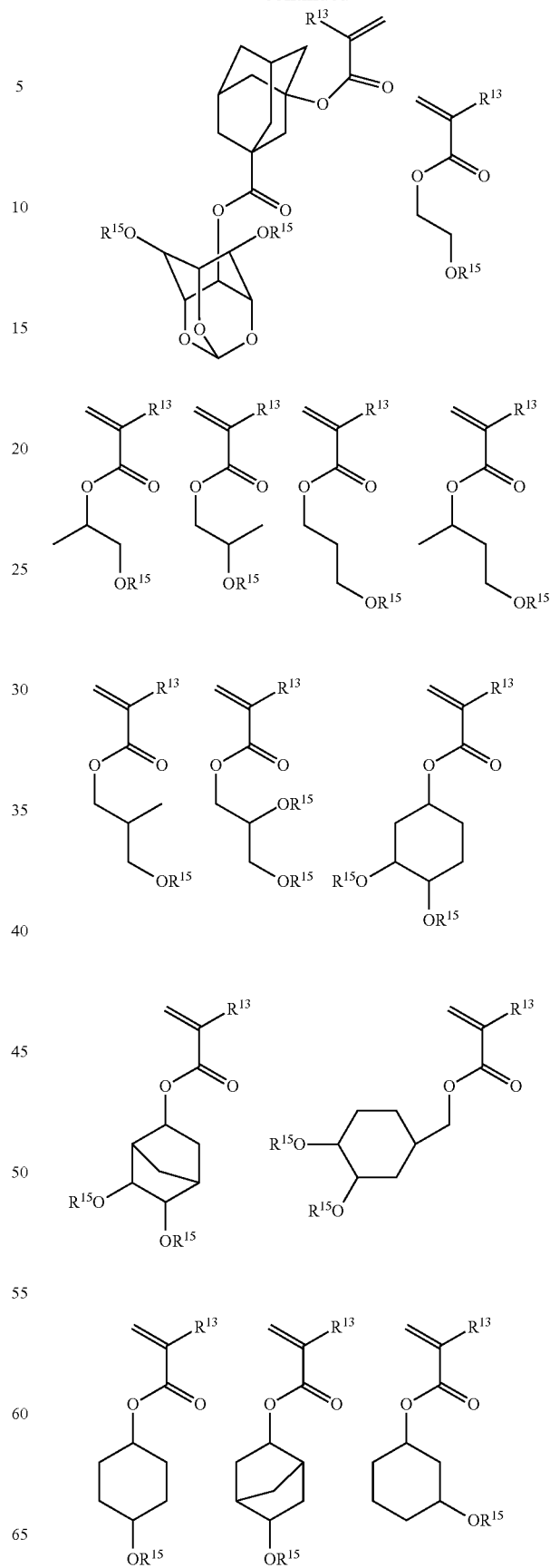

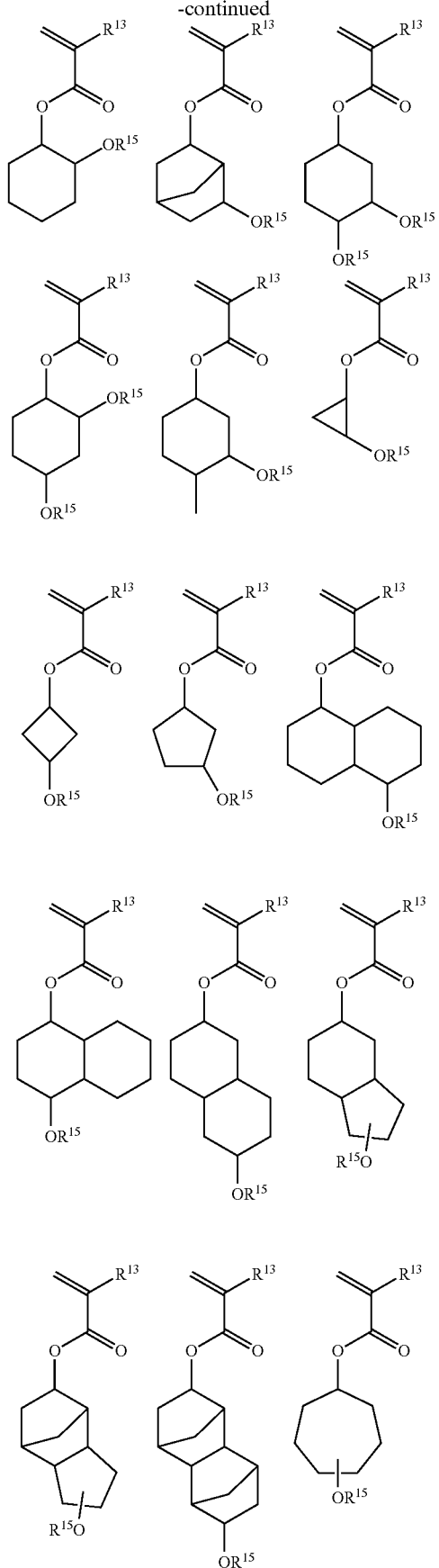
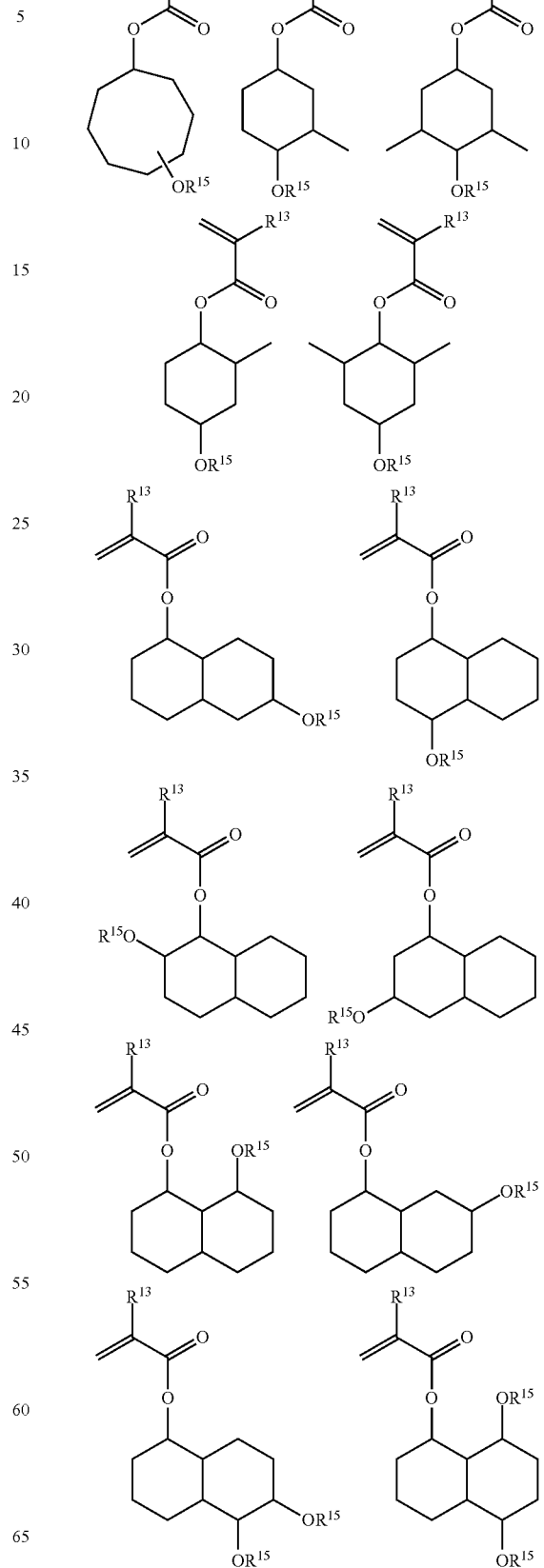

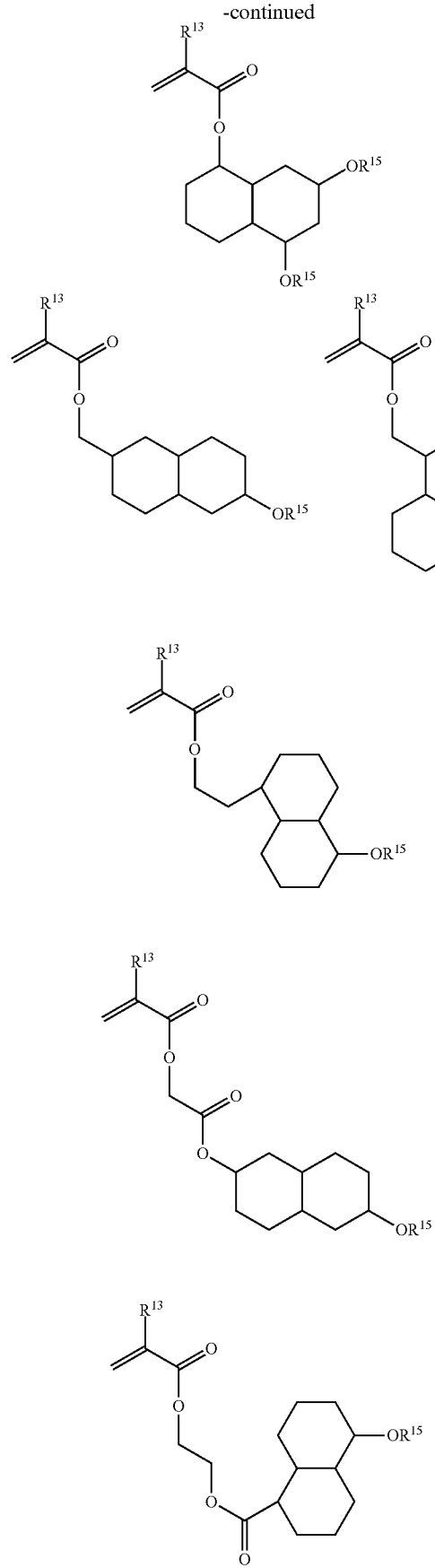
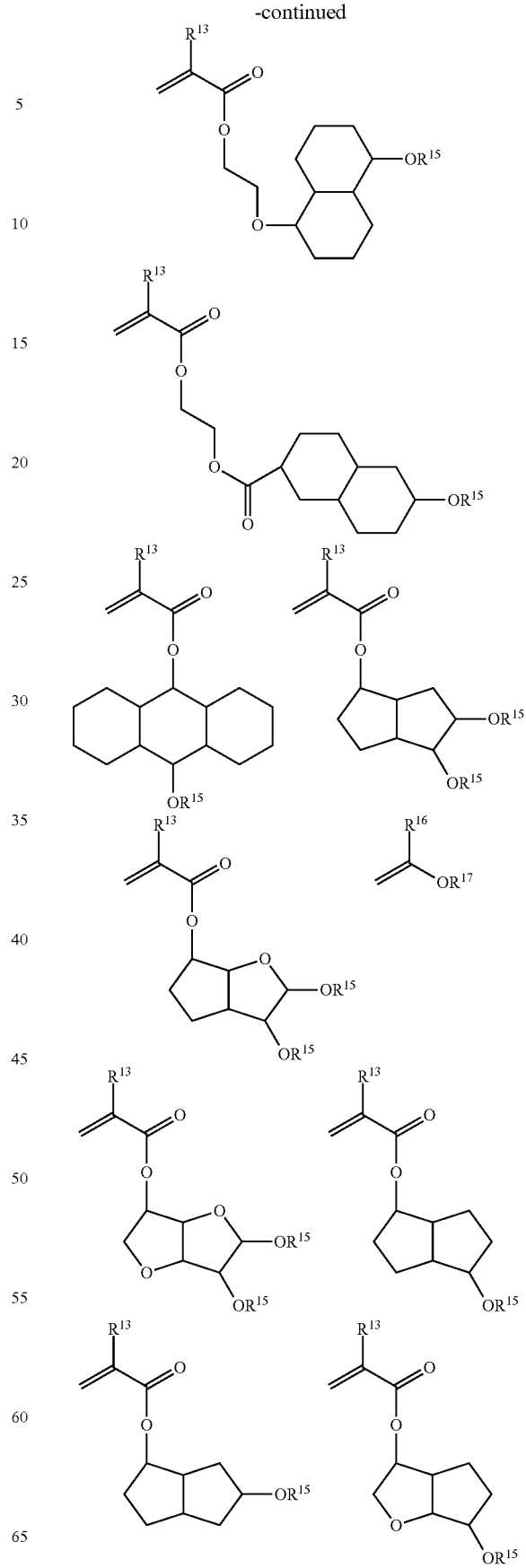

-continued
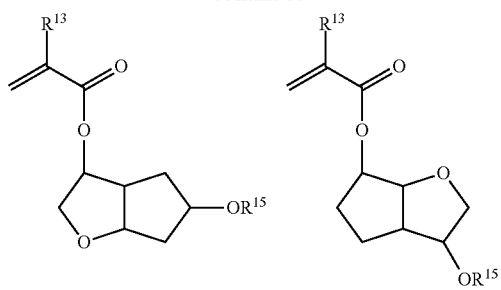
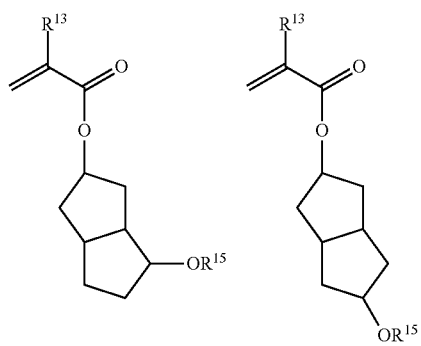
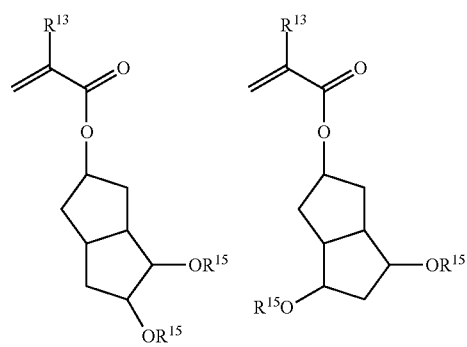
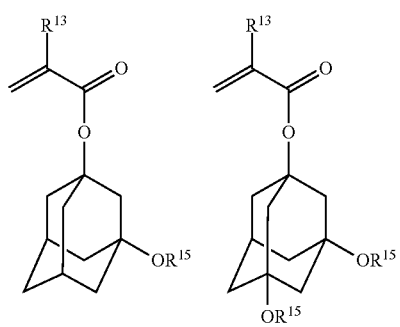
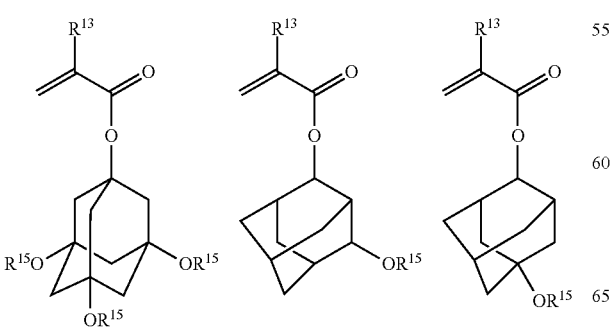
-continued
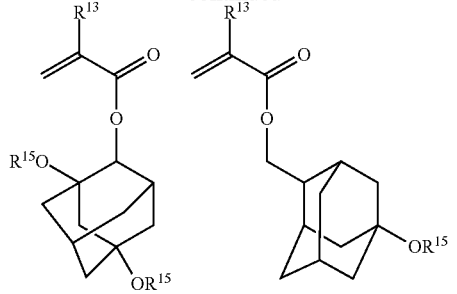
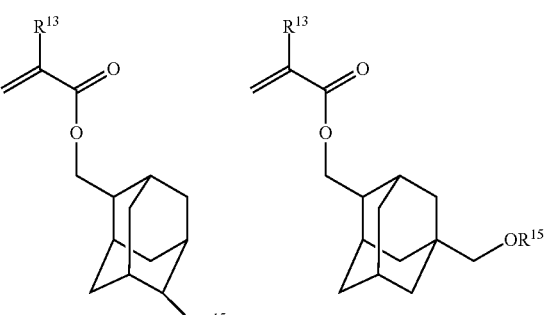
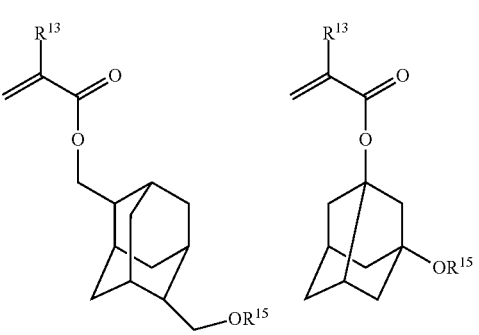
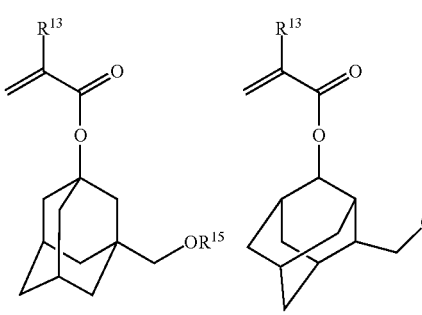
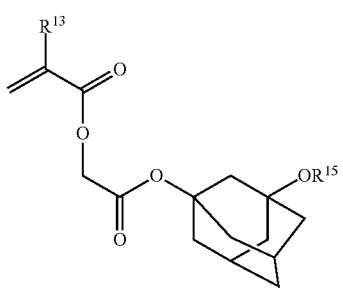

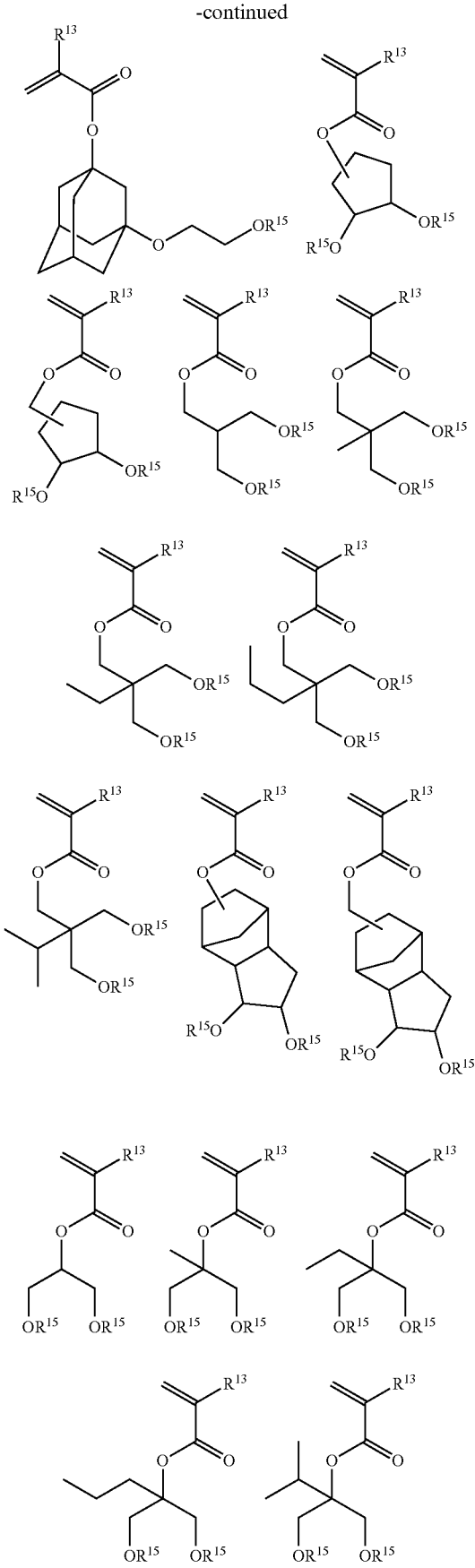
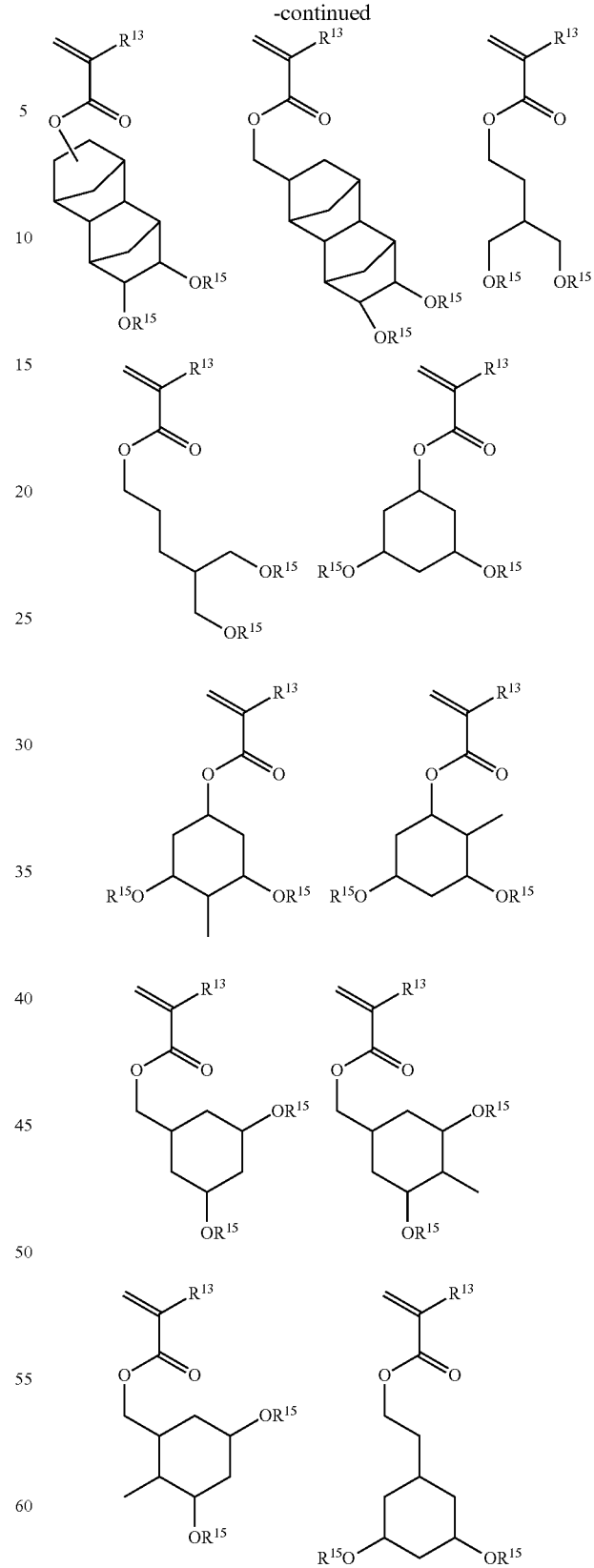
Examples of the monomers from which recurring units (B3) and (B4) are derived are shown below wherein R is an acid labile group.

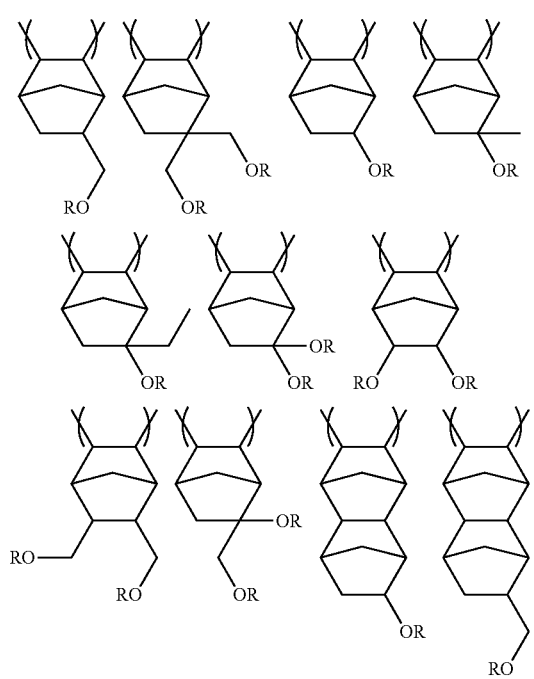
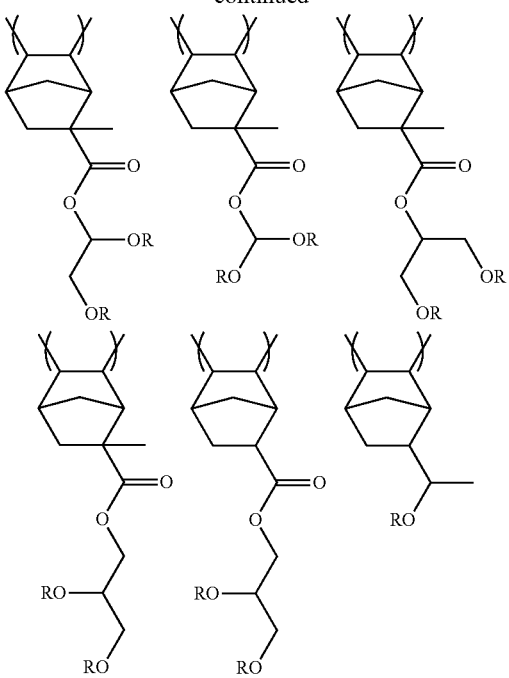
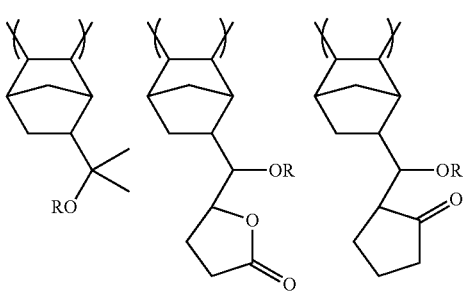
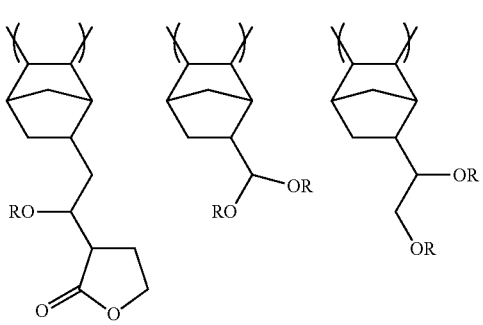
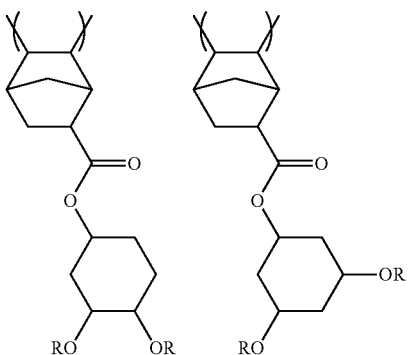

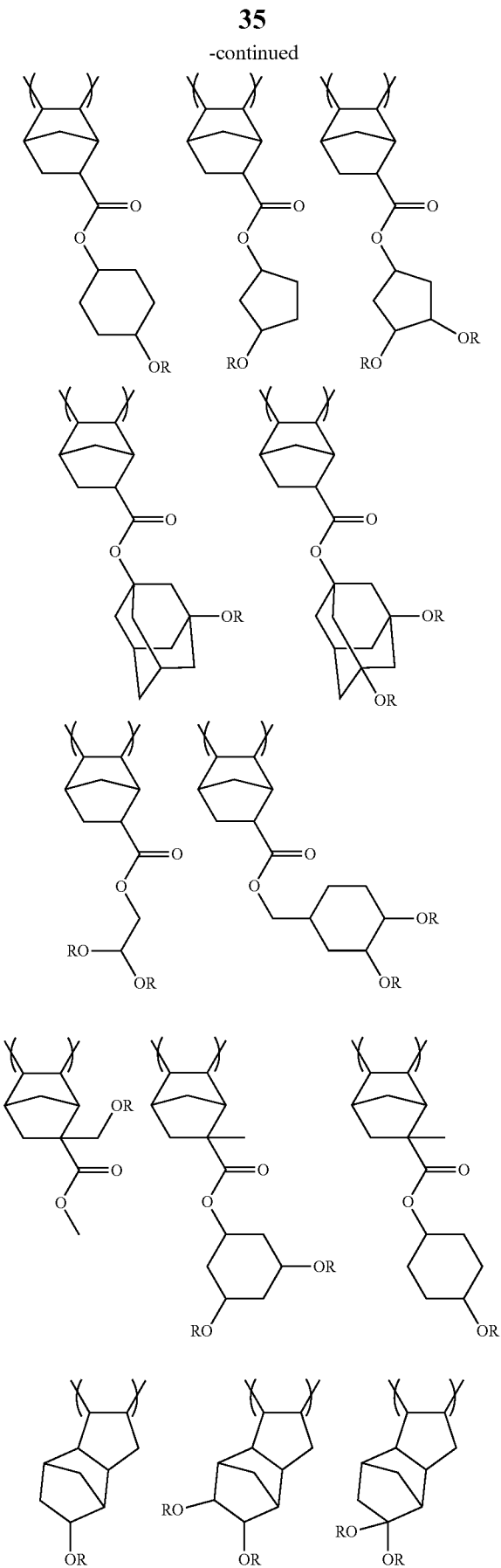
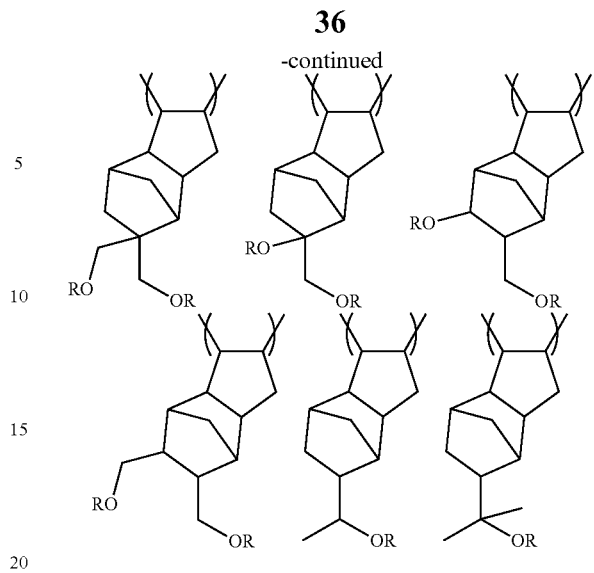

The acid labile group $R^{11}$ substituting on the carboxyl group in formula (A2) and the acid labile groups $R^{15}$, $R^{17}$ and R substituting on the hydroxyl group in formulae (B1) to (B4) may be selected from a variety of such groups while they may be the same or different. Suitable acid labile groups include groups of the formula (AL-10), acetal groups of the formula (AL-11), tertiary alkyl groups of the formula (AL-12), and $C_4$-$C_{20}$ oxoalkyl groups, but are not limited thereto.

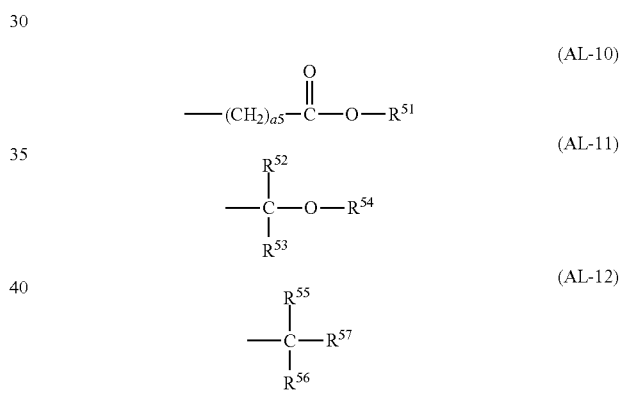

In formulae (AL-10) and (AL-11), $R^{51}$ and $R^{54}$ each are a monovalent hydrocarbon group, typically straight, branched or cyclic alkyl group, of 1 to 40 carbon atoms, more specifically 1 to 20 carbon atoms, which may contain a heteroatom such as oxygen, sulfur, nitrogen or fluorine. $R^{52}$ and $R^{53}$ each are hydrogen or a monovalent hydrocarbon group, typically straight, branched or cyclic alkyl group, of 1 to 20 carbon atoms which may contain a heteroatom such as oxygen, sulfur, nitrogen or fluorine. The subscript "a5" is an integer of 0 to 10, and especially 1 to 5. Alternatively, a pair of $R^{52}$ and $R^{53}$, $R^{52}$ and $R^{54}$, or $R^{53}$ and $R^{54}$ may bond together to form a ring, specifically aliphatic ring, with the carbon atom or the carbon and oxygen atoms to which they are attached, the ring having 3 to 20 carbon atoms, especially 4 to 16 carbon atoms.

In formula (AL-12), $R^{55}$, $R^{56}$ and $R^{57}$ each are a monovalent hydrocarbon group, typically straight, branched or cyclic alkyl group, of 1 to 20 carbon atoms which may contain a heteroatom such as oxygen, sulfur, nitrogen or fluorine. Alternatively, a pair of $R^{55}$ and $R^{56}$, $R^{55}$ and $R^{57}$, or $R^{56}$ and $R^{57}$ may bond together to form a ring, specifically aliphatic ring, with the carbon atom to which they are attached, the ring having 3 to 20 carbon atoms, especially 4 to 16 carbon atoms.

Illustrative examples of the acid labile group of formula (AL-10) include tert-butoxycarbonyl, tert-butoxycarbonylmethyl, tert-amyloxycarbonyl, tert-amyloxycarbonylmethyl, 1-ethoxyethoxycarbonylmethyl, 2-tetrahydropyranyloxycarbonylmethyl and 2-tetrahydrofuranyloxycarbonylmethyl as well as substituent groups of the following formulae (AL-10)-1 to (AL-10)-10.

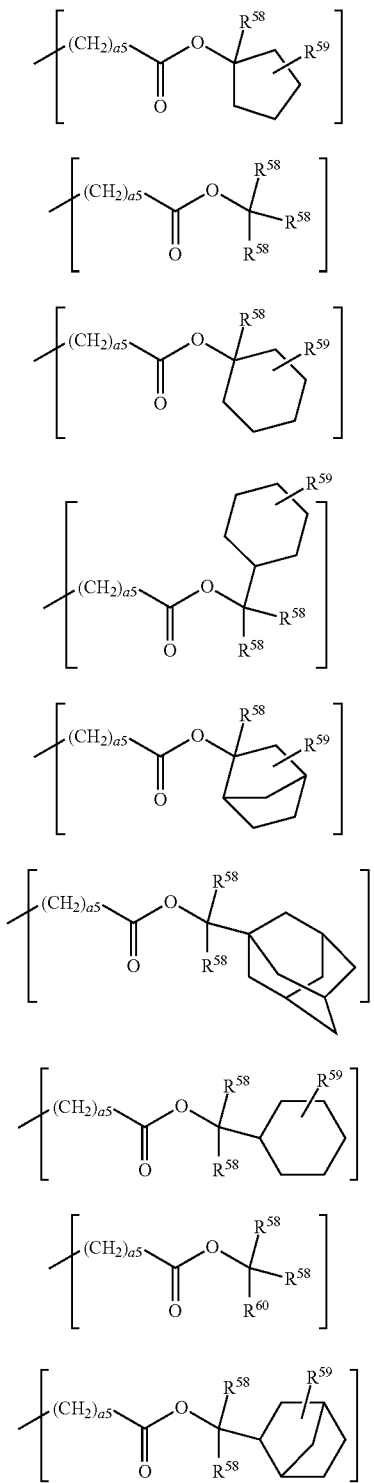

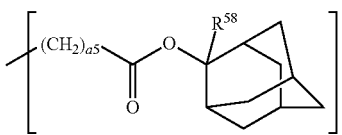

In formulae (AL-10)-1 to (AL-10)-10, $R^{58}$ is each independently a straight, branched or cyclic $C_1$-$C_8$ alkyl group, $C_6$-$C_{20}$ aryl group or $C_7$-$C_{20}$ aralkyl group; $R^{59}$ is hydrogen or a straight, branched or cyclic $C_1$-$C_{20}$ alkyl group; $R^{60}$ is a $C_6$-$C_{20}$ aryl group or $C_7$-$C_{20}$ aralkyl group; and a5 is an integer of 0 to 10, especially 1 to 5.

Illustrative examples of the acetal group of formula (AL-11) include those of the following formulae (AL-11)-1 to (AL-11)-112.

(AL-11)-1
$$—CH_2—O—CH_3$$

(AL-11)-2
$$—CH_2—O—CH_2—CH_3$$

(AL-11)-3
$$—CH_2—O—(CH_2)_2—CH_3$$

(AL-11)-4
$$—CH_2—O—(CH_2)_3—CH_3$$

(AL-11)-5
$$—CH_2—O—\underset{CH_3}{\underset{|}{CH}}—CH_3$$

(AL-11)-6
$$—CH_2—O—\underset{CH_3}{\overset{CH_3}{\underset{|}{\overset{|}{C}}}}—CH_3$$

(AL-11)-7
$$—\underset{|}{\overset{CH_3}{CH}}—O—CH_3$$

(AL-11)-8
$$—\underset{|}{\overset{CH_2}{\underset{CH}{|}}}—O—CH_3$$
(with $CH_3$ on top)

(AL-11)-9
$$—\underset{|}{\overset{(CH_2)_2}{\underset{CH}{|}}}—O—CH_3$$
(with $CH_3$ on top)

(AL-11)-10
$$—\underset{|}{\overset{CH_3}{CH}}—O—CH_2—CH_3$$

(AL-11)-11
$$—\underset{|}{\overset{CH_2}{\underset{CH}{|}}}—O—CH_2—CH_3$$
(with $CH_3$ on top)

(AL-11)-12
$$—\underset{|}{\overset{CH—CH_3}{CH}}—O—CH_2—CH_3$$
(with $CH_3$ on top)

(AL-11)-13
$$—\underset{|}{\overset{CH_3}{CH}}—O—(CH_2)_2—CH_3$$

(AL-11)-14 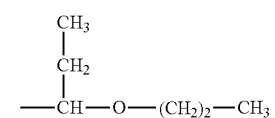
(AL-11)-15 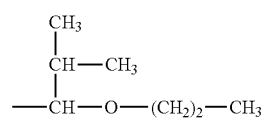
(AL-11)-16 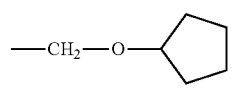
(AL-11)-17 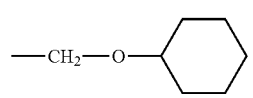
(AL-11)-18 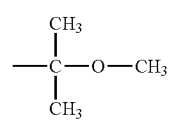
(AL-11)-19 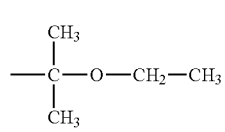
(AL-11)-20 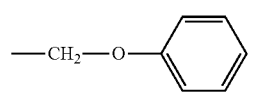
(AL-11)-21 
(AL-11)-22 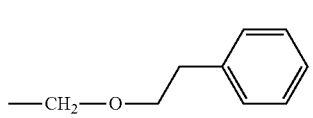
(AL-11)-23 
(AL-11)-24 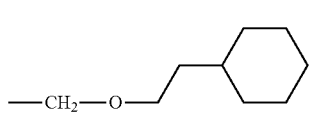
(AL-11)-25 
(AL-11)-26 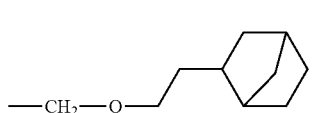
(AL-11)-27 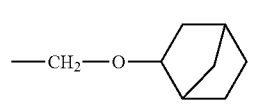
(AL-11)-28 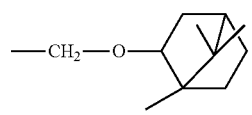
(AL-11)-29 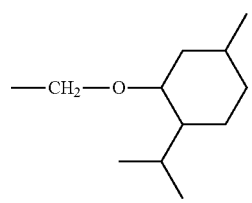
(AL-11)-30 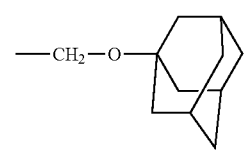
(AL-11)-31 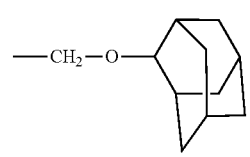
(AL-11)-32 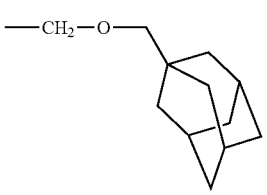
(AL-11)-33 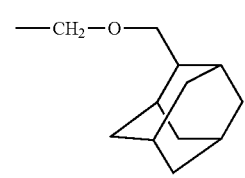
(AL-11)-34 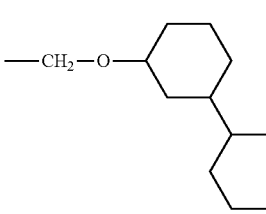
(AL-11)-35 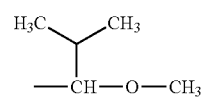
(AL-11)-36 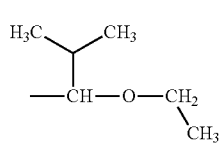
(AL-11)-37 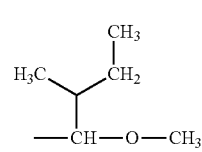

(AL-11)-38
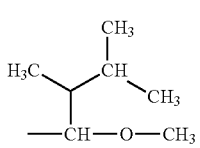
(AL-11)-39
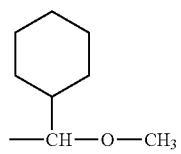
(AL-11)-40
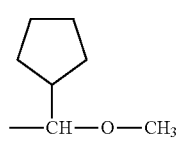
(AL-11)-41
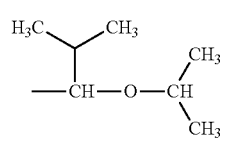
(AL-11)-42
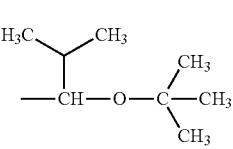
(AL-11)-43
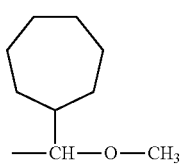
(AL-11)-44
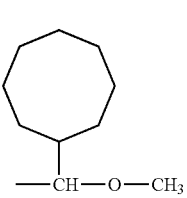
(AL-11)-45
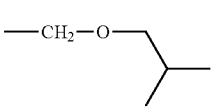
(AL-11)-46
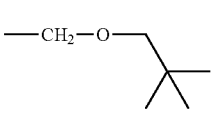
(AL-11)-47
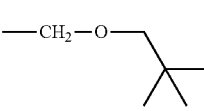
(AL-11)-48
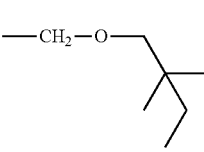
(AL-11)-49
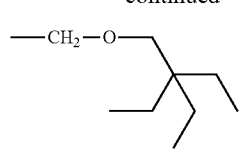
(AL-11)-50
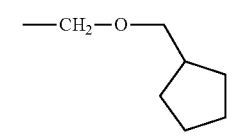
(AL-11)-51
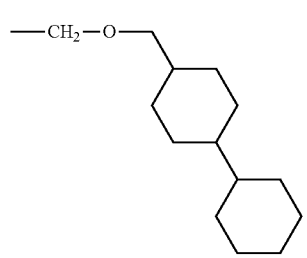
(AL-11)-52
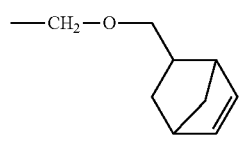
(AL-11)-53
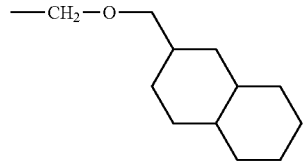
(AL-11)-54
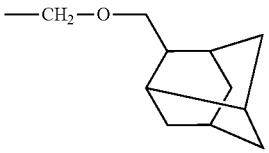
(AL-11)-55
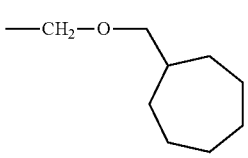
(AL-11)-56
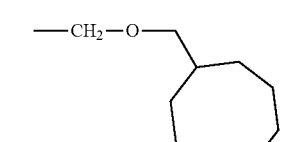
(AL-11)-57
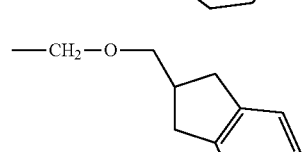
(AL-11)-58
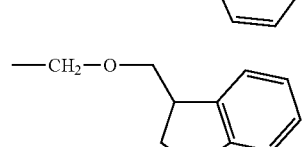

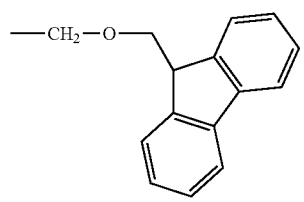 (AL-11)-59
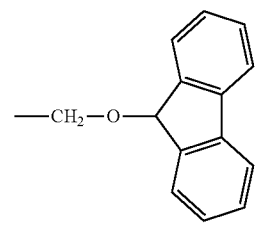 (AL-11)-60
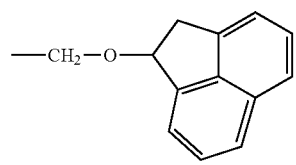 (AL-11)-61
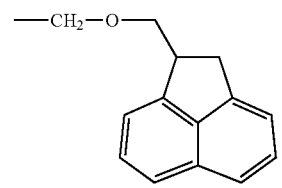 (AL-11)-62
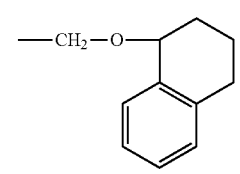 (AL-11)-63
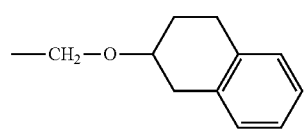 (AL-11)-64
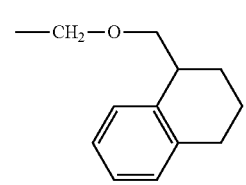 (AL-11)-65
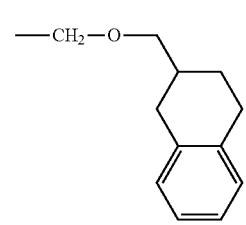 (AL-11)-66
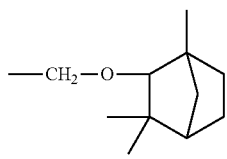 (AL-11)-67
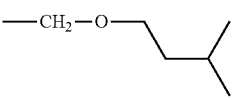 (AL-11)-68
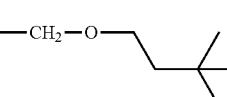 (AL-11)-69
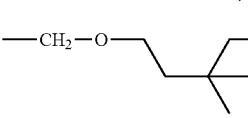 (AL-11)-70
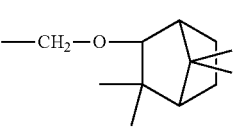 (AL-11)-71
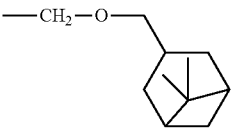 (AL-11)-72
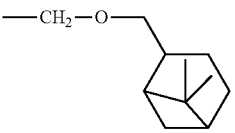 (AL-11)-73
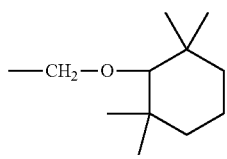 (AL-11)-74
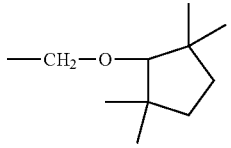 (AL-11)-75
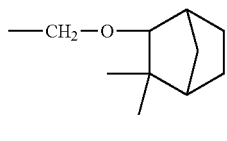 (AL-11)-76
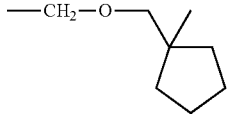 (AL-11)-77
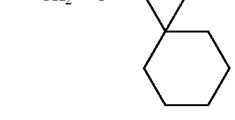 (AL-11)-78

(AL-11)-79
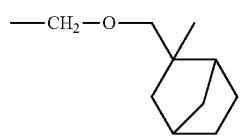
(AL-11)-80
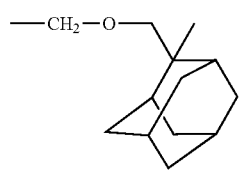
(AL-11)-81
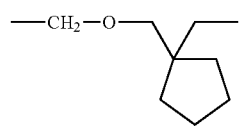
(AL-11)-82
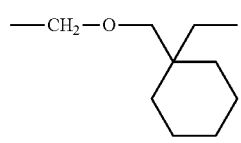
(AL-11)-83
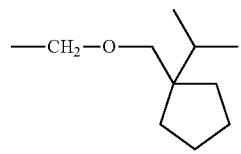
(AL-11)-84
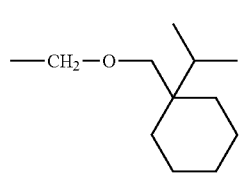
(AL-11)-85
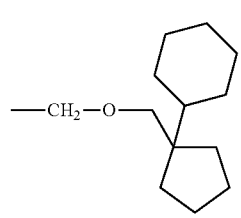
(AL-11)-86
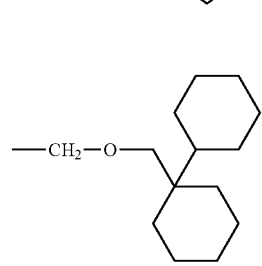
(AL-11)-87
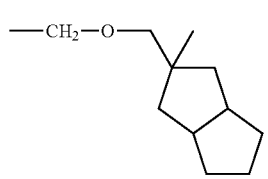
(AL-11)-88
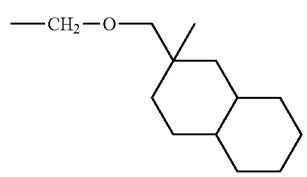
(AL-11)-89
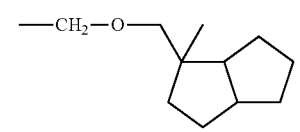
(AL-11)-90
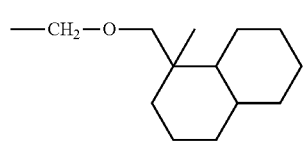
(AL-11)-91
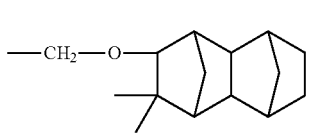
(AL-11)-92
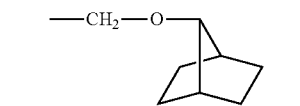
(AL-11)-93
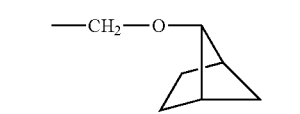
(AL-11)-94
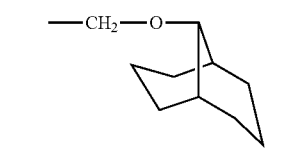
(AL-11)-95
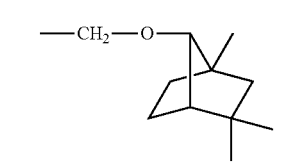
(AL-11)-96
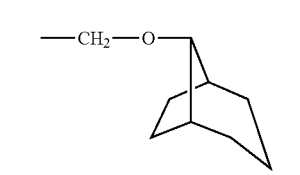
(AL-11)-97
(AL-11)-98

(AL-11)-99 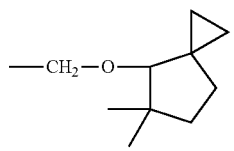
(AL-11)-100 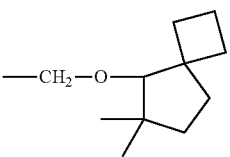
(AL-11)-101 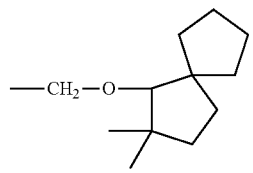
(AL-11)-102 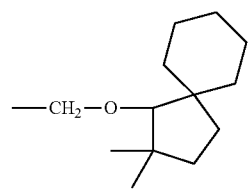
(AL-11)-103 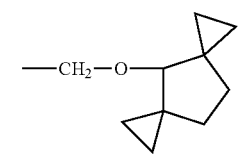
(AL-11)-104 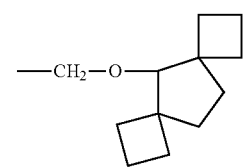
(AL-11)-105 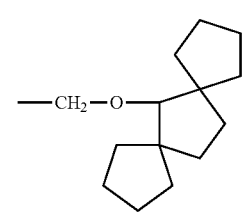
(AL-11)-106 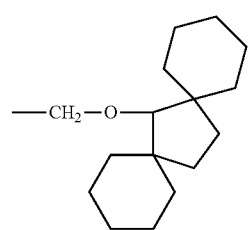
(AL-11)-107 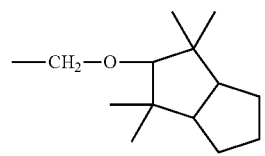
(AL-11)-108 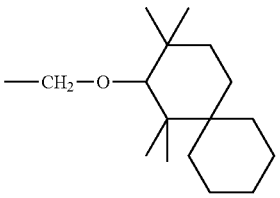
(AL-11)-109 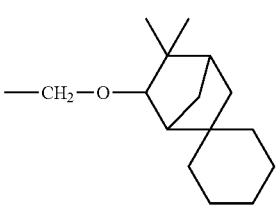
(AL-11)-110 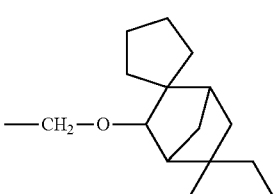
(AL-11)-111 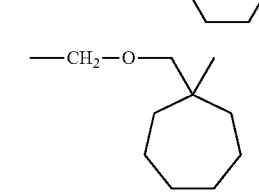
(AL-11)-112 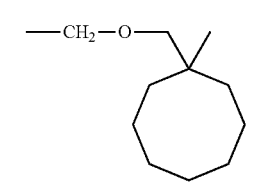
Other examples of acid labile groups include those of the following formula (AL-11a) or (AL-11b) while the polymer may be crosslinked within the molecule or between molecules with these acid labile groups.
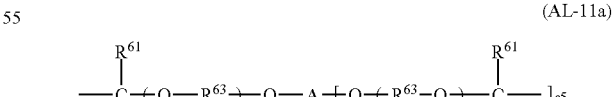
(AL-11a)
(AL-11b)

Herein $R^{61}$ and $R^{62}$ each are hydrogen or a straight, branched or cyclic $C_1$-$C_8$ alkyl group, or $R^{61}$ and $R^{62}$ may bond together to form a ring with the carbon atom to which they are attached, and $R^{61}$ and $R^{62}$ are straight or branched $C_1$-$C_8$ alkylene groups when they form a ring. $R^{63}$ is a straight, branched or cyclic $C_1$-$C_{10}$ alkylene group. Each of b5 and d5 is 0 or an integer of 1 to 10, preferably 0 or an integer of 1 to 5, and c5 is an integer of 1 to 7. "A" is a (c5+1)-valent aliphatic or alicyclic saturated hydrocarbon group, aromatic hydrocarbon group or heterocyclic group having 1 to 50 carbon atoms, which may be separated by a heteroatom such as oxygen, sulfur or nitrogen or in which some hydrogen atoms attached to carbon atoms may be substituted by hydroxyl, carboxyl, carbonyl radicals or fluorine atoms. "B" is —CO—O—, —NHCO—O— or —NH-CONH—.

Preferably, "A" is selected from divalent to tetravalent, straight, branched or cyclic $C_1$-$C_{20}$ alkylene, alkanetriyl and alkanetetrayl groups, and $C_6$-$C_{30}$ arylene groups, which may be separated by a heteroatom such as oxygen, sulfur or nitrogen or in which some hydrogen atoms attached to carbon atoms may be substituted by hydroxyl, carboxyl, acyl radicals or halogen atoms. The subscript c5 is preferably an integer of 1 to 3.

The crosslinking acetal groups of formulae (AL-11a) and (AL-11b) are exemplified by the following formulae (AL-11)-113 through (AL-11)-120.

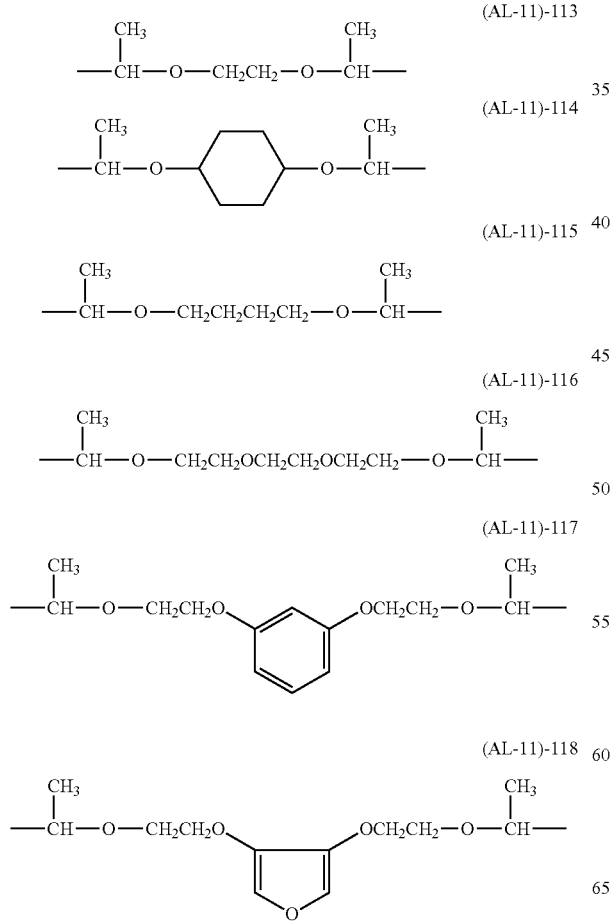

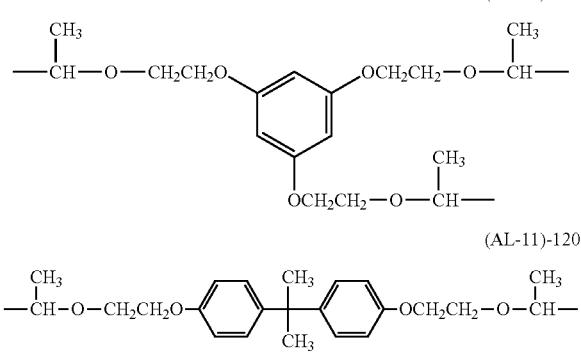

Illustrative examples of the tertiary alkyl group of formula (AL-12) include tert-butyl, triethylcarbyl, 1-ethylnorbornyl, 1-methylcyclohexyl, 1-ethylcyclopentyl, and tert-amyl groups as well as those of (AL-12)-1 to (AL-12)-16.

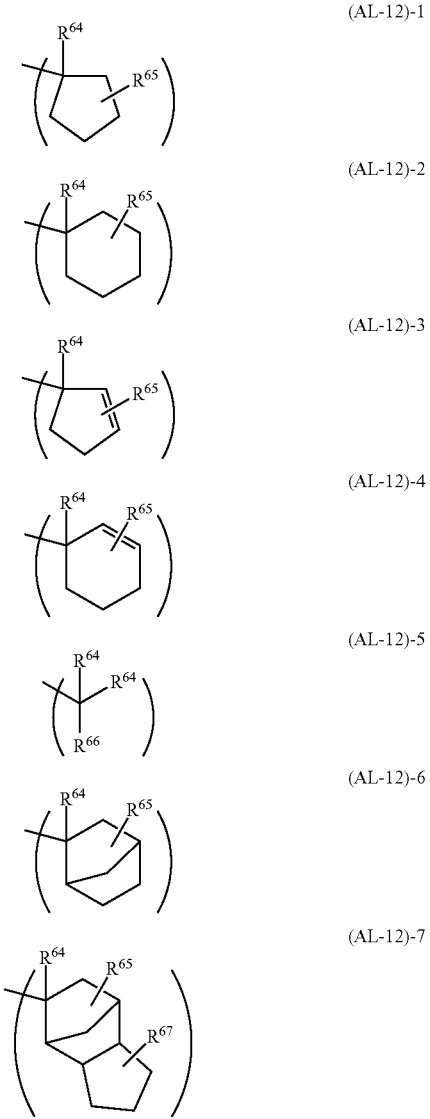

-continued (AL-12)-8 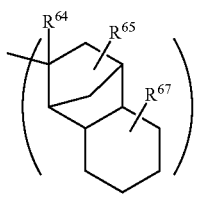

(AL-12)-9 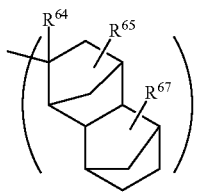

(AL-12)-10 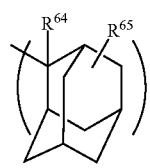

(AL-12)-11 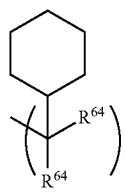

(AL-12)-12 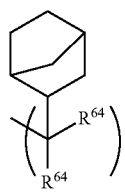

(AL-12)-13 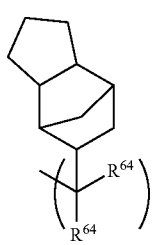

(AL-12)-14 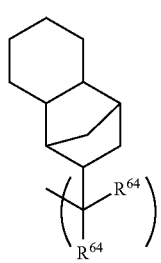

-continued (AL-12)-15 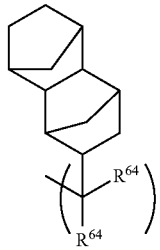

(AL-12)-16 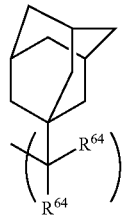

Herein $R^{64}$ is each independently a straight, branched or cyclic $C_1$-$C_8$ alkyl group, $C_6$-$C_{20}$ aryl group or $C_7$-$C_{20}$ aralkyl group, or two $R^{64}$ groups may bond together to form a ring, $R^{65}$ and $R^{67}$ each are hydrogen, methyl or ethyl. $R^{66}$ is a $C_6$-$C_{20}$ aryl group or $C_7$-$C_{20}$ aralkyl group.

With acid labile groups containing $R^{68}$ representative of a di- or poly-valent alkylene or arylene group as shown by formula (AL-12)-17, the polymer may be crosslinked within the molecule or between molecules. In formula (AL-12)-17, $R^{64}$ is as defined above, $R^{68}$ is a single bond, a straight, branched or cyclic $C_1$-$C_{20}$ alkylene group or arylene group, which may contain a heteroatom such as oxygen, sulfur or nitrogen, and b6 is an integer of 0 to 3. It is noted that formula (AL-12)-17 is applicable to all the foregoing acid labile groups $R^{11}$, $R^{15}$, $R^{17}$ and R.

(AL-12)-17 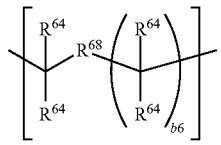

The groups represented by $R^{64}$, $R^{65}$, $R^{66}$ and $R^{67}$ may contain a heteroatom such as oxygen, nitrogen or sulfur. Such groups are exemplified by those of the following formulae (AL-13)-1 to (AL-13)-7.

(AL-13)-1 
—(CH$_2$)$_4$OH (AL-13)-2 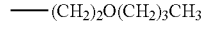
—(CH$_2$)$_2$O(CH$_2$)$_3$CH$_3$ (AL-13)-3 
—CH$_2$—⟨ ⟩—CH$_2$OH (AL-13)-4 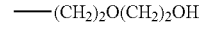
—(CH$_2$)$_2$O(CH$_2$)$_2$OH (AL-13)-5 
—(CH$_2$)$_6$OH

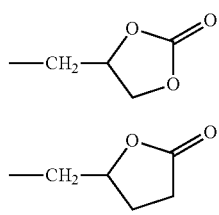

While the polymer used as the base resin in the resist composition comprises essentially recurring units (A1) and optionally (and preferably) recurring units (A2), (B1) to (B4) having an acid labile group, it may have further copolymerized therein recurring units (C1) derived from monomers having adhesive groups such as hydroxy, cyano, carbonyl, ester, ether groups, lactone rings, carboxyl, carboxylic anhydride, sulfonic acid ester, disulfone or carbonate groups. Of these, recurring units having lactone ring as the adhesive group are most preferred.

Examples of suitable monomers from which recurring units (C1) are derived are given below.

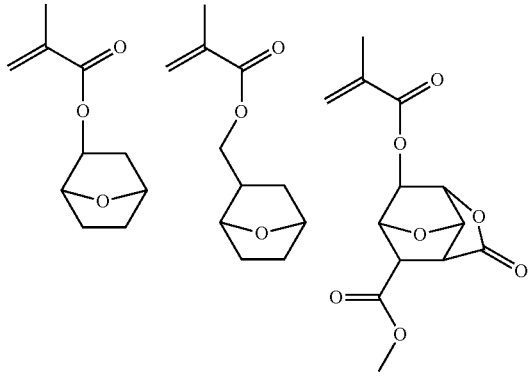

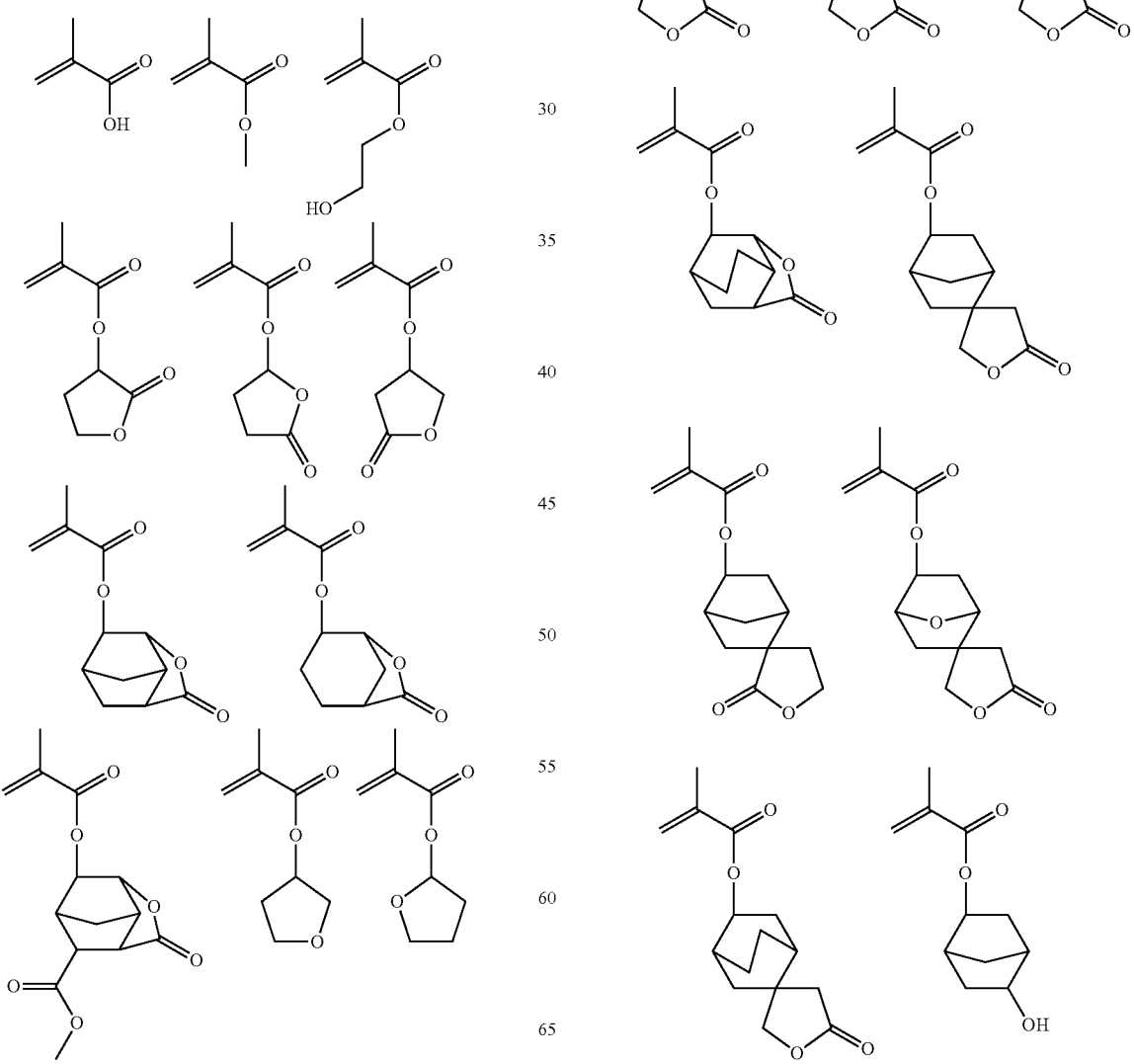

55
-continued
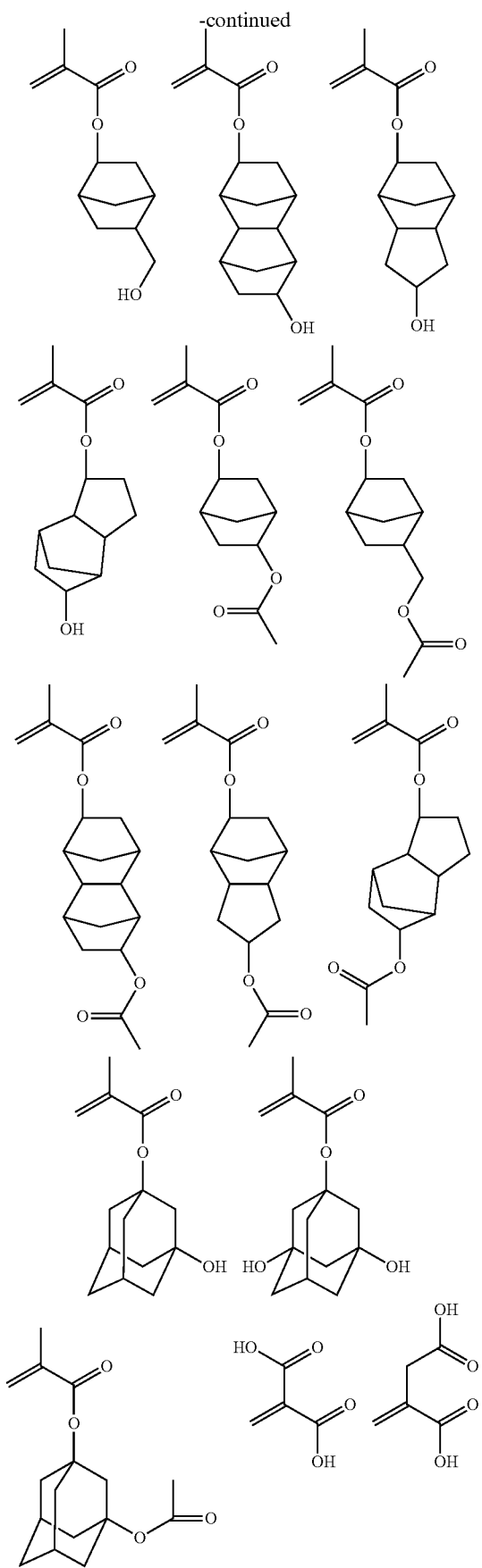
56
-continued
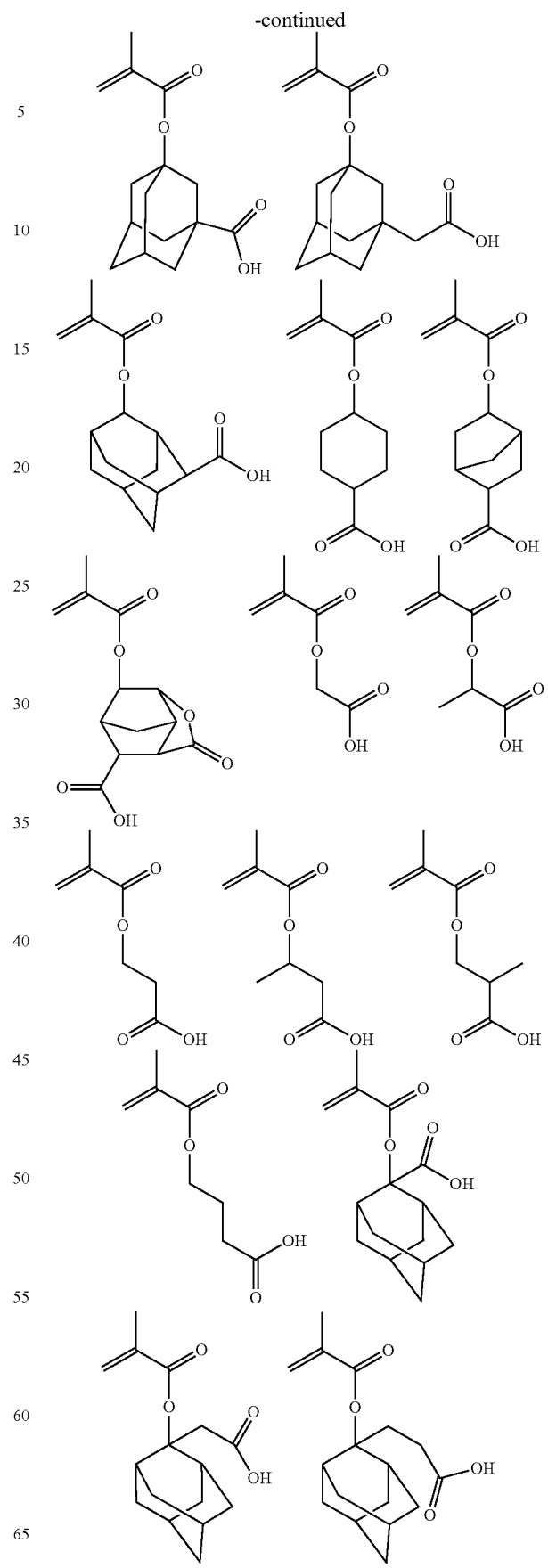

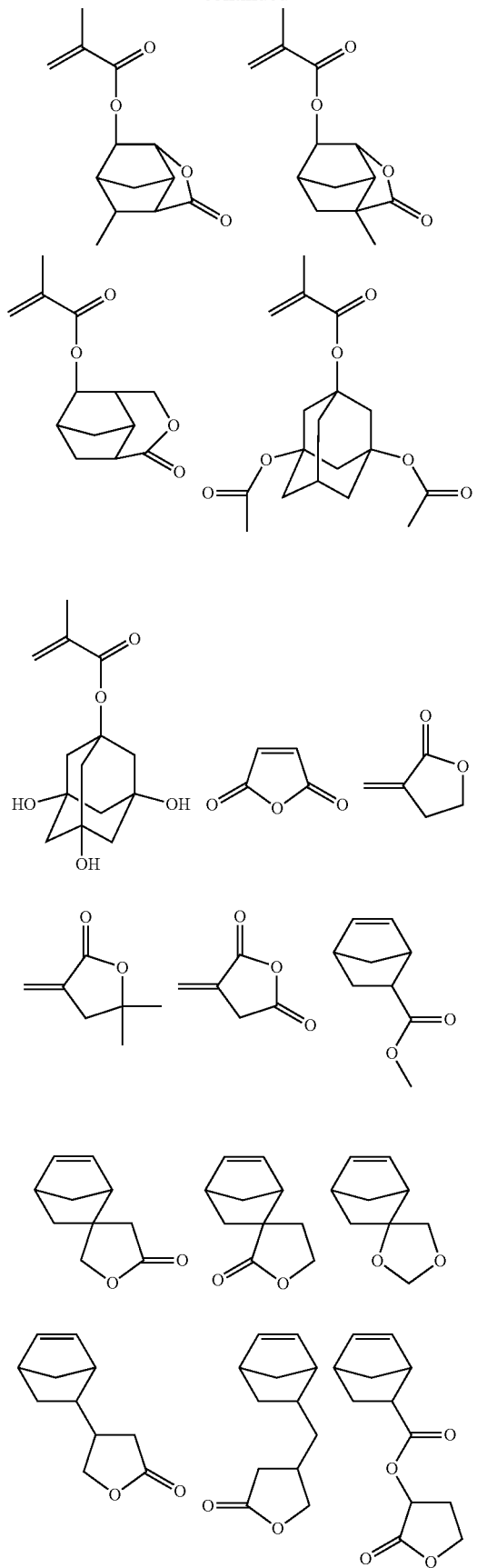
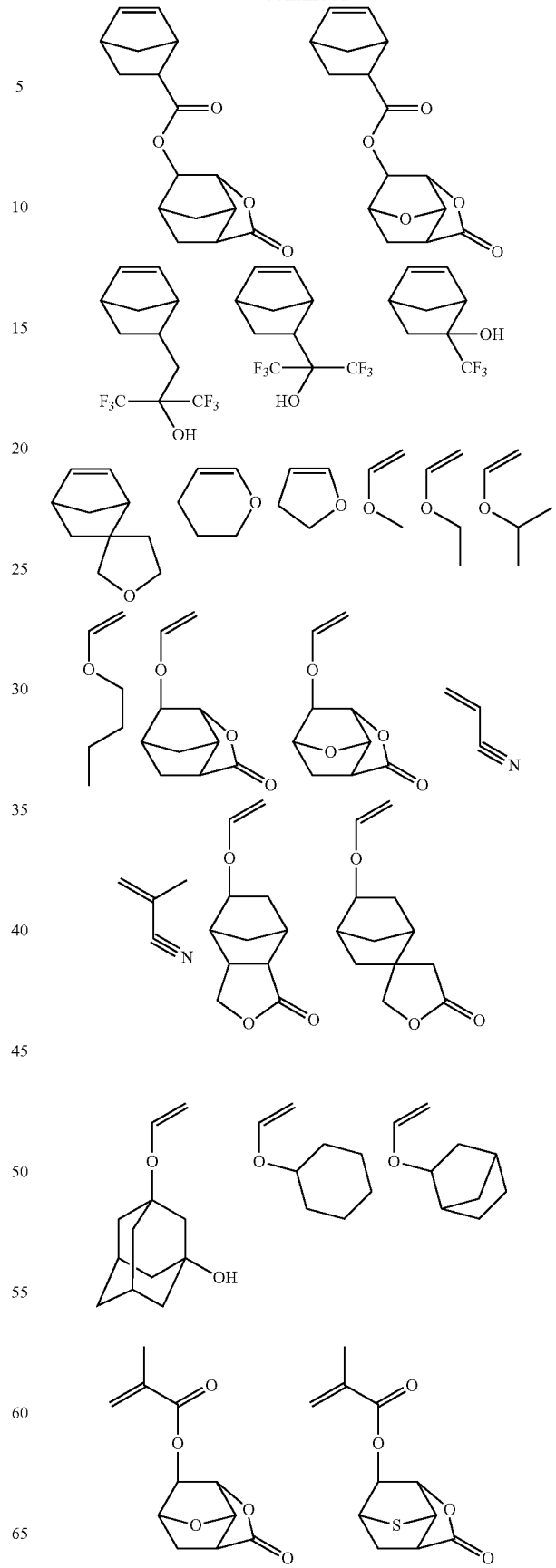

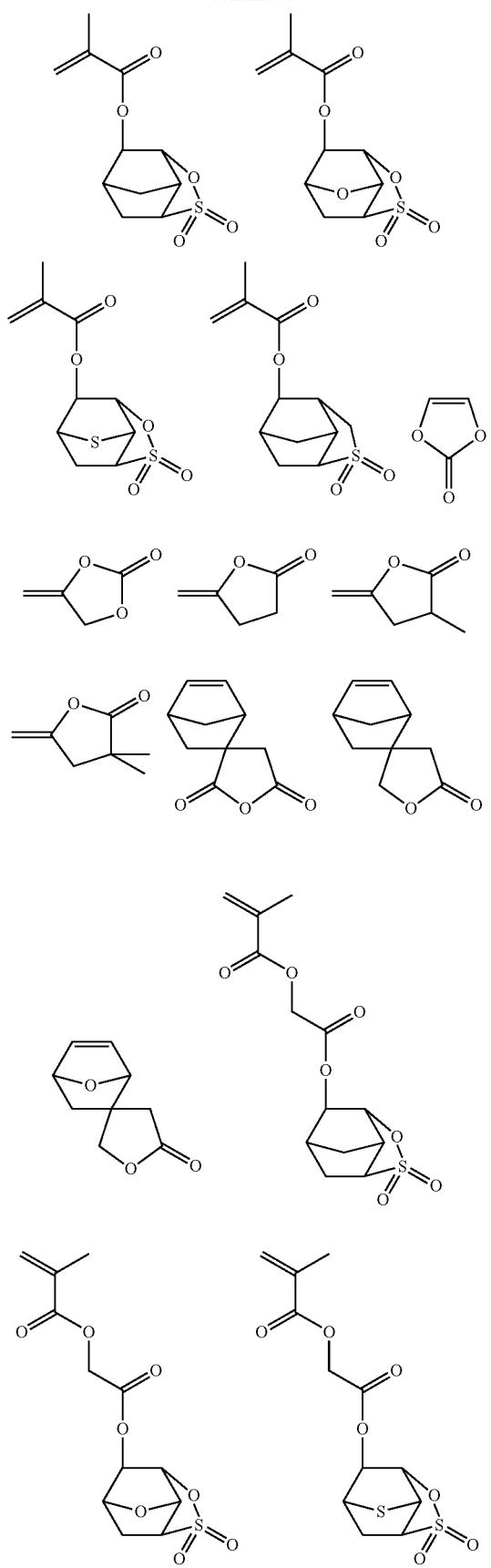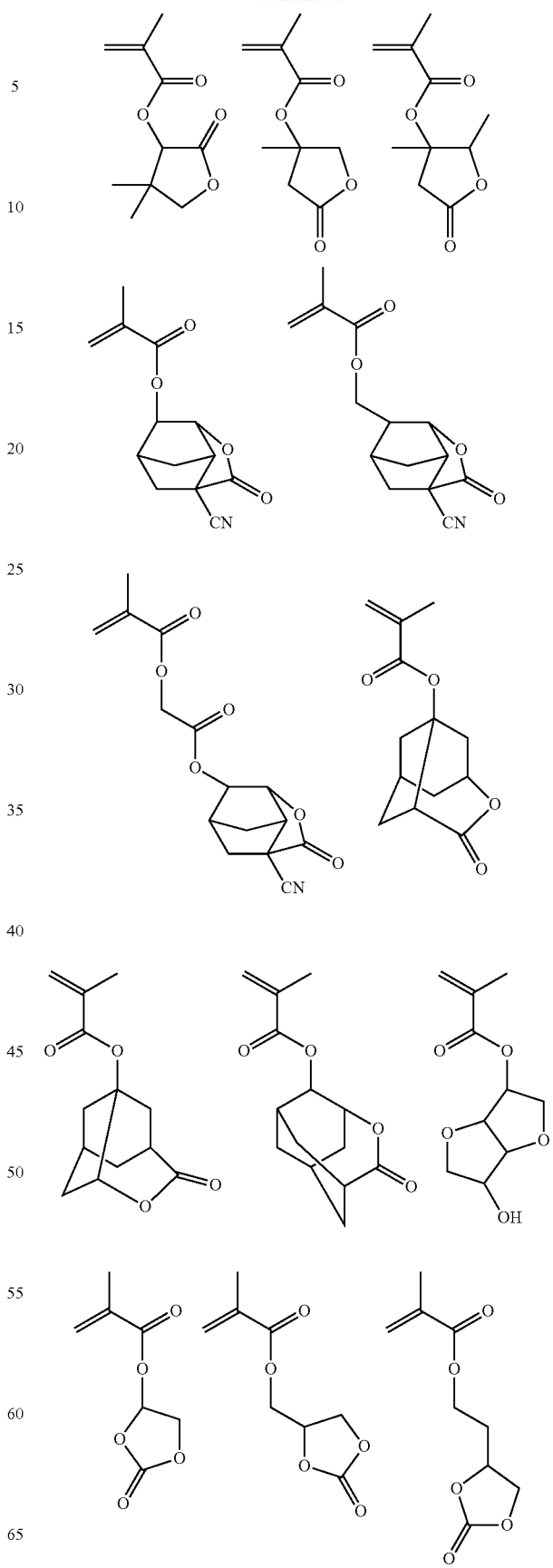

-continued
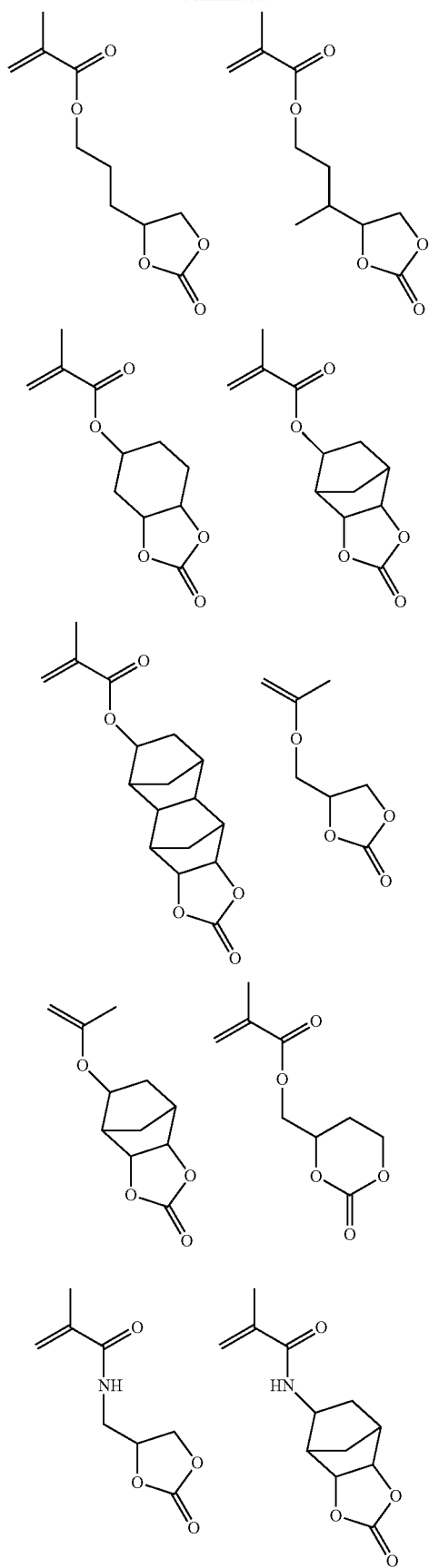
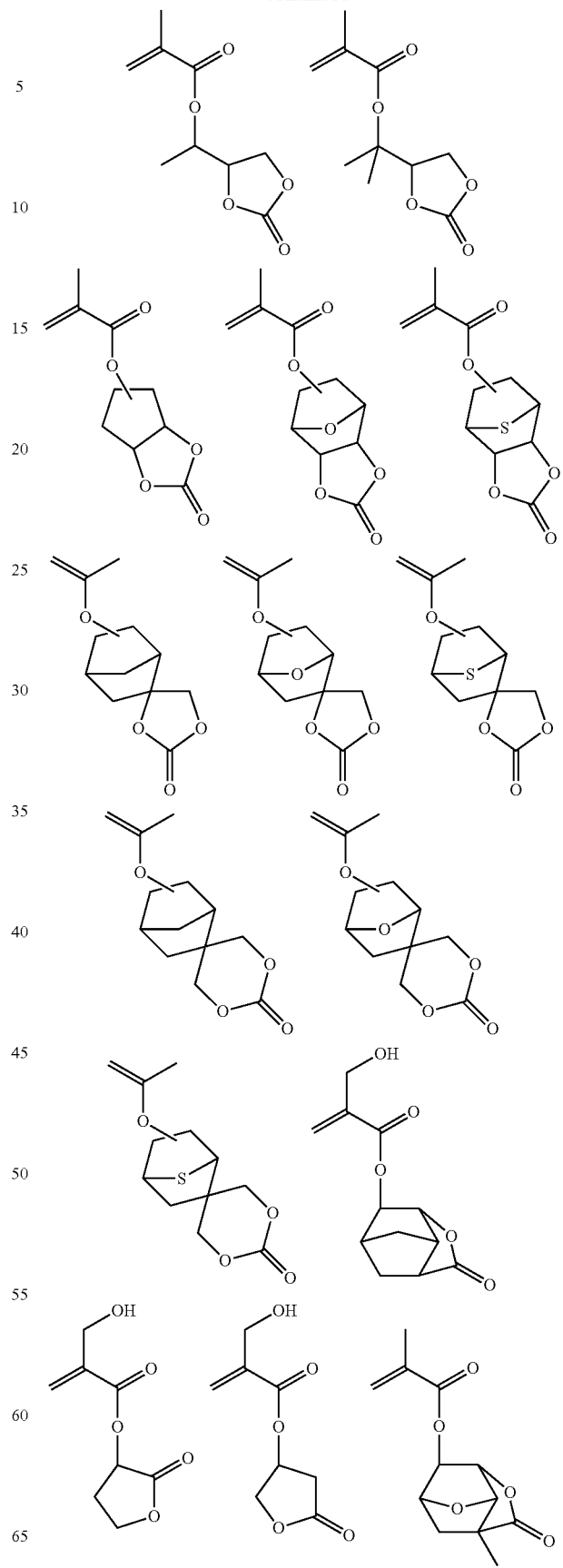

-continued
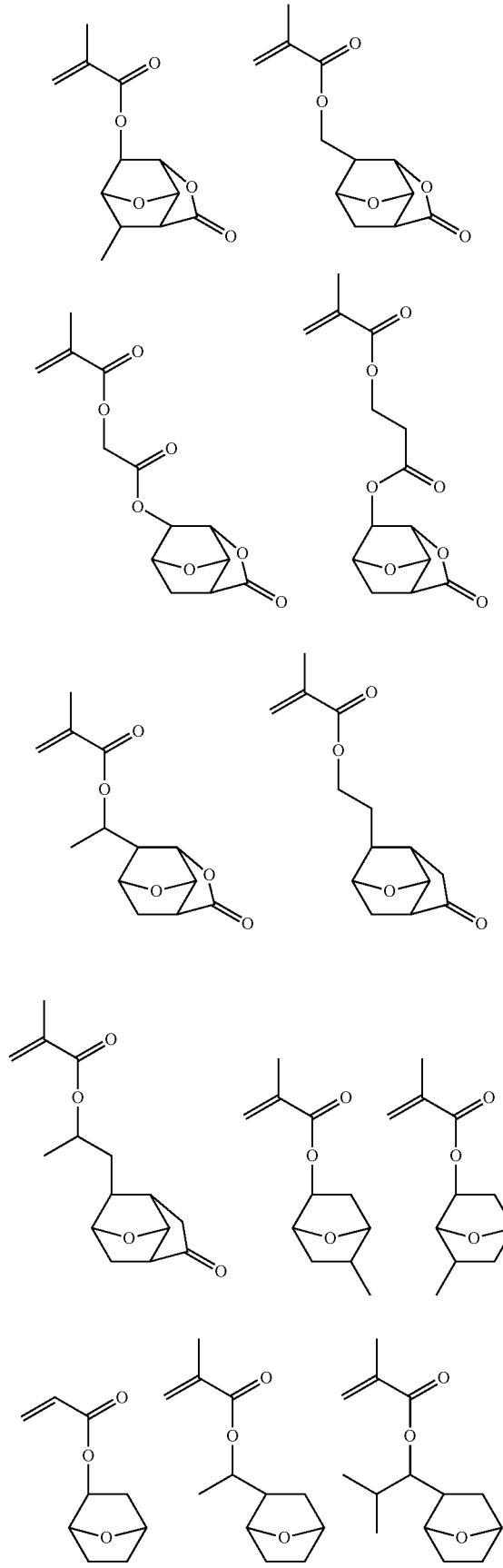
-continued
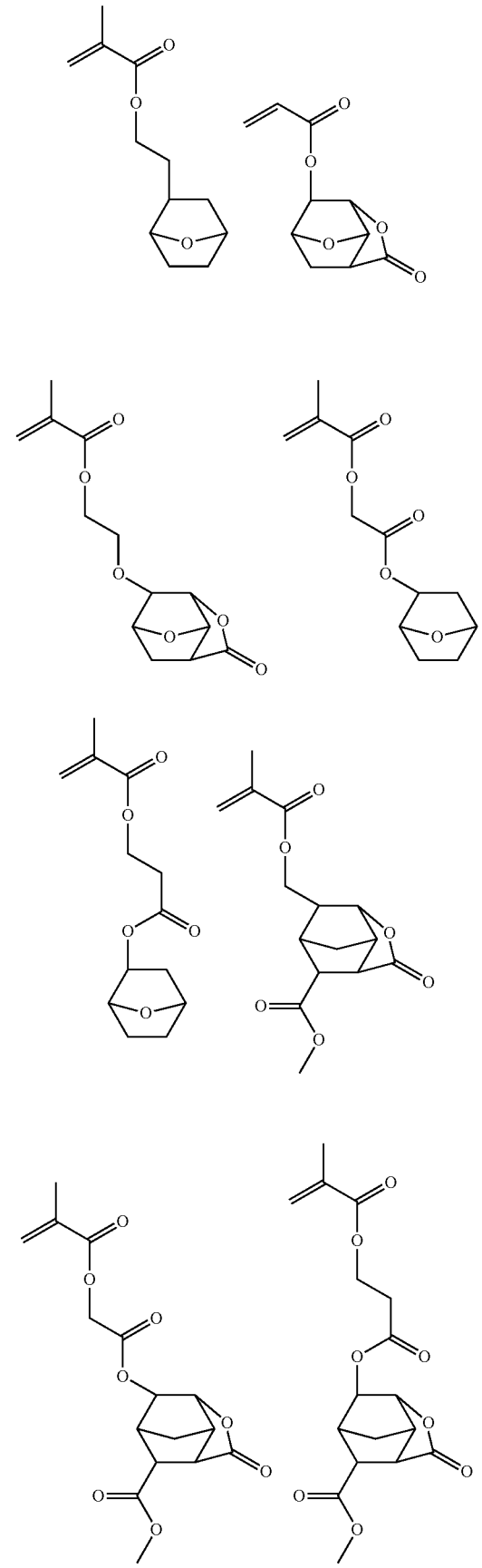

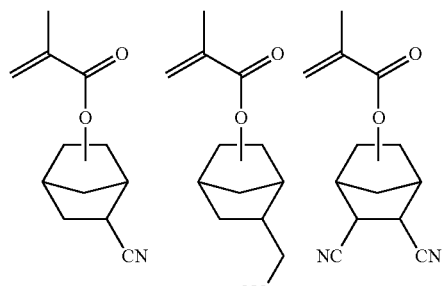
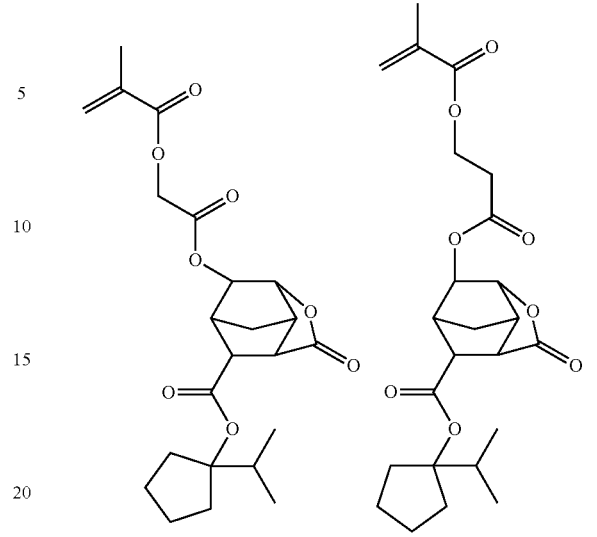
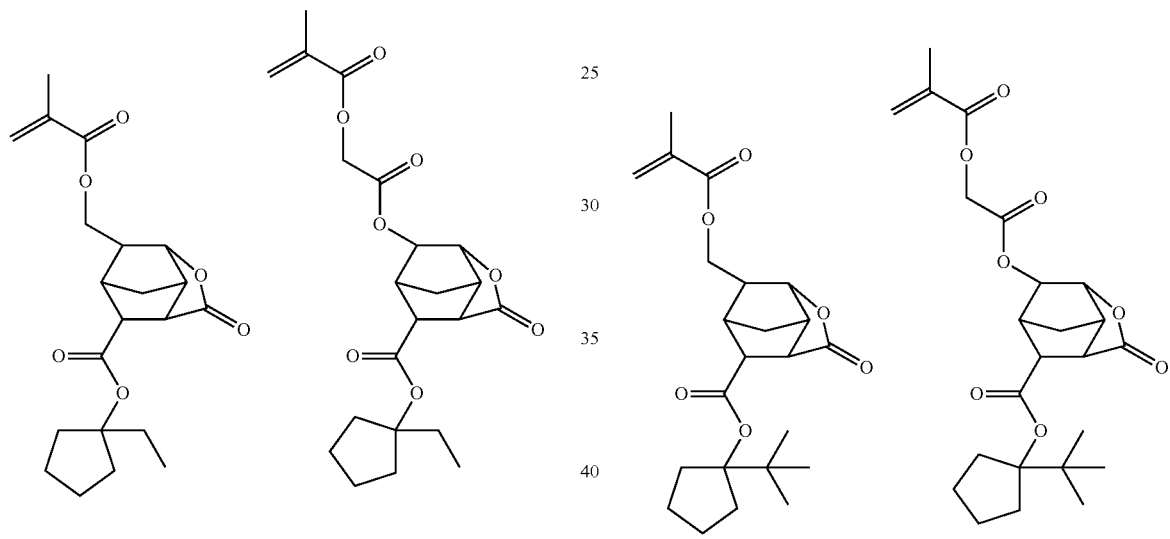
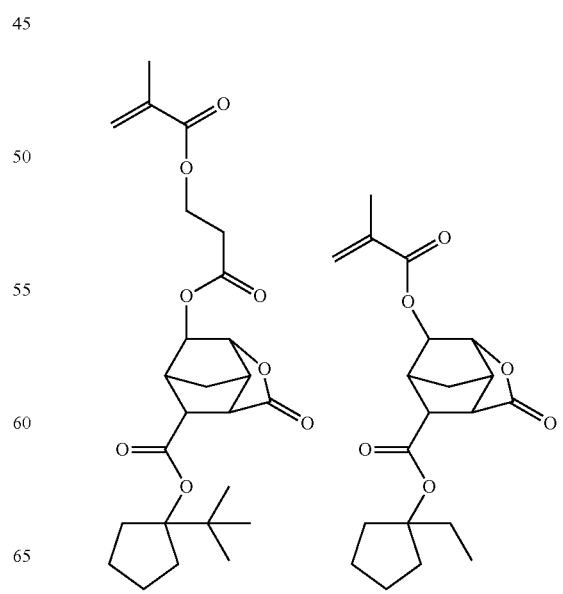

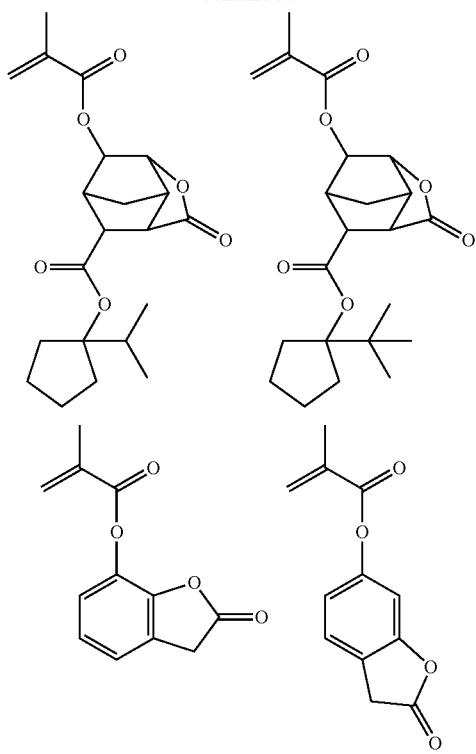
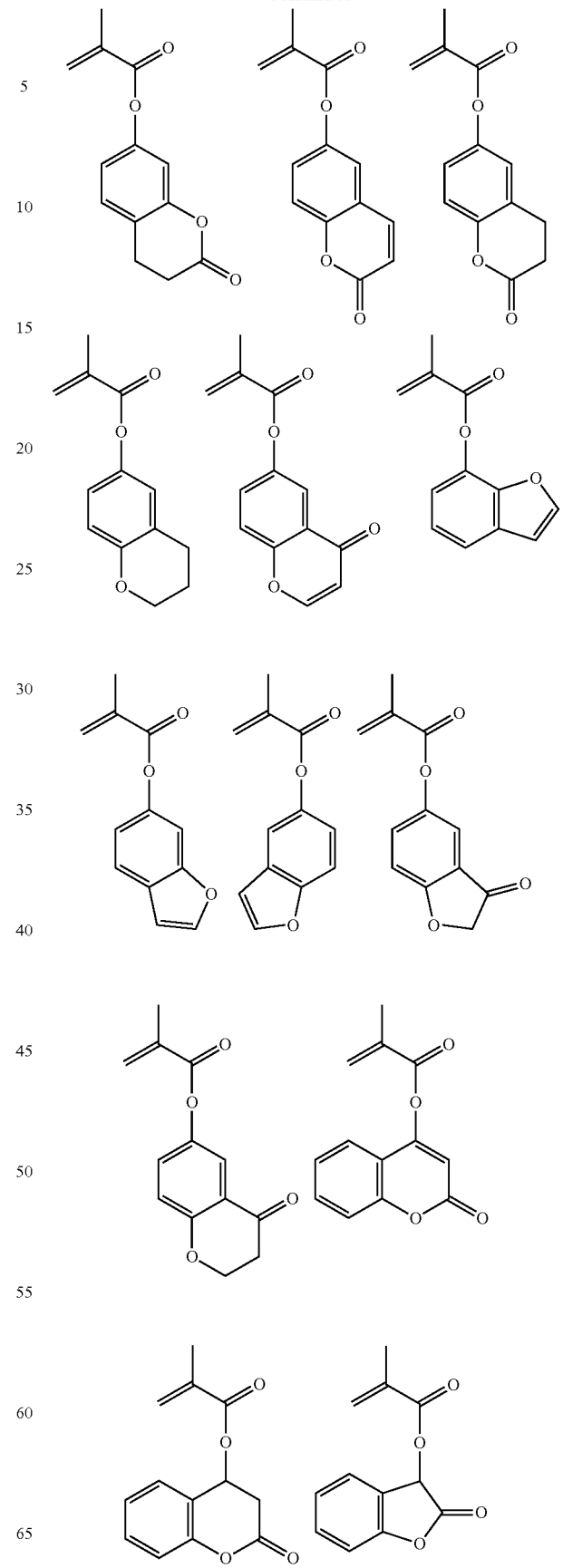

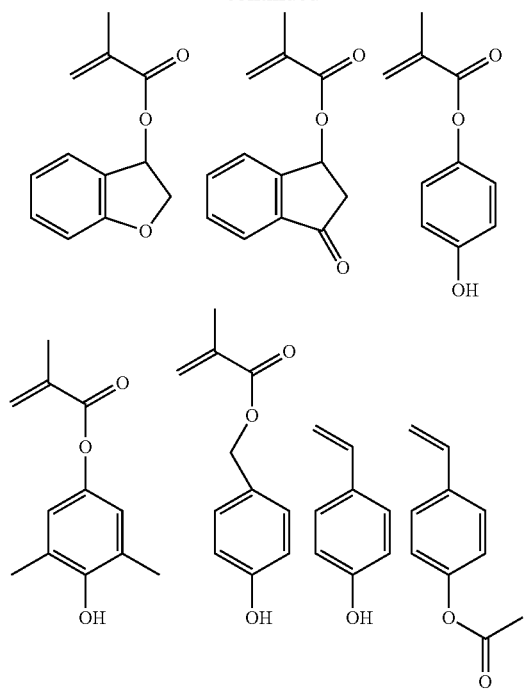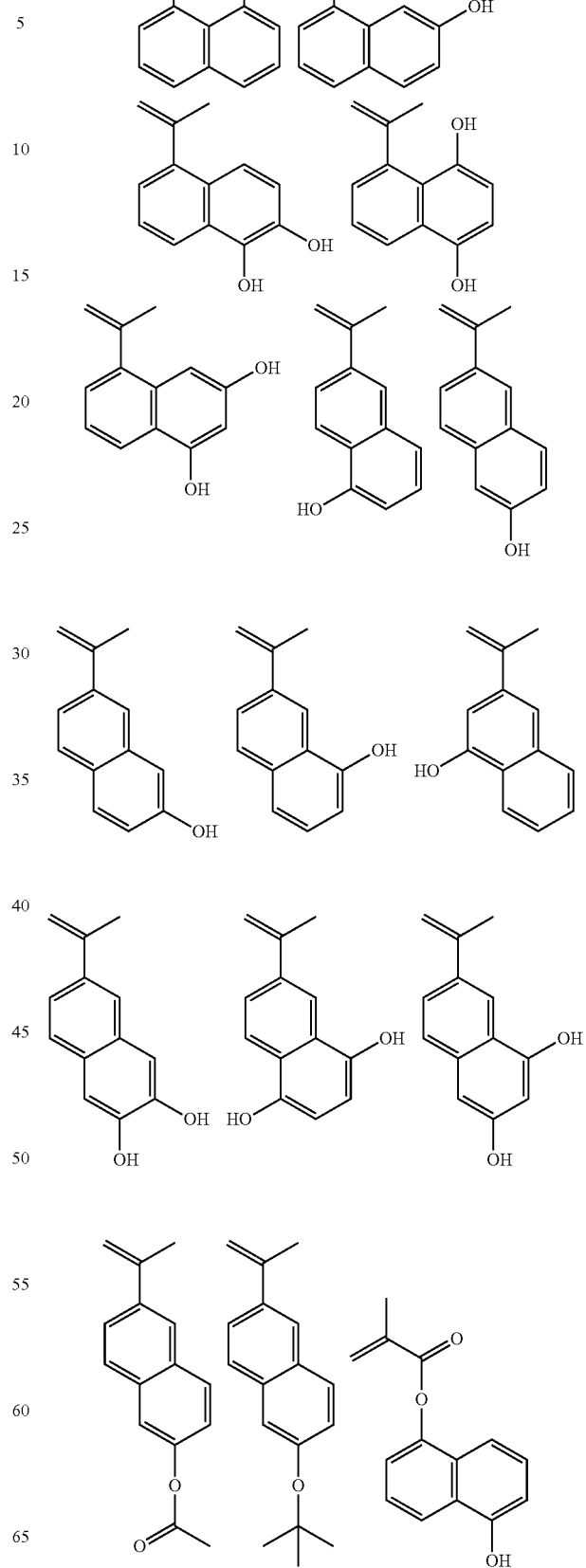

71
-continued
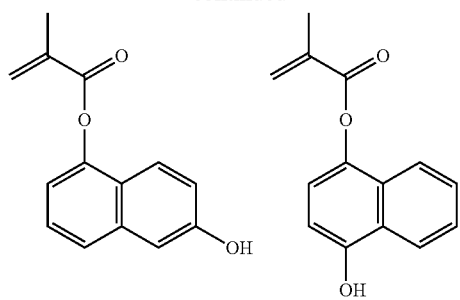 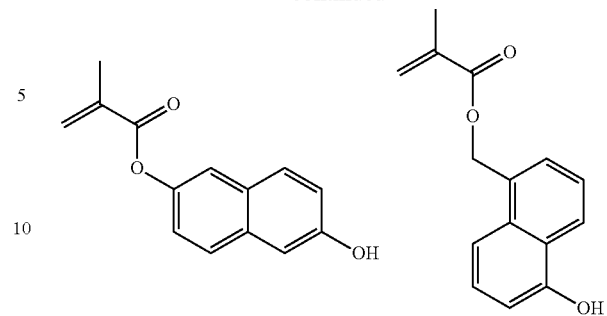
72
-continued
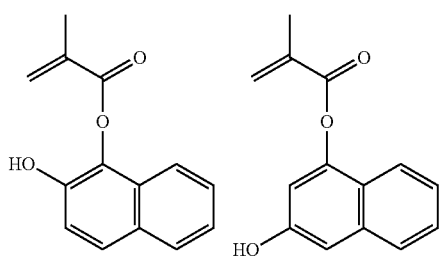 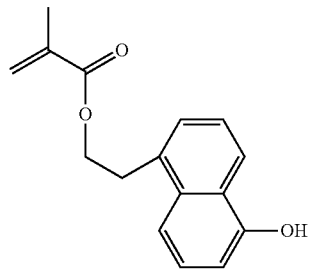
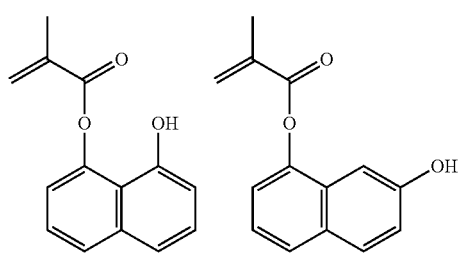 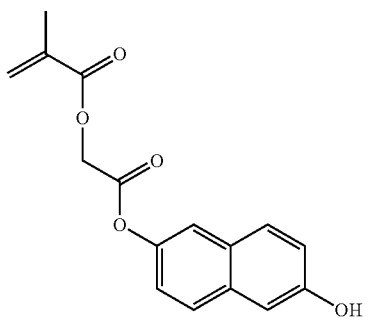
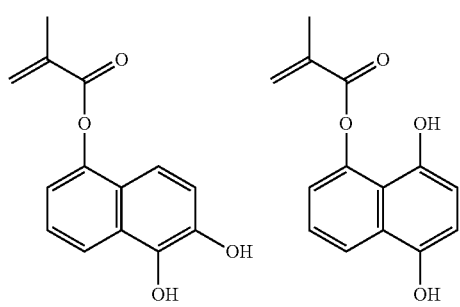 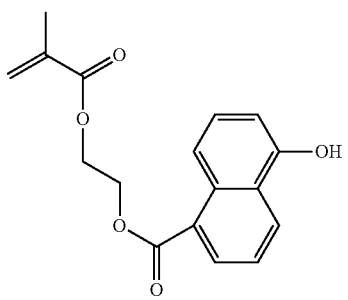
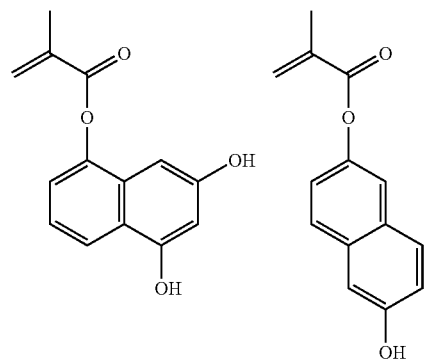 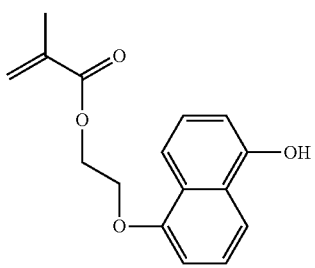

73
-continued
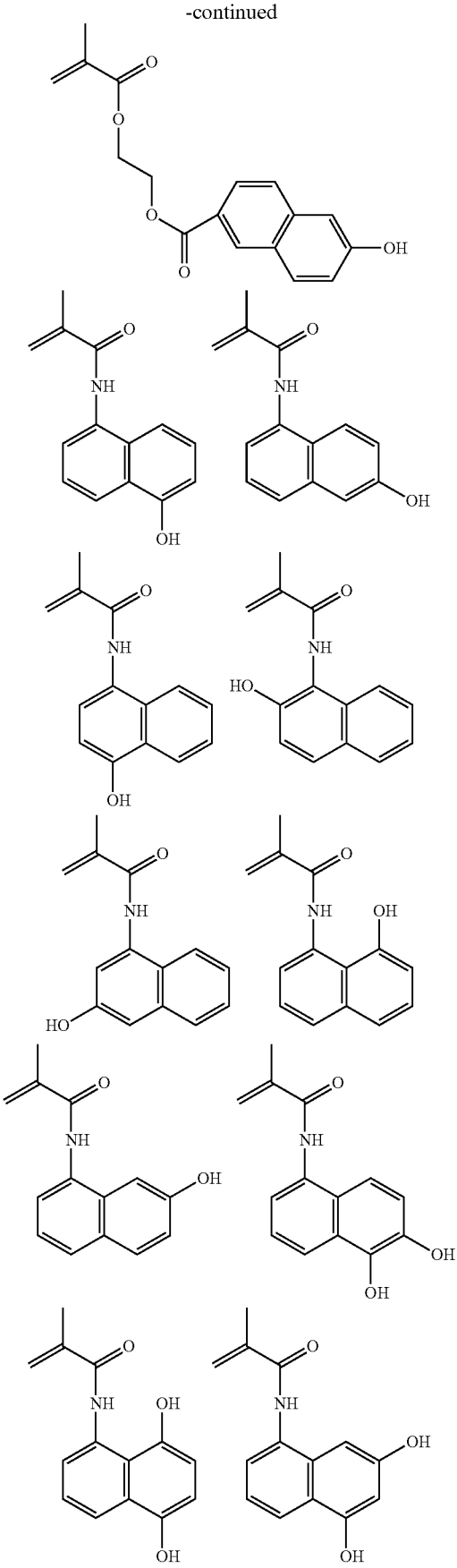
74
-continued
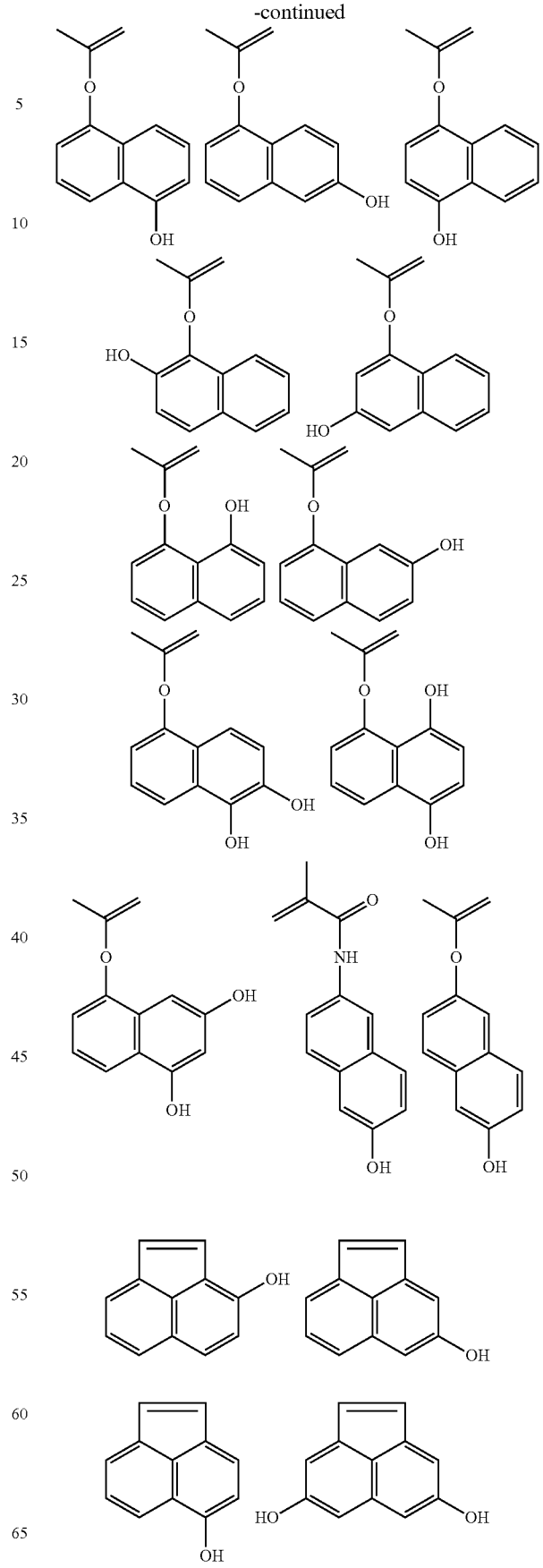

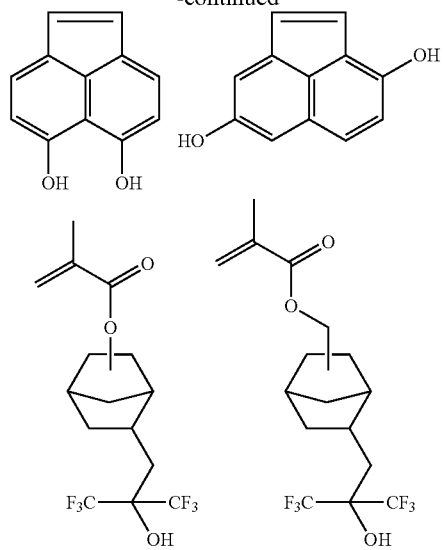
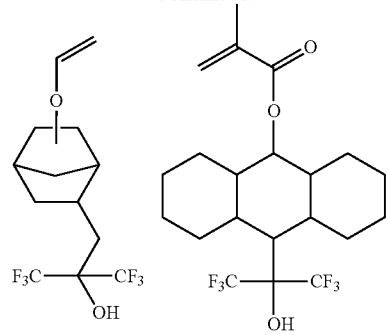
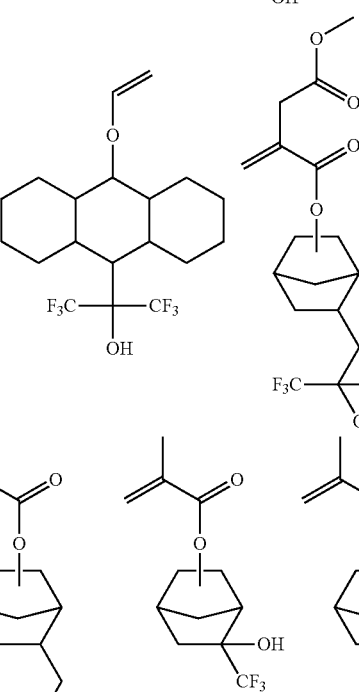
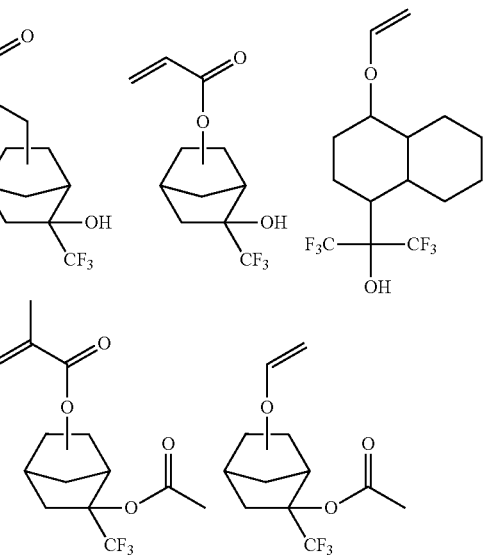

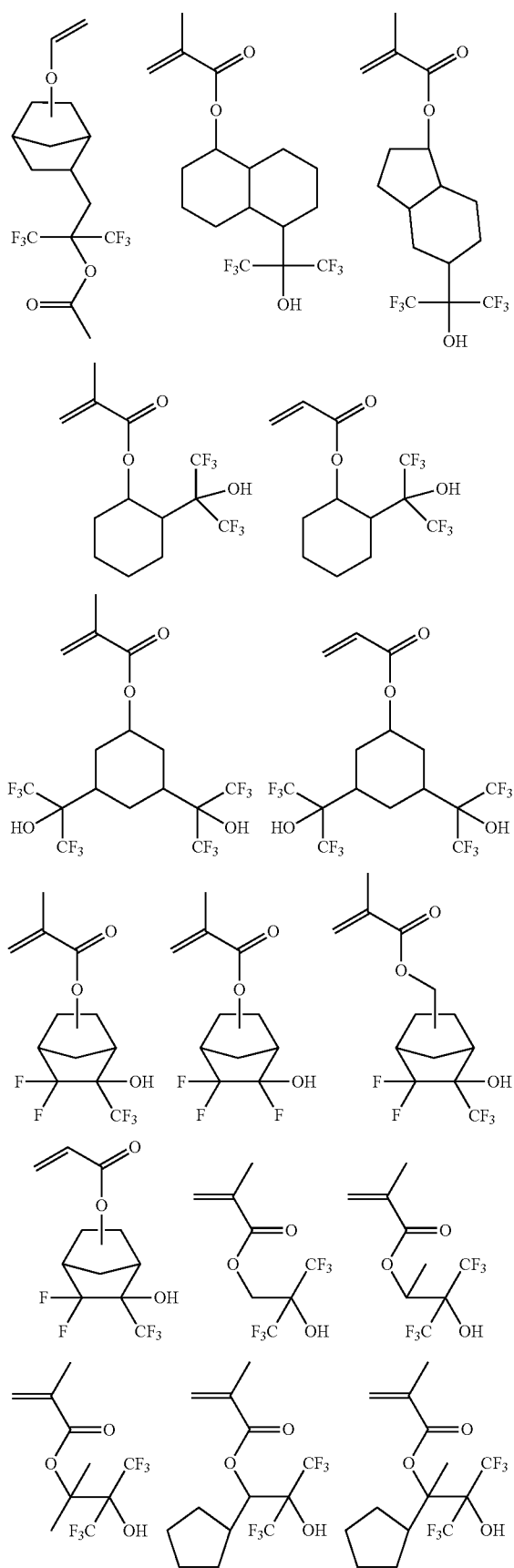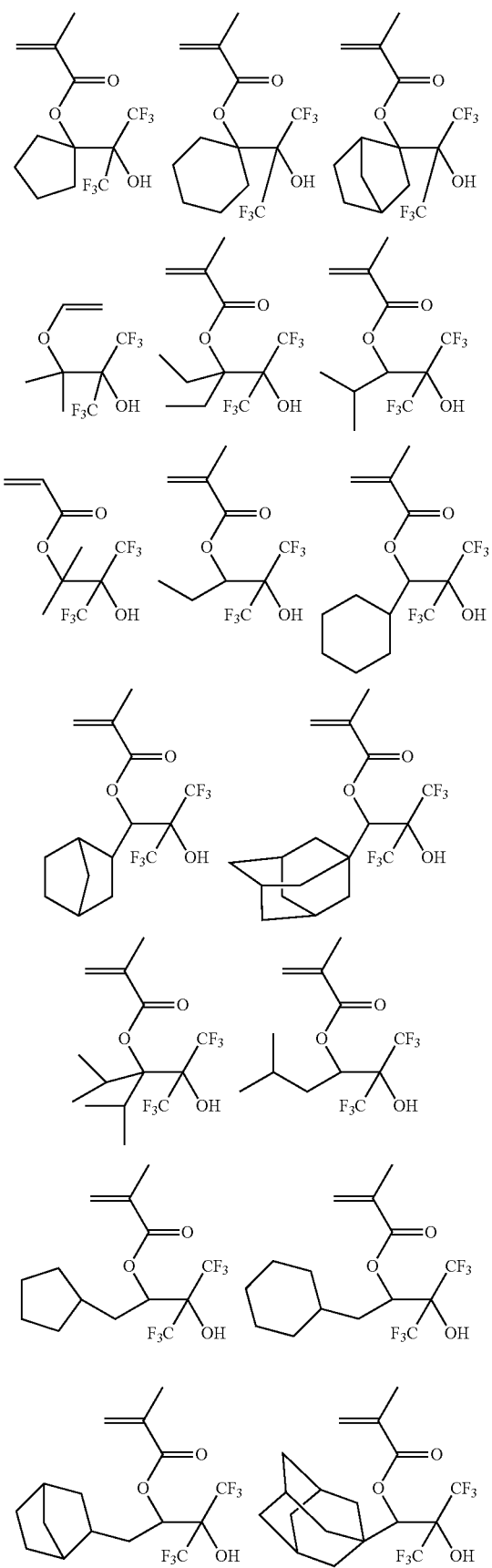

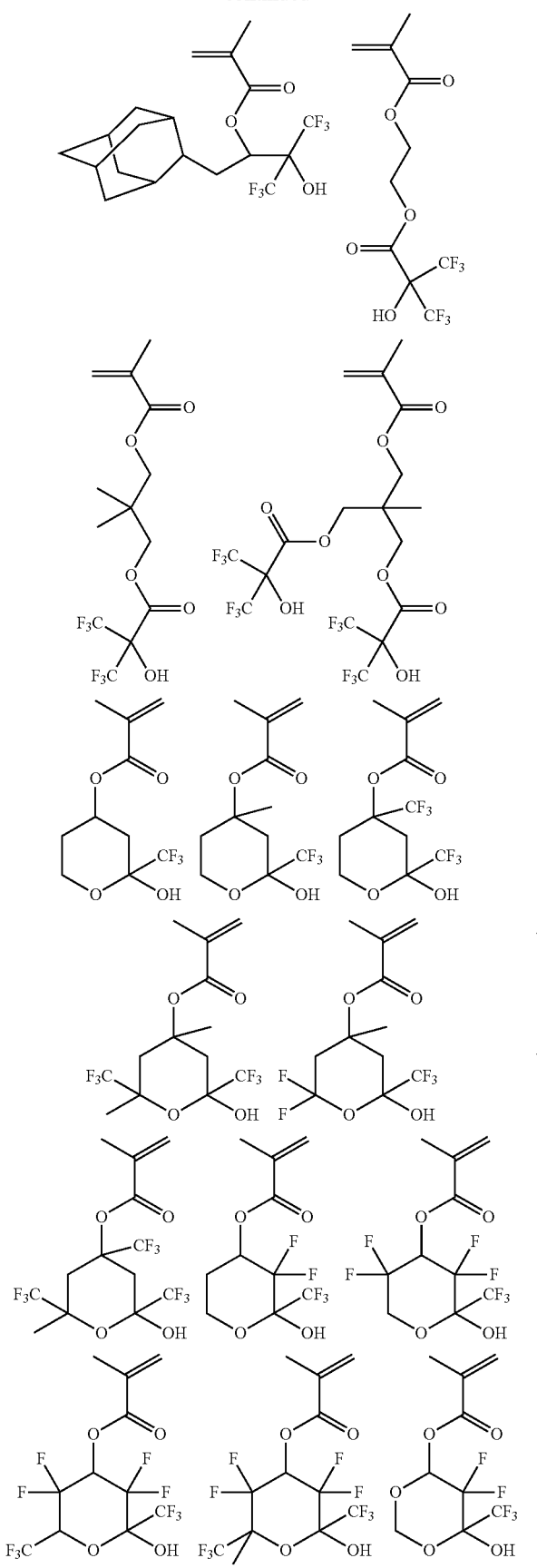
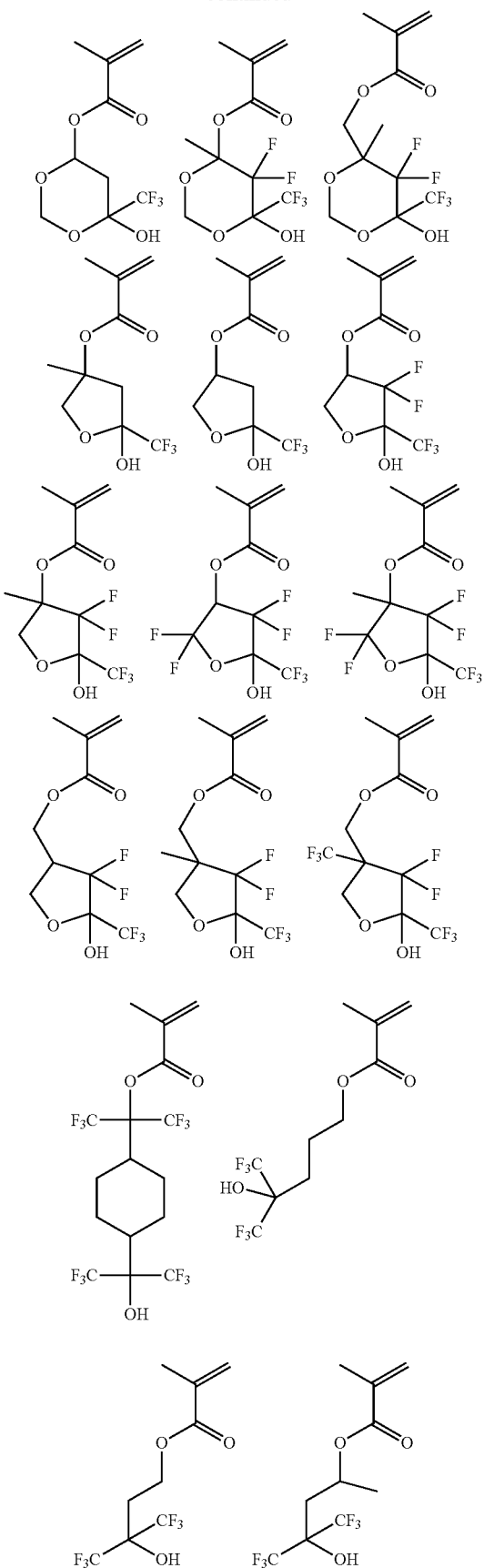

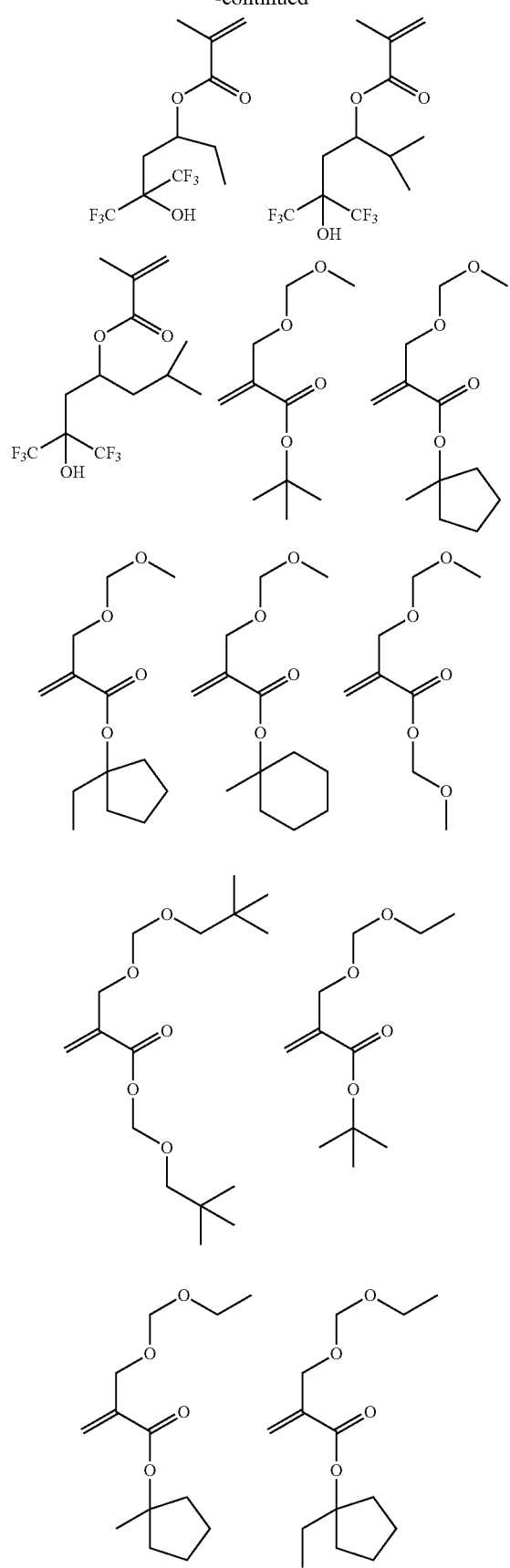
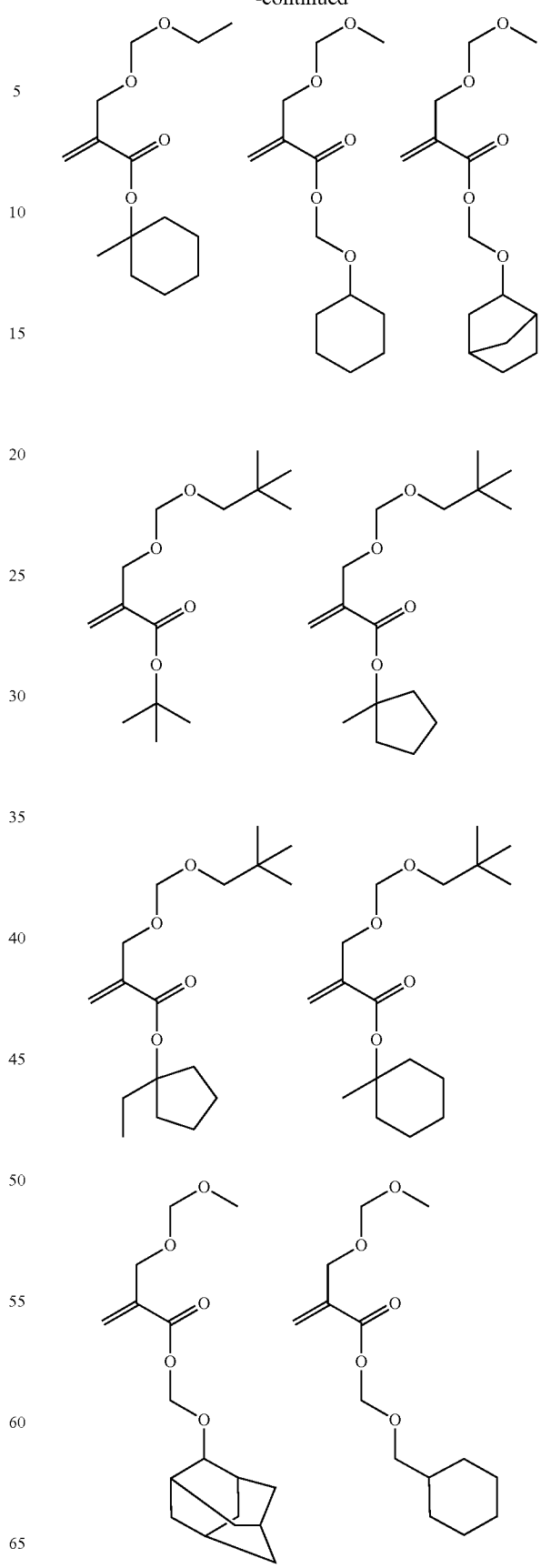

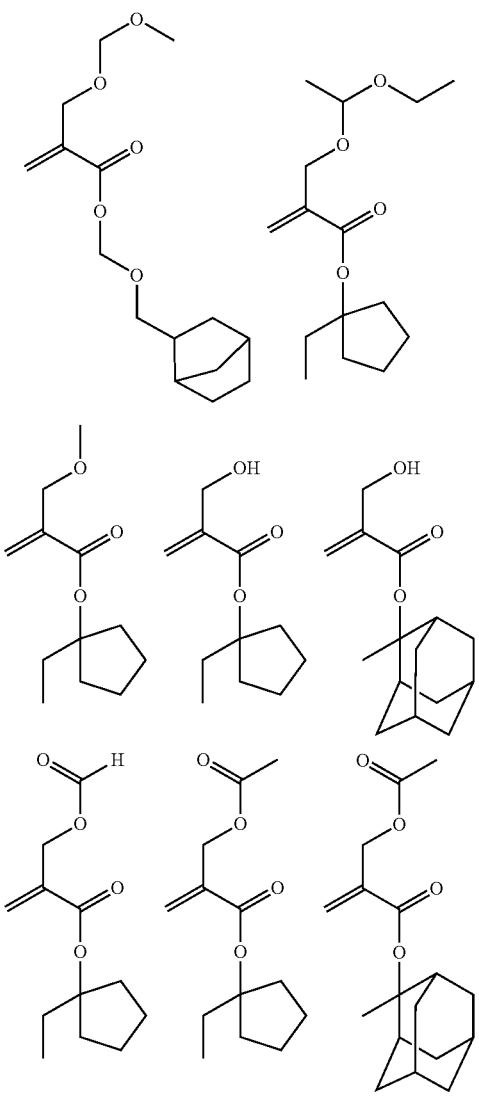

In a preferred embodiment, the polymer has further copolymerized therein units selected from sulfonium salts (D1) to (D3) represented by the general formulae below.

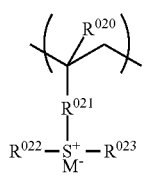
(D1)

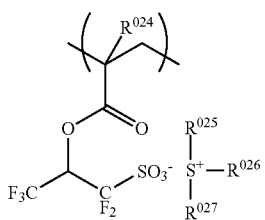
(D2)

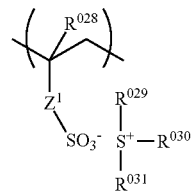
(D3)

Herein $R^{020}$, $R^{024}$ and $R^{028}$ each are hydrogen or methyl. $R^{021}$ is a single bond, phenylene, —O—$R^{033}$—, or —C(=O)—Y—$R^{033}$— wherein Y is oxygen or NH, and $R^{033}$ is a straight, branched or cyclic $C_1$-$C_6$ alkylene group, alkenylene group or phenylene group, which may contain a carbonyl (—CO—), ester (—COO—), ether (—O—) or hydroxyl radical. $R^{022}$, $R^{023}$, $R^{025}$, $R^{026}$, $R^{027}$, $R^{029}$, $R^{030}$, and $R^{031}$ are each independently a straight, branched or cyclic $C_1$-$C_{12}$ alkyl group which may contain a carbonyl, ester or ether radical, or a $C_6$-$C_{12}$ aryl, $C_7$-$C_{20}$ aralkyl, or thiophenyl group. $Z^1$ is a single bond, methylene, ethylene, phenylene, fluorophenylene, —O—$R^{032}$—, or —C(=O)—$Z^2$—$R^{032}$— wherein $Z^2$ is oxygen or NH, and $R^{032}$ is a straight, branched or cyclic $C_1$-$C_6$ alkylene group, alkenylene group or phenylene group, which may contain a carbonyl, ester, ether or hydroxyl radical. $M^-$ is a non-nucleophilic counter ion.

Besides the recurring units described above, the polymer may have further copolymerized therein additional recurring units, for example, recurring units (E1) having a non-leaving hydrocarbon group as described in JP-A 2008-281980. Examples of the non-leaving hydrocarbon group other than those described in JP-A 2008-281980 include indene, acenaphthylene, and norbornadiene derivatives. Copolymerization of recurring units (E1) having a non-leaving hydrocarbon group is effective for improving the dissolution of the polymer in organic solvent-based developer.

It is also possible to incorporate recurring units (F1) having an oxirane or oxetane ring into the polymer. Where recurring units (F1) having an oxirane or oxetane ring are copolymerized in the polymer, the exposed region of resist film will be crosslinked, leading to improvements in film retention of the exposed region and etch resistance. Examples of the recurring units (F1) having an oxirane or oxetane ring are given below wherein $R^{41}$ is hydrogen or methyl.

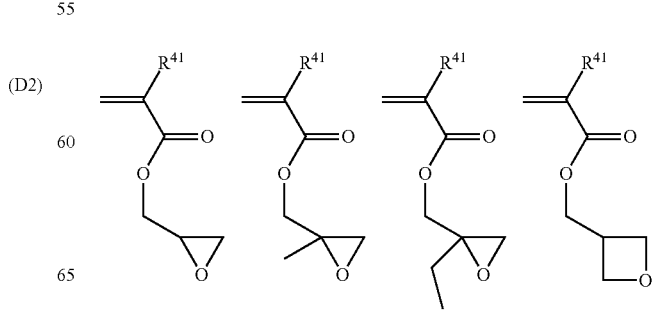

-continued
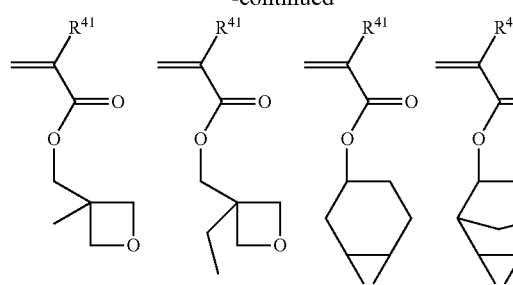
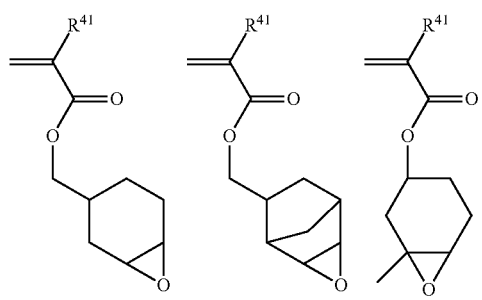
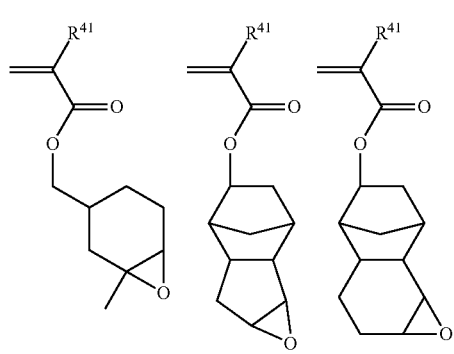
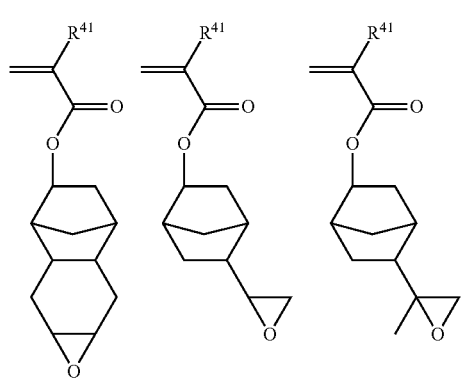
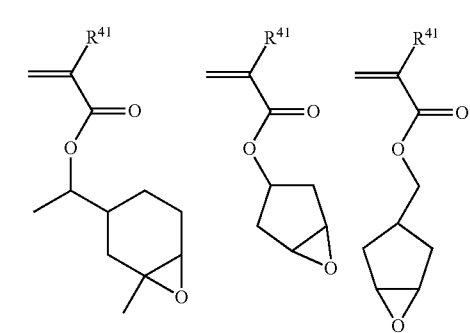
-continued
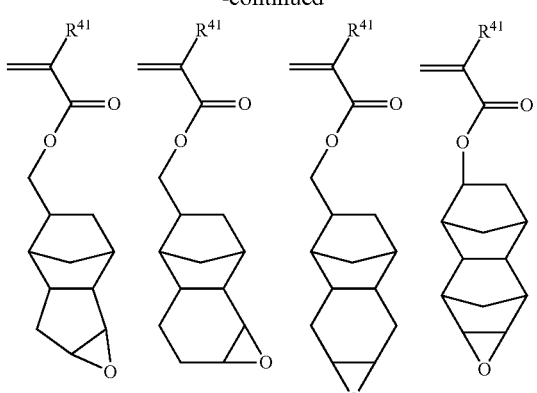
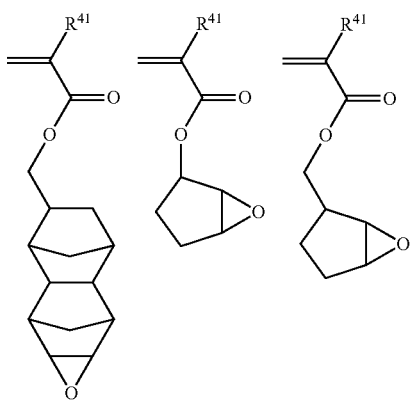
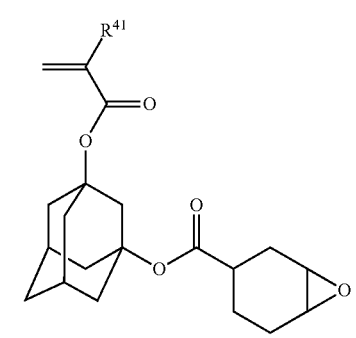
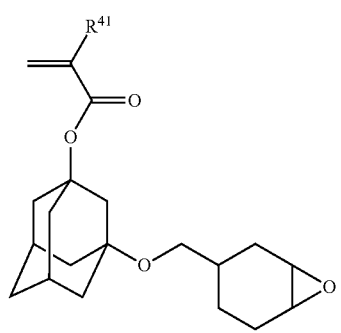

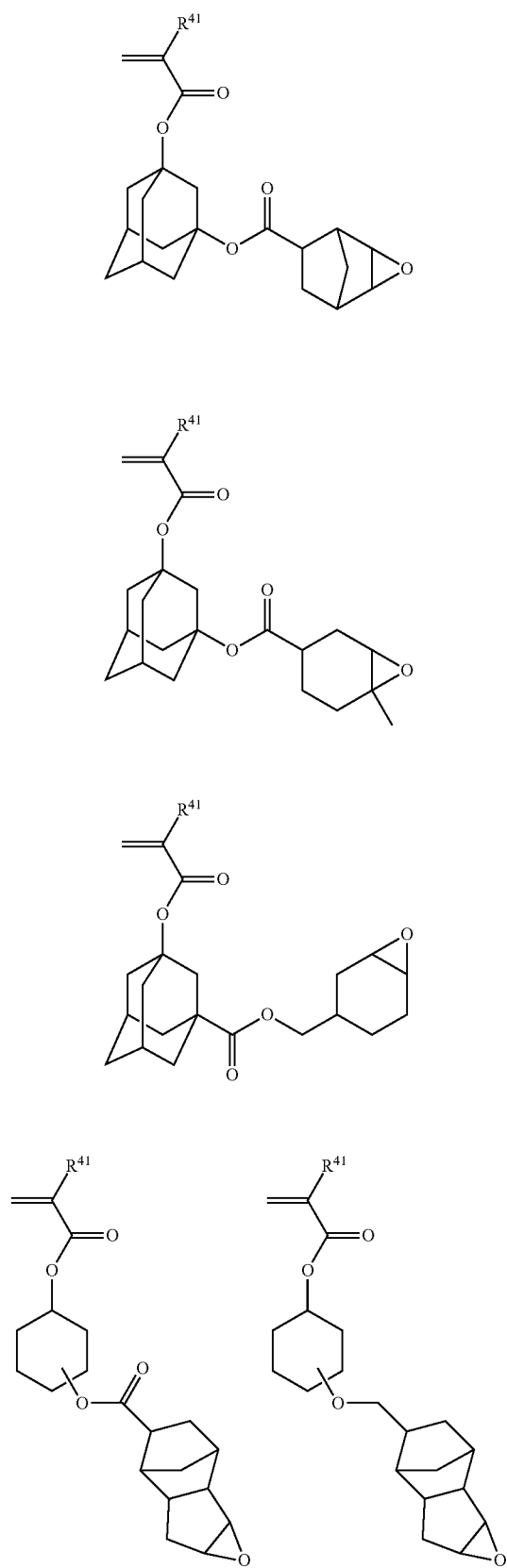

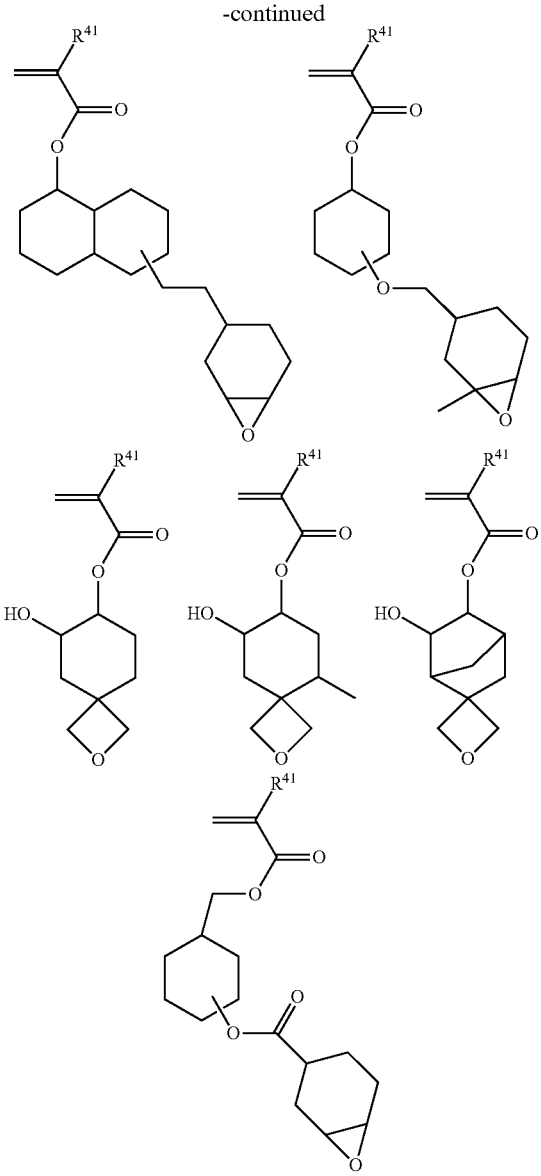

Herein, Ua1 indicates the total moles of the monomer corresponding to recurring unit (A1), Ua2 indicates the total moles of the monomer corresponding to recurring unit (A2), Ub1, Ub2, Ub3 and Ub4 indicate the total moles of the monomers corresponding to recurring units (B1) to (B4), respectively, Uc1 indicates the total moles of the monomer corresponding to recurring unit (C1), Ud1, Ud2, and Ud3 indicate the total moles of the monomers corresponding to recurring units (D1) to (D3), respectively, Ue1 indicates the total moles of the monomer corresponding to recurring unit (E1), Uf1 indicates the total moles of the monomer corresponding to recurring unit (F1), and Ua1+Ua2+Ub1+Ub2+Ub3+Ub4+Uc1+Ud1+Ud2+Ud3+Ue1+Uf1=1. Appropriate proportions of individual recurring units are in the range: 0<Ua1<1.0, 0≤Ua2<1.0, 0≤Ub1<1.0, 0≤Ub2<1.0, 0≤Ub3<1.0, 0≤Ub4<1.0, 0<Uc1<1.0, 0≤Ud1<0.2, 0≤Ud2<0.2, 0≤Ud3<0.2, 0≤Ud1+Ud2+Ud3≤0.2, 0≤Ue1≤0.4, and 0≤Uf1≤0.6; preferably 0.1≤Ua1≤0.9, 0≤Ua2≤0.9, 0.1≤Ua1+Ua2≤0.9, 0≤Ub1≤0.9, 0≤Ub2≤0.9, 0≤Ub3≤0.9, 0≤Ub4≤0.9, 0.1≤Uc1≤0.9, 0≤Ud1≤0.18, 0≤Ud2≤0.18, 0≤Ud3≤0.18, 0≤Ud1+Ud2+Ud3≤0.18, 0≤Ue1≤0.3, and 0≤Uf1≤0.5.

The polymer serving as the base resin in the resist composition used in the pattern forming process of the invention should preferably have a weight average molecular weight (Mw) in the range of 1,000 to 500,000, and more preferably 2,000 to 30,000, as measured by GPC versus polystyrene standards using tetrahydrofuran solvent. With too low a Mw, a film thickness loss is likely to occur upon organic solvent development. A polymer with too high a Mw may lose solubility in organic solvent and have a likelihood of footing after pattern formation.

If a polymer has a wide molecular weight distribution or dispersity (Mw/Mn), which indicates the presence of lower and higher molecular weight polymer fractions, there is a possibility that following exposure, foreign matter is left on the pattern or the pattern profile is exacerbated. The influences of molecular weight and dispersity become stronger as the pattern rule becomes finer. Therefore, the multi-component copolymer should preferably have a narrow dispersity (Mw/Mn) of 1.0 to 2.0, especially 1.0 to 1.5, in order to provide a resist composition suitable for micropatterning to a small feature size.

The polymer used herein may be synthesized by any desired method, for example, by dissolving unsaturated bond-containing monomers corresponding to the respective units (A1), (A2), (B1), (B2), (B3), (B4), (C1), (D1), (D2), (D3), (E1), and (F1) in an organic solvent, adding a radical initiator thereto, and effecting heat polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours. The acid labile group that has been incorporated in the monomers may be kept as such, or the product may be protected or partially protected after polymerization.

It is acceptable to use a blend of two or more polymers which differ in compositional ratio, molecular weight or dispersity as well as a blend of an inventive polymer and another polymer free of an acid labile group-substituted carboxyl group as represented by formula (1) or a blend of an inventive polymer and a polymer comprising recurring units having a conventional acid labile group-substituted hydroxyl or carboxyl group, for example, a polymer comprising recurring units (A2) and/or (B1) to (B4).

In a further embodiment, the inventive polymer may be blended with a polymer of the conventional type wherein the exposed region is dissolved on alkaline development such as (meth)acrylate polymer, polynorbornene, cycloolefin-maleic anhydride copolymer, or ring-opening metathesis polymerization (ROMP) polymer. Also, the inventive polymer may be blended with a (meth)acrylate polymer, polynorbornene, or cycloolefin-maleic anhydride copolymer having an acid labile group-substituted hydroxyl group wherein the exposed region is not dissolved by alkaline development, but a negative pattern is formed by organic solvent development.

Resist Composition

The resist composition used in the pattern forming process of the invention may further comprise an organic solvent, a compound capable of generating an acid in response to high-energy radiation (known as "acid generator"), and optionally, a dissolution regulator, basic compound, surfactant, acetylene alcohol, and other components.

The resist composition used herein may include an acid generator in order for the composition to function as a chemically amplified resist composition. Typical of the acid generator used herein is a photoacid generator (PAG) capable of generating an acid in response to actinic light or radiation. The PAG may preferably be compounded in an amount of 0.5 to 30 parts and more preferably 1 to 20 parts by weight per 100 parts by weight of the base resin. The PAG is any compound, capable of generating an acid upon exposure to high-energy radiation. Suitable PAGs include sulfonium salts, iodonium salts, sulfonyldiazomethane, N-sulfonyloxyimide, and oxime-O-sulfonate acid generators. The PAGs may be used alone or in admixture of two or more. Typically acid generators generate such acids as sulfonic acids, imide acids and methide acids. Of these, sulfonic acids which are fluorinated at $\alpha$-position are most commonly used. In case the acid labile group is an acetal group which is susceptible to deprotection, the sulfonic acid need not necessarily be fluorinated at $\alpha$-position. In the embodiment wherein the base polymer has recurring units (D1), (D2) or (D3) of acid generator copolymerized therein, the acid generator need not be separately added.

Examples of the organic solvent used herein are described in JP-A 2008-111103, paragraphs [0144] to [0145] (U.S. Pat. No. 7,537,380). Specifically, exemplary solvents include ketones such as cyclohexanone and methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as $\gamma$-butyrolactone, and mixtures thereof. Where the acid labile group used is of acetal type, a high-boiling alcohol solvent may be added for accelerating deprotection reaction of acetal, for example, diethylene glycol, propylene glycol, glycerol, 1,4-butane diol, and 1,3-butane diol.

To the resist composition, basic compounds such as amines may be added. Exemplary basic compounds include primary, secondary and tertiary amine compounds, specifically amine compounds having a hydroxyl, ether, ester, lactone, cyano or sulfonic acid ester group, as described in JP-A 2008-111103, paragraphs [0146] to [0164], and compounds having a carbamate group, as described in JP 3790649. Onium salts such as sulfonium salts, iodonium salts and ammonium salts of sulfonic acids which are not fluorinated at $\alpha$-position as described in US 20080153030 (JP-A 2008-158339) and similar onium salts of carboxylic acids as described in U.S. Pat. No. 6,136,500 (JP 3991462) may also be used as the quencher.

In case the acid labile group is an acetal group which is very sensitive to acid, the acid for eliminating the protective group need not necessarily be an $\alpha$-fluorinated sulfonic acid, imide acid or methide acid. Sometimes, deprotection reaction may take place even with $\alpha$-position non-fluorinated sulfonic acid. In this case, since an onium salt, of sulfonic acid cannot be used as the quencher, an onium salt of carboxylic acid is preferably used alone as the quencher.

Exemplary surfactants are described in JP-A 2008-111103, paragraphs [0165] to [0166]. Exemplary dissolution regulators are described in JP-A 2008-122932 (US 2008090172), paragraphs [0155] to [0178], and exemplary acetylene alcohols in paragraphs [0179] to [0182].

Also a polymeric additive may be added for improving the water repellency on surface of a resist film as spin coated. This additive may be used in the topcoatless immersion lithography. These additives have a specific structure with a 1,1,1,3,3,3-hexafluoro-2-propanol residue and are described in JP-A 2007-297590, JP-A 2008-111103 and JP-A 2012-128067. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB and avoiding any hole pattern opening failure after development. An appropriate amount of the water repellency improver is 0.1 to 20 parts, preferably 0.5 to 10 parts by weight per 100 parts by weight of the base resin.

Notably, an appropriate amount of the organic solvent is 100 to 10,000 parts, preferably 300 to 8,000 parts by weight, and an appropriate amount of the basic compound is 0.0001 to 30 parts, preferably 0.001 to 20 parts by weight, per 100 parts by weight of the base resin.

Process

The pattern forming process of the invention comprises the steps of coating a resist composition onto a substrate, prebaking the resist composition to form a resist film, exposing a selected region of the resist film to high-energy radiation, baking (PEB), and developing the exposed resist film in an organic solvent developer so that the unexposed region of resist film is dissolved and the exposed region of resist film is left, thereby forming a negative tone resist pattern such as a hole or trench pattern.

FIG. 1 illustrates the pattern forming process of the invention. First, the resist composition is coated on a substrate to form a resist film thereon. Specifically, a resist film 40 of a resist composition is formed on a processable substrate 20 disposed on a substrate 10 directly or via an intermediate intervening layer 30 as shown in FIG. 1A. The resist film preferably has a thickness of 10 to 1,000 nm and more preferably 20 to 500 nm. Prior to exposure, the resist film is heated or prebaked, preferably at a temperature of 60 to 180° C., especially 70 to 150° C. for a time of 10 to 300 seconds, especially 15 to 200 seconds.

The substrate 10 used herein is generally a silicon substrate. The processable substrate (or target film) 20 used herein includes $SiO_2$, SiN, SiON, SiOC, p-Si, $\alpha$-Si, TiN, WSi, BPSG, SOG, Cr, CrO, CrON, MoSi, low dielectric film, and etch stopper film. The intermediate intervening layer 30 includes hard masks of $SiO_2$, SiN, SiON or p-Si, an undercoat in the form of carbon film, a silicon-containing intermediate film, and an organic antireflective coating.

Figure 1B:
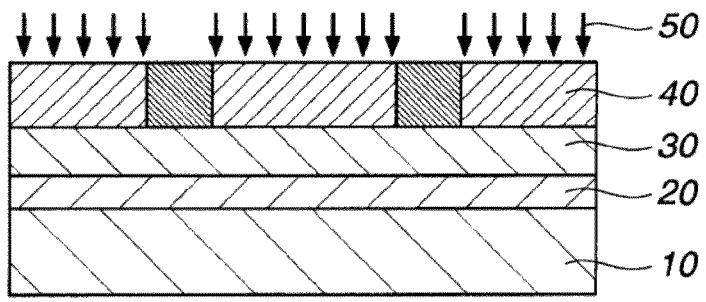
FIG. 1B shows the resist film being exposed.

Next comes exposure depicted at 50 in FIG. 1B. For the exposure, preference is given to high-energy radiation having a wavelength of 140 to 250 nm, EUV having a wavelength of 13.5 nm, and EB, and especially ArF excimer laser radiation of 193 nm. The exposure may be done either in a dry atmosphere such as air or nitrogen stream or by immersion lithography in water. The ArF immersion lithography uses deionized water or liquids having a refractive index of at least 1 and highly transparent to the exposure wavelength such as alkanes as the immersion solvent. The immersion lithography involves prebaking a resist film and exposing the resist film to light through a projection lens, with water introduced between the resist film and the projection lens. Since this allows lenses to be designed to a MA of 1.0 or higher, formation of finer feature size patterns is possible. The immersion lithography is important for the ArF lithography to survive to the 45-nm node. In the case of immersion lithography, deionized water rinsing (or post-soaking) may be carried out after exposure for removing water droplets left on the resist film, or a protective film may be applied onto the resist film after pre-baking for preventing any leach-out from the resist film and improving water slip on the film surface.

The resist protective film used in the immersion lithography is preferably formed from a solution of a polymer having 1,1,1,3,3,3-hexafluoro-2-propanol residues which is insoluble in water, but soluble in an alkaline developer liquid, in a solvent selected from alcohols of at least 4 carbon atoms, ethers of 8 to 12 carbon atoms, and mixtures thereof. The protective film-forming composition used herein may be based on a polymer comprising recurring units derived from a monomer having a 1,1,1,3,3,3-hexafluoro-2-propanol residue. While the protective film must dissolve in the organic solvent developer, the polymer comprising recurring units derived from a monomer having a 1,1,1,3,3,3-hexafluoro-2-propanol residue dissolves in organic solvent developers. In particular, protective film-forming materials having 1,1,1,3,3,3-hexafluoro-2-propanol residues as described in JP-A 2007-025634 and JP-A 2008-003569 readily dissolve in organic solvent developers.

In the protective film-forming composition, an amine compound or amine salt or a polymer having copolymerized therein recurring units containing an amine compound or amine salt may be used. This component is effective for controlling diffusion of the acid generated in the exposed region of the photoresist film to the unexposed region for thereby preventing any hole opening failure. Useful protective films materials having an amine compound added thereto are described in JP-A 2008-003569, and useful protective films materials having an amino group or amine salt copolymerized are described in JP-A 2007-316448. The amine compound or amine salt may be selected from the compounds enumerated as the basic compound to be added to the resist composition. An appropriate amount of the amine compound or amine salt added is 0.01 to 10 parts, preferably 0.02 to 8 parts by weight per 100 parts by weight of the base resin.

After formation of the photoresist film, deionized water rinsing (or post-soaking) may be carried out for extracting the acid generator and the like from the film surface or washing away particles, or after exposure, rinsing (or post-soaking) may be carried out for removing water droplets left on the resist film. If the acid evaporating from the exposed region during PEB deposits on the unexposed region to deprotect the protective group on the surface of the unexposed region, there is a possibility that the surface edges of holes after development are bridged to close the holes. Particularly in the case of negative development, regions surrounding the holes receive light so that acid is generated therein. There is a possibility that the holes are not opened if the acid outside the holes evaporates and deposits inside the holes during PEB. Provision of a protective film is effective for preventing evaporation of acid and for avoiding any hole opening failure. A protective film having an amine compound added thereto is more effective for preventing acid evaporation. On the other hand, a protective film to which an acid compound such as a carboxyl or sulfo group is added or which is based on a polymer having copolymerized therein monomeric units containing a carboxyl or sulfo group is undesirable because of a potential hole opening failure.

The other embodiment of the invention is a process for forming a pattern by applying a resist composition comprising a polymer comprising recurring units having formula (A1), an optional acid generator, and an organic solvent onto a substrate, baking the composition to form a resist film, forming a protective film on the resist film, exposing the resist film to high-energy radiation to define exposed and unexposed regions, baking, and applying an organic solvent-based developer to the coated substrate to form a negative pattern wherein the unexposed region of resist film and the protective film are dissolved and the exposed region of resist film is not dissolved. The protective film is preferably formed from a composition comprising a polymer bearing a 1,1,1,3,3,3-hexafluoro-2-propanol residue and an amino group or amine salt-containing compound, or a composition comprising a polymer bearing a 1,1,1,3,3,3-hexafluoro-2-propanol residue and having amino group or amine salt-containing recurring units copolymerized, the composition further comprising an alcohol solvent of at least 4 carbon atoms, an ether solvent of 8 to 12 carbon atoms, or a mixture thereof.

Examples of suitable recurring units having a 1,1,1,3,3,3-hexafluoro-2-propanol residue include those derived from hydroxyl-bearing monomers selected from among the monomers listed for units (C1) on pages 54, 55 and 56. Examples of the amino group-containing compound include the amine compounds described in JP-A 2008-111103, paragraphs [0146] to [0164] as being added to photoresist compositions. Examples of the amine salt-containing compound include salts of the foregoing amine compounds with carboxylic acids or sulfonic acids.

Suitable alcohols of at least 4 carbon atoms include 1-butyl alcohol, 2-butyl alcohol, isobutyl alcohol, tert-butyl alcohol, 1-pent and, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether solvents of 3 to 12 carbon atoms include di-n-butyl ether, diisobutyl ether, di-sec-butyl ether, di-n-pentyl ether, diisopentyl ether, di-sec-pentyl ether, di-tert-amyl ether, and di-n-hexyl ether.

Exposure is preferably performed in an exposure dose of about 1 to 200 mJ/cm$^2$, more preferably about 10 to 100 mJ/cm$^2$. This is followed by baking (PEB) on a hot plate at 60 to 150° C. for 1 to 5 minutes, preferably at 30 to 120° C. for 1 to 3 minutes.

Figure 1C:
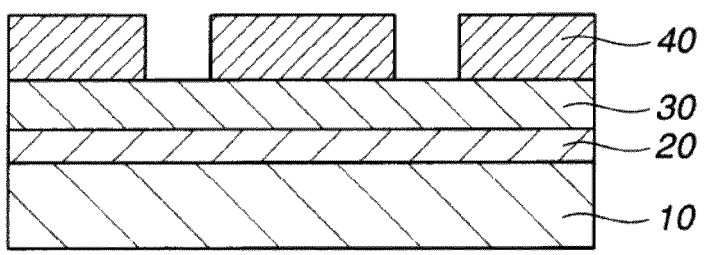
FIG. 1C shows the resist film being developed in an organic solvent.

Thereafter the exposed resist film is developed in a developer consisting of an organic solvent for 0.1 to 3 minutes, preferably 0.5 to 2 minutes by any conventional techniques such as dip, puddle and spray techniques. In this way, the unexposed region of resist film was dissolved away, leaving a negative resist pattern 40 on the substrate 10 as shown in FIG. 1C. The developer used herein is preferably selected from among ketones such as 2-octanone, 2-nonanone, 2-heptanone, 3-heptanone, 4-heptanone, 2-hexanone, 3-hexanone, diisobutyl ketone, methylcyclohexanone, acetophenone, and methylacetophenone, and esters such as propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof. One or more of these solvents may be used as the developer. When a mixture of plural solvents is used, they may be mixed in any desired ratio. A surfactant may be added to the developer while it may be selected from the same list of compounds as exemplified for the surfactant to be added to the resist composition.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-amyl ether, and di-n-hexyl ether. The solvents may be used alone or in admixture.

Besides the foregoing solvents, aromatic solvents may be used, for example, toluene, xylene, ethylbenzene, isopropylbenzene, tert-butylbenzene and mesitylene.

Rinsing is effective for minimizing the risks of resist pattern collapse and defect formation. However, rinsing is not essential. If rinsing is omitted, the amount of solvent used may be reduced.

A hole pattern after reversal may be shrunk by the RELACS® process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is at a temperature of 70 to 180° C., preferably 80 to 170° C., for a time of 10 to 300 seconds. The extra shrink agent is stripped and the hole pattern is shrunk.

Where a hole pattern is formed by negative tone development, exposure by double dipole illuminations of X- and Y-direction line patterns provides the highest contrast light. The contrast may be further increased by combining dipole illumination with s-polarized illumination.

When a halftone phase shift mask bearing a lattice-like shifter pattern is used, a pattern of holes may be formed at the intersections between gratings of the lattice-like shifter pattern after development, as described in JP-A 2011-170316, paragraph [0097] (US 20110177462). The preferred halftone phase shift mask bearing a lattice-like shifter pattern has a transmittance of 3 to 15%. More preferably, the phase shift mask used is a phase shift mask including a lattice-like first shifter having a line width equal to or less than a half pitch and a second shifter arrayed on the first shifter and consisting of lines whose on-wafer size is 2 to 30 nm thicker than the line width of the first shifter, whereby a pattern of holes is formed only where the thick shifter is arrayed. Also preferably, the phase shift mask used is a phase shift mask including a lattice-like first shifter having a line width equal to or less than a half pitch and a second shifter arrayed on the first shifter and consisting of dots whose on-wafer size is 2 to 100 nm thicker than the line width of the first shifter, whereby a pattern of holes is formed only where the thick shifter is arrayed.

Exposure by double dipole illuminations of X- and Y-direction lines combined with polarized illumination presents a method of forming light of the highest contrast. This method, however, has the drawback that the throughput is substantially reduced by double exposures and mask exchange therebetween. To continuously carry out two exposures while exchanging a mask, the exposure tool must be equipped with two mask stages although the existing exposure tool includes a single mask stage. Higher throughputs may be obtained by carrying out exposure of X direction lines continuously on 25 wafers in a front-opening unified pod (FOUP), exchanging the mask, and carrying out exposure continuously on the same 25 wafers, rather than exchanging a mask on every exposure of a single wafer. However, a problem arises that as the time duration until the first one of 25 wafers is exposed in the second exposure is prolonged, the environment affects the resist such that the resist after development may change its size and shape. To block the environmental impact on wafers in standby until the second exposure, it is effective that the resist film is overlaid with a protective film.

To proceed with a single mask, it is proposed in Non-Patent Document 1 to carry out two exposures by dipole illuminations in X and Y directions using a mask bearing a lattice-like pattern. When this method is compared with the above method using two masks, the optical contrast is somewhat reduced, but the throughput is improved by the use of a single mask. As described in Non-Patent Document 1, the method involves forming X-direction lines in a first photoresist, film by X-direction dipole illumination using a mask bearing a lattice-like pattern, insolubilizing the X-direction lines by light irradiation, coating a second photoresist, film thereon, and forming Y-direction lines by Y-direction dipole illumination, thereby forming holes at the interstices between X- and Y-direction lines. Although only a single mask is needed, this method includes additional steps of insolubilizing the first photoresist pattern between the two exposures, and coating and developing the second photoresist film. Then the wafer must be removed from the exposure stage between the two exposures, giving rise to the problem of an increased alignment error. To minimize the alignment error between two exposures, two exposures must be continuously carried out without removing the wafer from the exposure stage. The addition of s-polarized illumination to dipole illumination provides a further improved contrast and is thus preferably employed. After two exposures for forming X- and Y-direction lines using a lattice-like mask are performed in an overlapping manner, negative tone development is performed whereupon a hole pattern is formed.

When it is desired to form a hole pattern via a single exposure using a lattice-like mask, a quadra-pole illumination or cross-pole illumination is used. The contrast may be improved by combining it with X-Y polarized illumination or azimuthally polarized illumination of circular polarization.

In the hole pattern forming process using the resist composition of the invention, when two exposures are involved, these exposures are carried out by changing the illumination and mask for the second exposure from those for the first exposure, whereby a fine size pattern can be formed at the highest contrast and to dimensional uniformity. The masks used in the first and second exposures bear first and second patterns of intersecting lines whereby a pattern of holes at intersections of lines is formed in the resist film after development. The first and second lines are preferably at right angles although an angle of intersection other than 90° may be employed. The first and second lines may have the same or different size and/or pitch. If a single mask bearing first lines in one area and second lines in a different area is used, it is possible to perform first and second exposures continuously. In this case, however, the maximum area available for exposure is one half. Notably, the continuous exposures lead to a minimized alignment error. Of course, the single exposure provides a smaller alignment error than the two continuous exposures.

When two exposures are performed using a single mask without reducing the exposure area, the mask pattern may be a lattice-like pattern, a dot pattern, or a combination of a dot pattern and a lattice-like pattern. The use of a lattice-like pattern contributes to the most improved light contrast, but has the drawback of a reduced resist sensitivity due to a lowering of light intensity. On the other hand, the use of a dot pattern suffers a lowering of light contrast, but provides the merit of an improved resist sensitivity.

Where holes are arrayed in horizontal and vertical directions, the above-described illumination and mask pattern are used. Where holes are arrayed at a different angle, for example, at an angle of 45°, a mask of a 45° arrayed pattern is combined with dipole illumination or cross-pole illumination.

Where two exposures are performed, a first exposure by a combination of dipole illumination with polarized illumination for enhancing the contrast of X-direction lines is followed by a second exposure by a combination of dipole illumination with polarized illumination for enhancing the contrast of Y-direction lines. Two continuous exposures with the X- and Y-direction contrasts emphasized through a single mask can be performed on a currently commercially available scanner.

The method of combining X and Y polarized illuminations with cross-pole illumination using a mask bearing a lattice-like pattern can form a hole pattern through a single exposure, despite a slight lowering of light contrast as compared with two exposures of dipole illumination. The method is estimated to attain a substantial improvement in throughput and avoids the problem of misalignment between two exposures. Using such a mask and illumination, a hole pattern of the order of 40 nm can be formed at a practically acceptable cost.

On use of a mask bearing a lattice-like pattern, light is fully shielded at intersections between gratings. A fine hole pattern may be formed by performing exposure through a mask bearing such a pattern and organic solvent development entailing positive/negative reversal.

On use of a mask bearing a dot pattern, although the contrast of an optical image is low as compared with the lattice-like pattern mask, the formation of a hole pattern is possible owing to the presence of black or light shielded spots.

It is difficult to form a fine hole pattern that holes are randomly arrayed at varying pitch and position. The super-resolution technology using off-axis illumination (such as dipole or cross-pole illumination) in combination with a phase shift mask and polarization is successful in improving the contrast of dense (or grouped) patterns, but not so the contrast of isolated patterns.

When the super-resolution technology is applied to repeating dense patterns, the pattern density bias between dense and isolated patterns, known as proximity bias, becomes a problem. As the super-resolution technology used becomes stronger, the resolution of a dense pattern is more improved, but the resolution of an isolated pattern remains unchanged. Then the proximity bias is exaggerated. In particular, an increase of proximity bias in a hole pattern resulting from further miniaturization poses a serious problem. One common approach taken to suppress the proximity bias is by biasing the size of a mask pattern. Since the proximity bias varies with properties of a photoresist composition, specifically dissolution contrast and acid diffusion, the proximity bias of a mask varies with the type of photoresist composition. For a particular type of photoresist composition, a mask having a different proximity bias must be used. This adds to the burden of mask manufacturing. Then the pack and unpack (PAU) method is proposed in Proc. SPIE Vol. 5753, p 171 (2005), which involves strong super-resolution illumination of a first positive resist to resolve a dense hole pattern, coating the first positive resist pattern with a negative resist film material in alcohol solvent which does not dissolve the first positive resist pattern, exposure and development of an unnecessary hole portion to close the corresponding holes, thereby forming both a dense pattern and an isolated pattern. One problem of the PAU method is misalignment between first and second exposures, as the authors point out in the report. The hole pattern which is not closed by the second development experiences two developments and thus undergoes a size change, which is another problem.

To form a random pitch hole pattern by organic solvent development entailing positive/negative reversal, a mask is used in which a lattice-like pattern is arrayed over the entire surface and the width of gratings is thickened only where holes are to be formed as described in JP-A 2011-170316, paragraph [0102].

Also useful is a mask in which a lattice-like pattern is arrayed over the entire surface and thick dots are disposed only where holes are to be formed.

On use of a mask bearing no lattice-like pattern arrayed, holes are difficult to form, or even if holes are formed, a variation of mask size is largely reflected by a variation of hole size because the optical image has a low contrast.

EXAMPLE

Examples of the invention are given below by way of illustration and not by way of limitation. The abbreviation "pbw" is parts by weight. For all polymers, Mw and Mn are determined by GPC versus polystyrene standards using tetrahydrofuran solvent. For measurement of the hole size of a pattern, a top-down scanning electron microscope (TDSEM) CG-4000 (Hitachi High-Technologies Corp.) was used.

Synthesis Example 1

Synthesis of Monomers

Monomers within the scope of the invention and intermediates therefor were synthesized according to the following formulation.

Synthesis Example 1-1

Synthesis of methyl 4-tert-butylcyclohexanecarboxylate

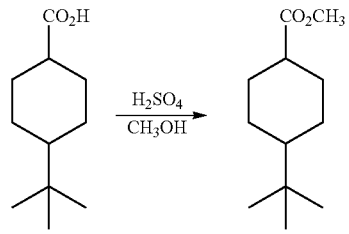

In 630 g of methanol was dissolved 203 g of 4-tert-butylcyclohexanecarboxylic acid. The solution was combined with 0.54 g of conc. sulfuric acid and heated under reflux for 72 hours. The reaction solution was allowed to cool to room temperature, 18 g of 2.5 wt % sodium hydroxide/methanol mixture was added, and the solvent was distilled off in vacuum from the reaction solution. The crude oil was purified by vacuum distillation, obtaining 207 g of methyl 4-tert-butylcyclohexanecarboxylate as colorless liquid (yield 95%, isomer ratio 76:24).

Boiling point: 106° C./1500 Pa $^1$H-HMR (600 MHz in DMSO-$d_6$, for only major isomer): δ=0.78 (9H, s), 0.92-1.05 (3H, m, overlap with minor isomer 3H), 1.36-1.45 (2H, m), 1.53-1.60 (2H, m), 2.05-2.11 (2H, m), 2.63 (1H, m), 3.59 (1H, s) ppm IR (D-ATR): ν=2948, 2854, 1737, 1479, 1451, 1434, 1394, 1365, 1303, 1199, 1172, 1148, 1043, 1010, 988, 888, 842, 823, 782 cm$^{-1}$ Synthesis Example 1-2

Synthesis of Alcohol 1

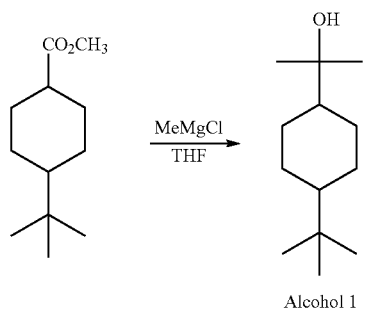

In a nitrogen atmosphere, 202 g of methyl 4-tert-butylcyclohexanecarboxylate from Synthesis Example 1-1 was dissolved in 400 g of tetrahydrofuran. To the solution below 40° C., 1,032 g of methylmagnesium chloride/tetrahydrofuran solution (concentration 337 g/mol) was added dropwise. The reaction solution was ripened at room temperature for 12 hours, followed by ordinary aqueous work-up and vacuum distillation of the solvent. There was obtained 170 g of Alcohol 1. Since Alcohol 1 as post-treated had a fully high purity, it was ready for use in the subsequent step without further purification (white solid).

Synthesis Example 1-3

Synthesis of Monomer 1

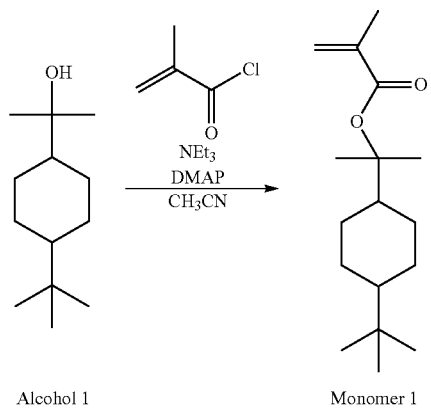

In a nitrogen atmosphere, 165 g of Alcohol 1 from Synthesis Example 1-2, 152 g of triethylamine, and 10 g of 4-(N,N-dimethylamino)pyridine were dissolved in 400 g of acetonitrile. To the solution at 50° C., 122 g of methacryloyl chloride was added dropwise. The reaction solution was ripened at 50° C. for 12 hours, cooled, and added dropwise to 200 g of ice-cooled water to quench the reaction. This was followed by ordinary aqueous work-up and solvent distillation. The crude oil was purified by vacuum distillation, obtaining 200 g of Monomer 1 as colorless liquid (yield 90%, isomer ratio 76:24).

Boiling point: 92° C./20 Pa $^1$H-HMR (600 MHz in DMSO-$d_6$, for only major isomer): δ=0.82 (9H, s), 0.93 (1H, m), 1.19 (1H, m), 1.30-1.50 (12H, m), 1.70-1.80 (1H, m, overlap with minor isomer 1H), 1.82 (3H, s), 1.95 (1H, m), 1.81 (3H, s), 1.94-2.00 (4H, m), 2.10 (2H, s), 2.22 (2H, m), 5.55 (1H, m), 5.90 (1H, m) ppm IR (D-ATR): ν=2946, 2868, 1713, 1638, 1453, 1384, 1365, 1330, 1304, 1245, 1171, 1136, 1007, 935, 613, 655 cm$^{-1}$ Synthesis Example 1-4

Synthesis of Alcohol 2

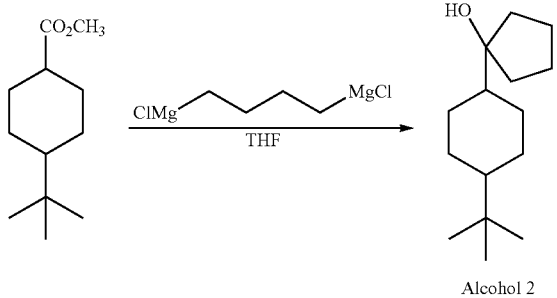

Alcohol 2

Alcohol 2 was synthesized by the same procedure as Synthesis Example 1-2 except, that the Grignard reagent shown above was used instead of methylmagnesium chloride. Since Alcohol 2 as post-treated had a fully high purity, it was ready for use in the subsequent step without further purification (white solid).

Synthesis Example 1-5

Synthesis of Monomer 2

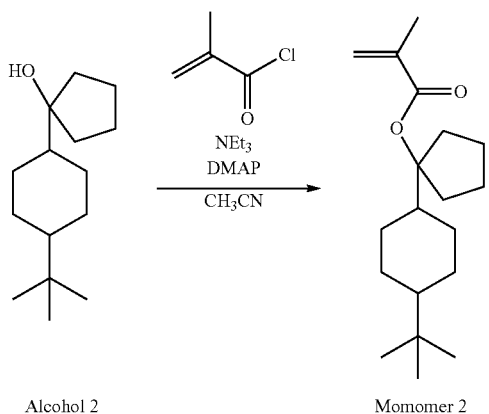

Alcohol 2      Momomer 2

In a nitrogen atmosphere, 133 g of Alcohol 2 from Synthesis Example 1-4, 120 g of triethylamine, and 7 g of 4-(N,N-dimethylamino)pyridine were dissolved in 300 g of acetonitrile. To the solution at 50° C., 93 g of methacryloyl chloride was added dropwise. The reaction solution was ripened at 50° C. for 12 hours, cooled, and added dropwise to 200 g of ice-cooled water to quench the reaction. This was followed by ordinary aqueous work-up and solvent distillation. The crude crystal was recrystallized from a methanol/water mixture, obtaining 153 g of Monomer 2 as white crystal (yield 88%, isomer ratio 76:24).

$^1$H-NMR (600 MHz in DMSO-$d_6$, for only major isomer): δ=0.80 (9H, s), 0.91 (1H, m), 1.14 (1H, m), 1.25-1.35 (2H, m), 1.35-1.50 (4H, m), 1.50-1.60 (2H, m), 1.60-1.80 (5H, ms), 1.82 (3H, m), 2.00-2.06 (2H, m), 2.49 (1H, m), 5.52 (1H, m), 5.90 (1H, s) ppm IR (D-ATR): ν=2954, 2866, 1707, 1635, 1449, 1392, 1363, 1332, 1304, 1242, 1195, 1163, 1007, 970, 935, 845, 817, 658, 576 cm$^{-1}$ Synthesis Example 1-6

Synthesis of Alcohol 3 and Monomer 3

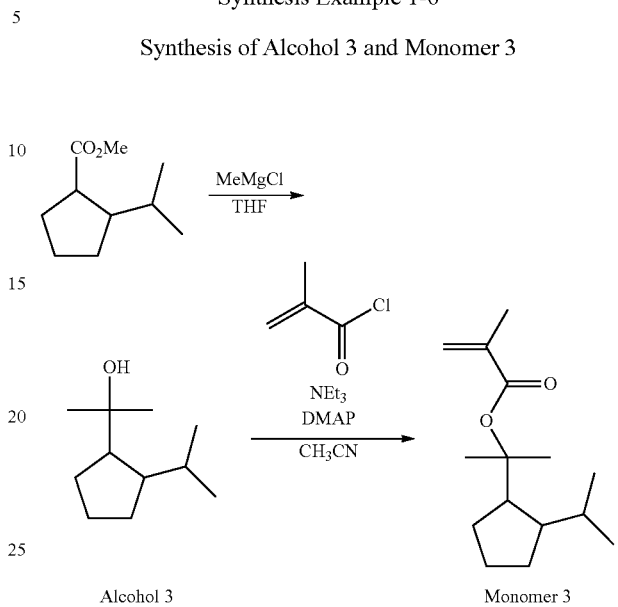

Alcohol 3      Monomer 3

Alcohol 3 was obtained from Grignard reaction by the same procedure as Synthesis Example 1-2 except that methyl 2-isopropylcyclopentanecarboxylate, which was synthesized by a well-known method, was used instead of methyl 4-tert-butylcyclohexanecarboxylate. Without further purification, Alcohol 3 as synthesized was used in the methacryloyl reaction by the same procedure as Synthesis Example 1-3, obtaining Monomer 3.

Synthesis Example 2

Synthesis of Resist Polymers

Polymers within the scope of the invention were synthesized according to the following formulation.

Synthesis Example 2-1

Synthesis of Polymer 1

In a nitrogen atmosphere, 23.2 g of Monomer 1, 19.0 g of 4,8-dioxatricyclo[4.2.1.0$^{3,7}$]nonan-5-on-2-yl methacrylate, 5.0 g of 3-hydroxyadamantyl methacrylate, and 2.4 g of dimethyl 2,2'-azobisisobutyrate were dissolved in 105 g of methyl ethyl ketone. In the nitrogen atmosphere, the solution was added dropwise to 35 g of methyl ethyl ketone being stirred at 80° C., over 4 hours. At the end of dropwise addition, the polymerization solution was kept stirred for 2 hours at 80° C., cooled to room temperature, and added dropwise to 960 g of methanol where a solid precipitated. The solid precipitate was filtered, washed with 360 g of methanol, and vacuum dried at 60° C. for 20 hours, obtaining a polymer in white powder solid form, designated Resist Polymer 1. Weight 48.0 g, yield 92%.

Synthesis Example 2-2

Resist Polymers 2 to 13, Blend Resist Polymers 1, 2 and Comparative Resist Polymers 1 to 8 were synthesized by the same procedure as Synthesis Example 2-1 except that the type and proportion of monomers were changed. The structure of these polymers is identified below.

Resist Polymer 1
Mw=8,500
Resist Polymer 2
Mw=8,900
Resist Polymer 3
Mw=8,600
Resist Polymer 4
Mw=9,000
Resist Polymer 5
Mw=5,300
Resist Polymer 6
Mw=8,300
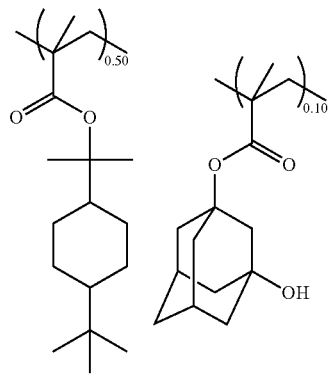
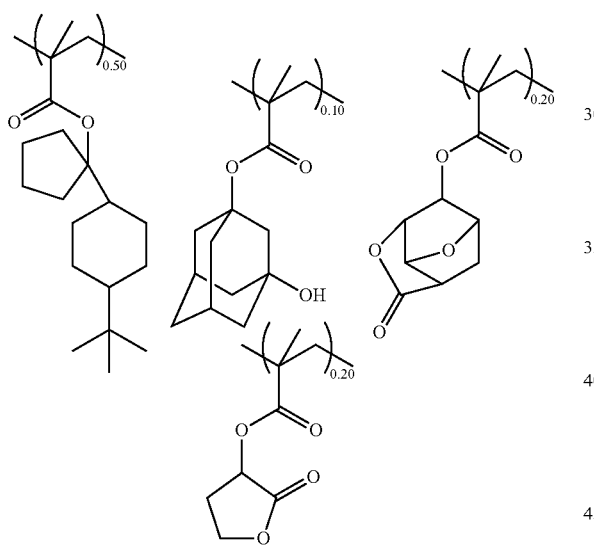
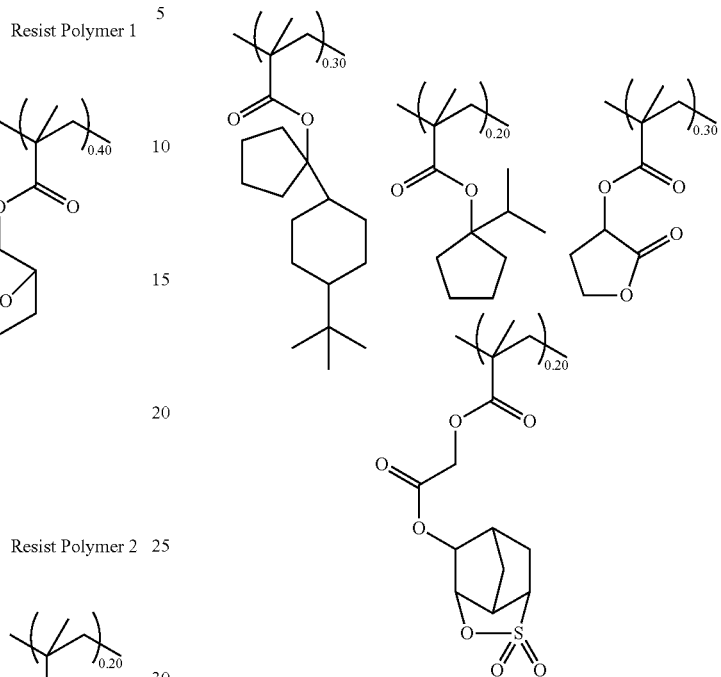
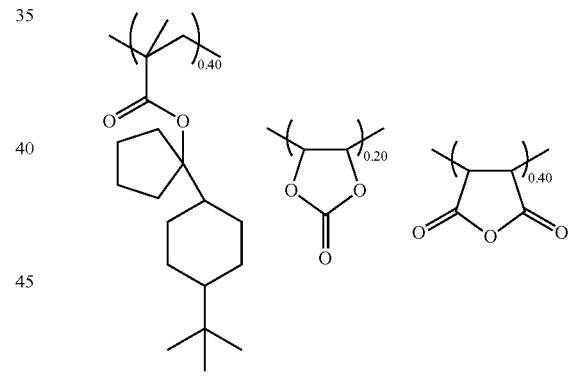
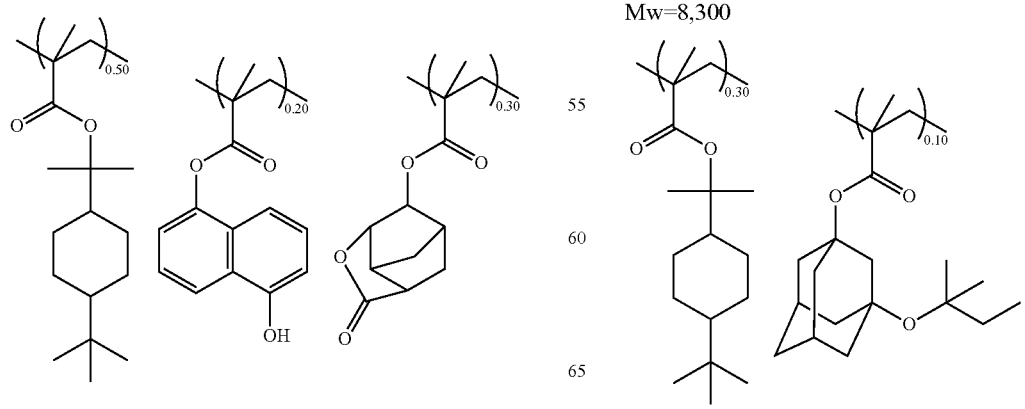

Resist Polymer 7
Mw=8,600
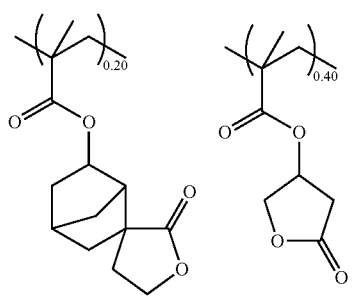
Resist Polymer 8
Mw=8,000
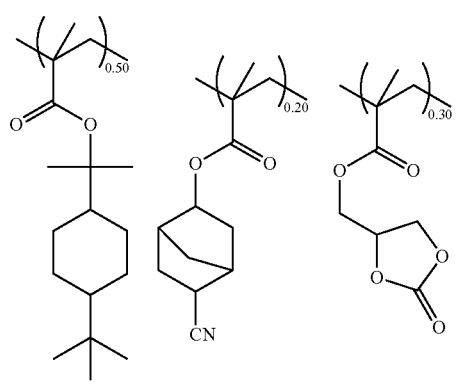
Resist Polymer 9
Mw=7,900
Resist Polymer 9
Resist Polymer 7
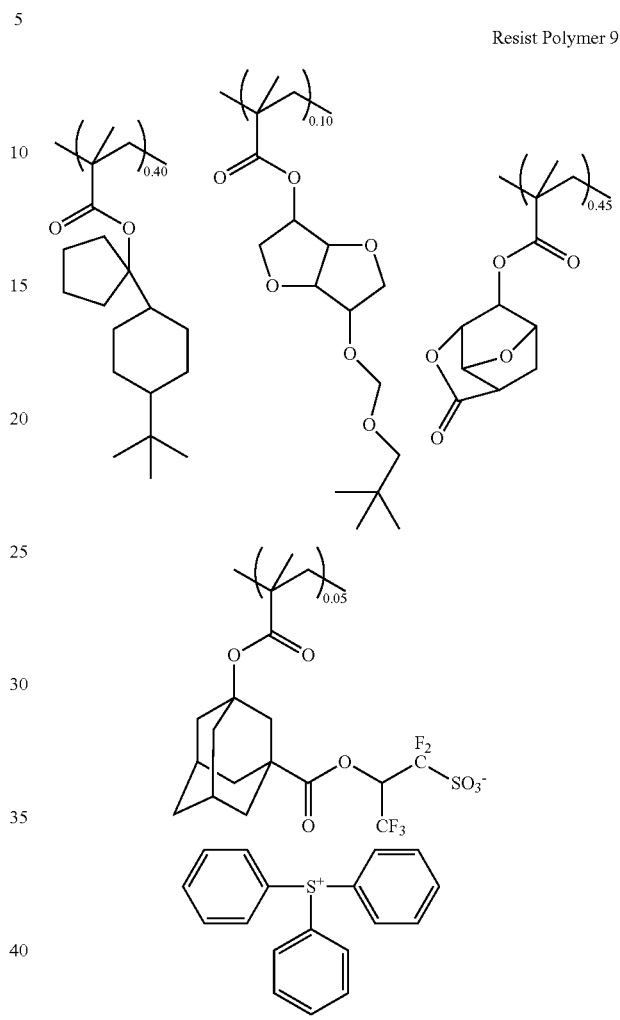
Resist Polymer 10
Mw=7,900
Resist Polymer 8
Resist Polymer 10
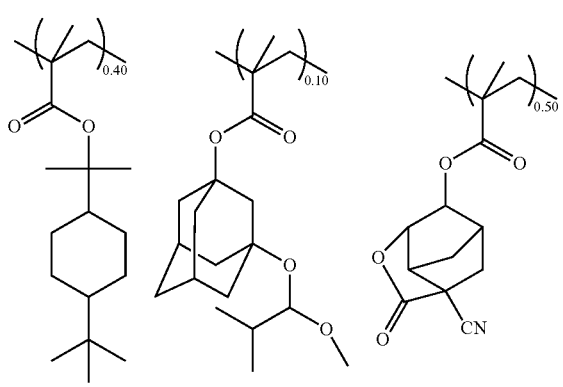
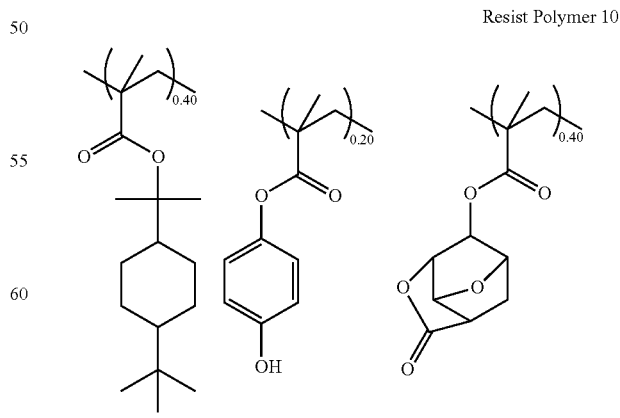

Resist Polymer 11
Mw=8,500
Resist Polymer 11
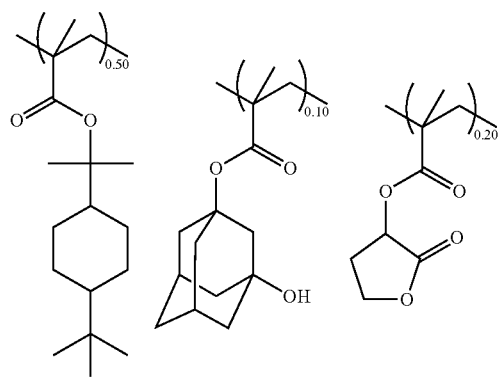
Resist Polymer 12
Mw=8,500
Resist Polymer 12
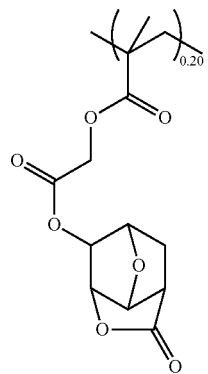
-continued
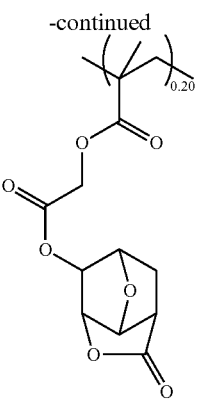
Resist Polymer 13
Mw=8,700
Resist Polymer 13
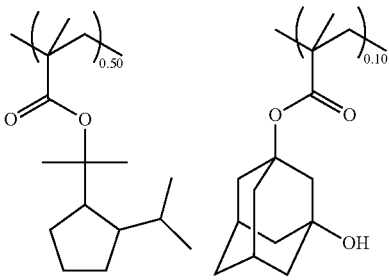
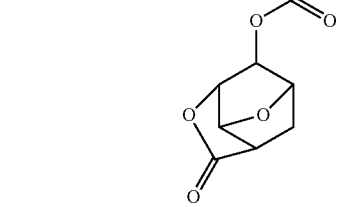
Blend Resist Polymer 1
Mw=6,700
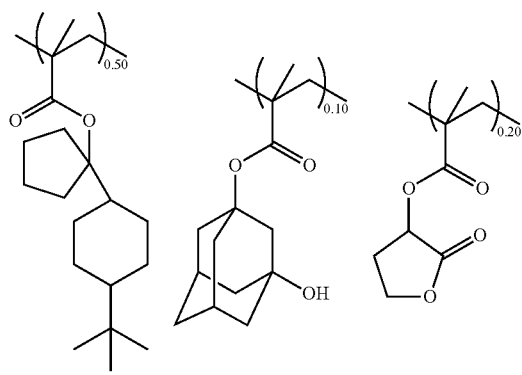
Blend Resist Polymer 1
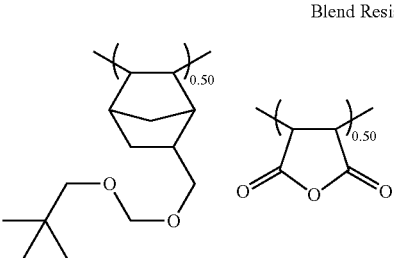

Blend Resist Polymer 2
Mw=21,700

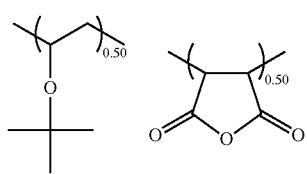

Blend Resist Polymer 2

Comparative Resist Polymer 1
Mw=7,900

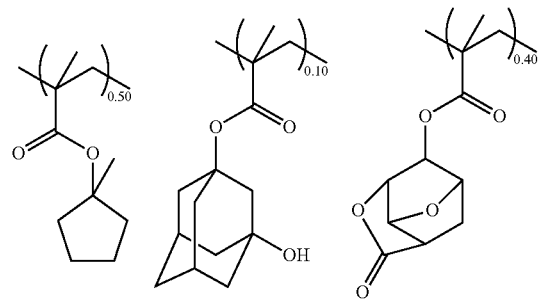

Comparative Resist Polymer 1

Comparative Resist Polymer 2
Mw=8,100

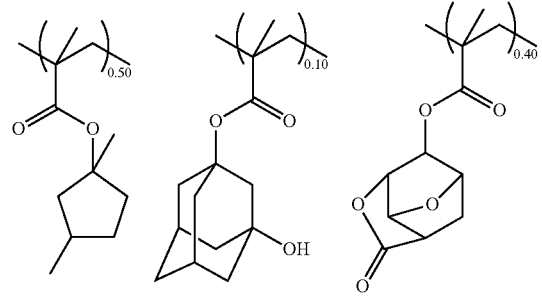

Comparative Resist Polymer 2

Comparative Resist Polymer 3
Mw=8,100

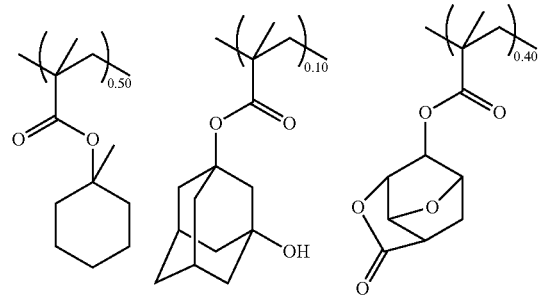

Comparative Resist Polymer 3

Comparative Resist Polymer 4
Mw=8,200

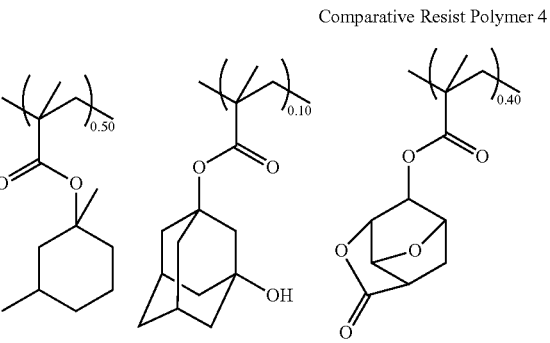

Comparative Resist Polymer 4

Comparative Resist Polymer 5
Mw=8,200

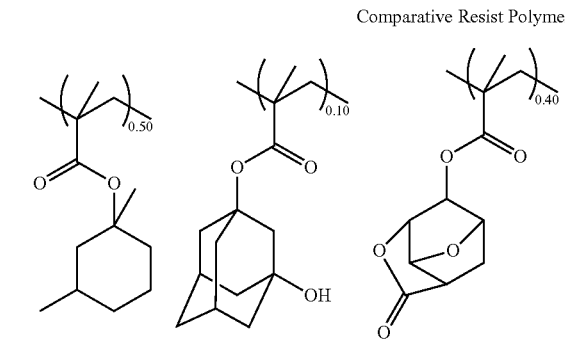

Comparative Resist Polymer 5

Comparative Resist Polymer 6
Mw=8,600

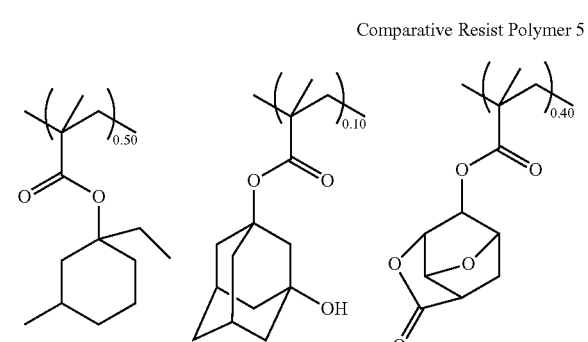

Comparative Resist Polymer 6

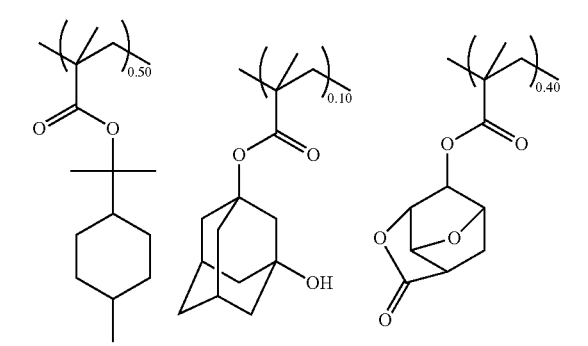

Comparative Resist Polymer 7
 Mw=9,300

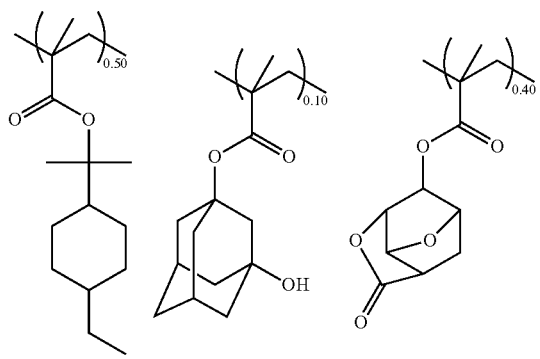

Comparative Resist Polymer 7

Comparative Resist Polymer 8
 Mw=9,300

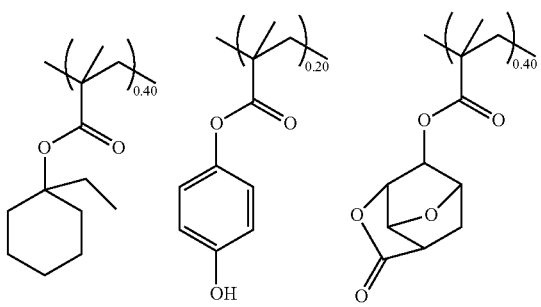

Comparative Resist Polymer 8

Preparation of Resist Composition

Resist compositions in solution form were prepared by dissolving a polymer (identified above) and components in solvents in accordance with the formulation of Table 1 and filtering through a Teflon® filter with a pore size of 0.2 μm. The photoacid generator, water-repellent polymer, quencher, and solvent used herein are identified below.

Acid Generator:

PAG1 to PAG6 of the following structural formulae

PAG 1

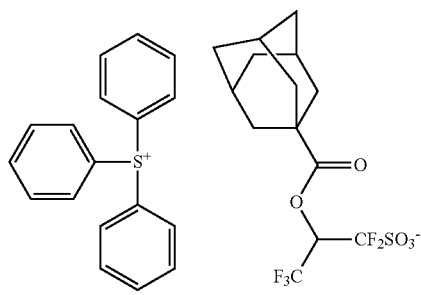

PAG 2

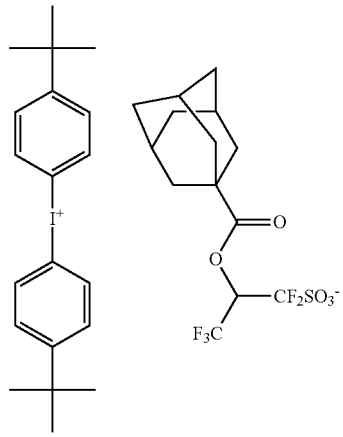

PAG 3

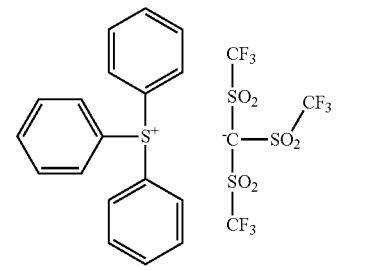

PAG 4

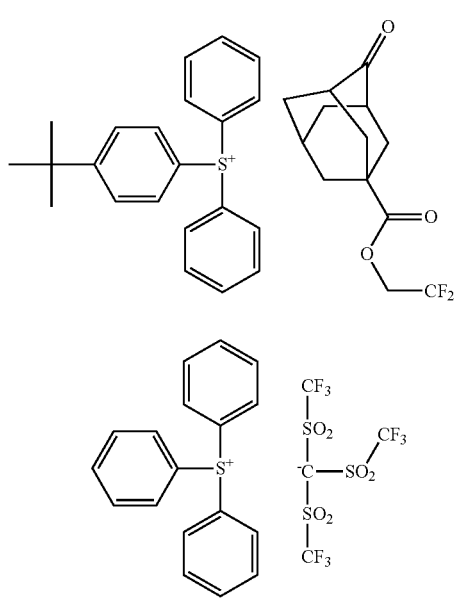

PAG 5

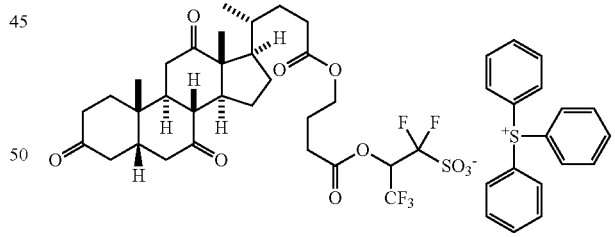

PAG 6

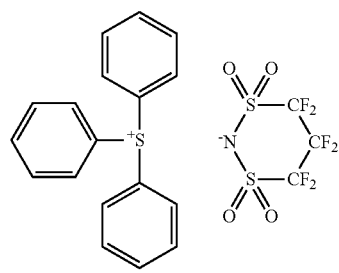

Water-Repellent Polymer 1
Mw=7,500

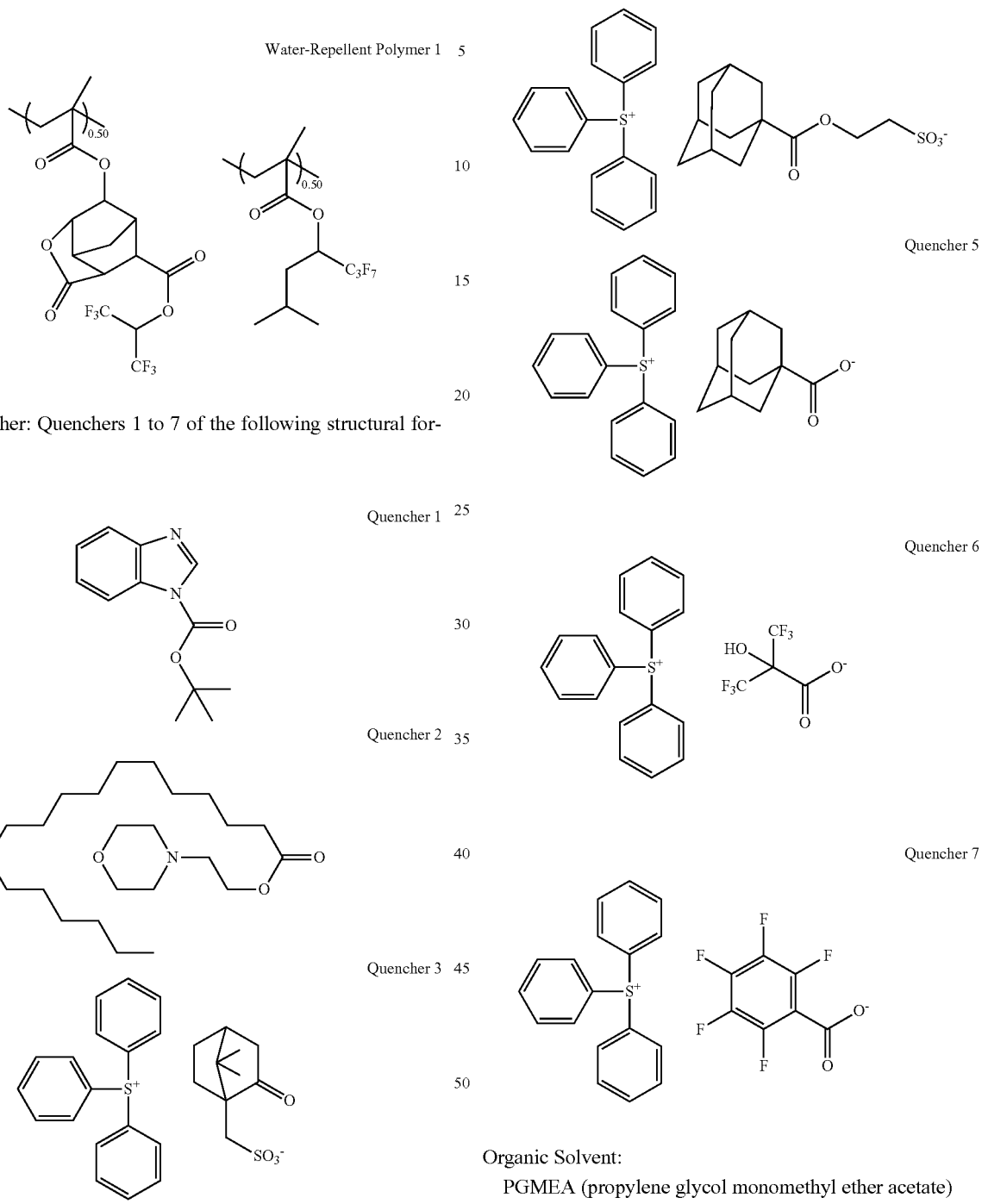

Quencher: Quenchers 1 to 7 of the following structural formulae

Organic Solvent:
PGMEA (propylene glycol monomethyl ether acetate)
CyH (cyclohexanone)

TABLE 1

|  |  | Polymer (pbw) | PAG (pbw) | Basic compound (pbw) | Additive (pbw) | Solvent (pbw) |
|---|---|---|---|---|---|---|
| Resist | 1 | Resist Polymer 1 (100) | PAG1 (5.0) | Quencher 1 (2.00) | — | PGMEA(2,000) CyH(500) |
|  | 2 | Resist Polymer 2 (100) | PAG1 (5.0) | Quencher 2 (2.00) | Water-Repellent Polymer 1 (3) | PGMEA(2,000) CyH(500) |
|  | 3 | Resist Polymer 3 (100) | PAG1 (4.0) | Quencher 3 (4.00) | Water-Repellent Polymer 1 (3) | PGMEA(2,000) CyH(500) |

TABLE 1-continued

|   | | Polymer (pbw) | PAG (pbw) | Basic compound (pbw) | Additive (pbw) | Solvent (pbw) |
|---|---|---|---|---|---|---|
| | 4 | Resist Polymer 4 (100) | PAG2 (5.0) | Quencher 1 (2.00) | Water-Repellent Polymer 1 (3) | PGMEA(2,000) CyH(500) |
| | 5 | Resist Polymer 5 (100) | PAG3 (5.0) | Quencher 1 (2.00) | Water-Repellent Polymer 1 (3) | PGMEA(2,000) CyH(500) |
| | 6 | Resist Polymer 6 (100) | PAG4 (4.0) | Quencher 3 (4.00) | Water-Repellent Polymer 1 (3) | PGMEA(2,000) CyH(500) |
| | 7 | Resist Polymer 7 (100) | PAG4 (4.0) | Quencher 4 (4.00) | Water-Repellent Polymer 1 (3) | PGMEA(2,000) CyH(500) |
| | 8 | Resist Polymer 8 (100) | PAG5 (5.5) | Quencher 5 (4.00) | Water-Repellent Polymer 1 (3) | PGMEA(2,000) CyH(500) |
| | 9 | Resist Polymer 9 (100) | — | Quencher 2 (2.00) | Water-Repellent Polymer 1 (3) | PGMEA(2,000) CyH(500) |
| | 10 | Resist Polymer 1 (60) Comparative Resist Polymer 1 (40) | PAG1 (5.0) | Quencher 1 (2.00) | Water-Repellent Polymer 1 (3) | PGMEA(2,000) CyH(500) |
| | 11 | Resist Polymer 1 (60) Blend Resist Polymer 1 (40) | PAG6 (4.0) | Quencher 6 (4.00) | Water-Repellent Polymer 1 (3) | PGMEA(2,000) CyH(500) |
| | 12 | Resist Polymer 1 (60) Blend Resist Polymer 2 (40) | PAG6 (4.0) | Quencher 7 (4.00) | Water-Repellent Polymer 1 (3) | PGMEA(2,000) CyH(500) |
| | 13 | Resist Polymer 10 (100) | PAG1 (15.0) | Quencher 1 (1.50) | — | PGMEA(2,000) CyH(500) |
| | 14 | Resist Polymer 11 (100) | PAG1 (5.0) | Quencher 1 (2.00) | Water-Repellent Polymer 1 (3) | PGMEA(2,000) CyH(500) |
| | 15 | Resist Polymer 12 (100) | PAG1 (5.0) | Quencher 1 (2.00) | Water-Repellent Polymer 1 (3) | PGMEA(2,000) CyH(500) |
| | 16 | Resist Polymer 13 (100) | PAG1 (5.0) | Quencher 1 (2.00) | Water-Repellent Polymer 1 (3) | PGMEA(2,000) CyH(500) |
| Comparative Resist | 1 | Comparative Resist Polymer 1 (100) | PAG1 (5.0) | Quencher 1 (2.00) | Water-Repellent Polymer 1 (3) | PGMEA(2,000) CyH(500) |
| | 2 | Comparative Resist Polymer 2 (100) | PAG1 (5.0) | Quencher 1 (2.00) | Water-Repellent Polymer 1 (3) | PGMEA(2,000) CyH(500) |
| | 3 | Comparative Resist Polymer 3 (100) | PAG1 (5.0) | Quencher 1 (2.00) | Water-Repellent Polymer 1 (3) | PGMEA(2,000) CyH(500) |
| | 4 | Comparative Resist Polymer 4 (100) | PAG1 (5.0) | Quencher 1 (2.00) | Water-Repellent Polymer 1 (3) | PGMEA(2,000) CyH(500) |
| | 5 | Comparative Resist Polymer 5 (100) | PAG1 (5.0) | Quencher 1 (2.00) | Water-Repellent Polymer 1 (3) | PGMEA(2,000) CyH(500) |
| | 6 | Comparative Resist Polymer 6 (100) | PAG1 (5.0) | Quencher 1 (2.00) | Water-Repellent Polymer 1 (3) | PGMEA(2,000) CyH(500) |
| | 7 | Comparative Resist Polymer 7 (100) | PAG1 (5.0) | Quencher 1 (2.00) | Water-Repellent Polymer 1 (3) | PGMEA(2,000) CyH(500) |
| | 8 | Comparative Resist Polymer 8 (100) | PAG1 (15.0) | Quencher 1 (1.50) | — | PGMEA(2,000) CyH(500) |

Examples 1-1 to 1-18 and Comparative Examples 1-1 to 1-7

ArF Lithography Patterning Test 1

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition shown in Table 1 was spin coated, then baked on a hot plate at 100° C. for 60 seconds to form a resist film of 100 nm thick.

Using an ArF excimer laser immersion lithography scanner NSR-610C (Nikon Corp., NA 1.30, σ 0.98/0.78, cross-pole opening 20 deg., azimuthally polarized illumination), exposure was performed in a varying dose through a 6% halftone phase shift, mask bearing a lattice-like pattern with a pitch of 90 nm and a line width of 30 nm (on-wafer size). After the exposure, the wafer was baked (PEB) at the temperature shown in Table 2 for 60 seconds and developed. Specifically, butyl acetate was injected from a development nozzle while the wafer was spun at 30 rpm for 3 seconds, which was followed by stationary puddle development for 27 seconds. The wafer was rinsed with diisoamyl ether, spin dried, and baked at 100° C. for 20 seconds to evaporate off the rinse liquid, yielding a negative pattern.

A hole pattern resulted from image reversal by solvent development. By observation under TDSEM CG-4000, the size of 50 holes was measured, from which a size variation 3σ was determined. The cross-sectional profile of the hole pattern was observed under electron microscope S-4300 (Hitachi High Technologies Corp.). The results are shown in Table 2.

TABLE 2

| | | Resist | PEB temp. (° C.) | Dose (mJ/cm²) | Developer | Pattern profile | Hole size variation 3σ (nm) |
|---|---|---|---|---|---|---|---|
| Example | 1-1 | Resist 1 | 95 | 34 | n-butyl acetate | perpendicular | 2.2 |
| | 1-2 | Resist 2 | 90 | 36 | n-butyl acetate | perpendicular | 2.3 |
| | 1-3 | Resist 3 | 95 | 27 | n-butyl acetate | perpendicular | 2.2 |
| | 1-4 | Resist 4 | 90 | 27 | n-butyl acetate | perpendicular | 2.2 |
| | 1-5 | Resist 5 | 95 | 26 | n-butyl acetate | perpendicular | 2.4 |
| | 1-6 | Resist 6 | 90 | 27 | n-butyl acetate | perpendicular | 2.5 |
| | 1-7 | Resist 7 | 95 | 29 | n-butyl acetate | perpendicular | 2.4 |
| | 1-8 | Resist 8 | 90 | 25 | n-butyl acetate | perpendicular | 2.3 |
| | 1-9 | Resist 9 | 95 | 23 | n-butyl acetate | perpendicular | 2.5 |
| | 1-10 | Resist 10 | 95 | 28 | n-butyl acetate | perpendicular | 2.3 |
| | 1-11 | Resist 11 | 95 | 26 | n-butyl acetate | perpendicular | 2.3 |
| | 1-12 | Resist 12 | 95 | 23 | n-butyl acetate | perpendicular | 2.4 |
| | 1-13 | Resist 3 | 95 | 31 | 2-heptanone | perpendicular | 2.4 |
| | 1-14 | Resist 3 | 95 | 38 | methyl benzoate | perpendicular | 2.3 |
| | 1-15 | Resist 3 | 95 | 39 | ethyl benzoate | perpendicular | 2.4 |
| | 1-16 | Resist 14 | 95 | 29 | n-butyl acetate | perpendicular | 4.0 |
| | 1-17 | Resist 15 | 95 | 31 | n-butyl acetate | perpendicular | 3.8 |
| | 1-18 | Resist 16 | 95 | 30 | n-butyl acetate | perpendicular | 2.5 |
| Comparative Example | 1-1 | Comparative Resist 1 | 95 | 41 | n-butyl acetate | inversely tapered | 4.0 |
| | 1-2 | Comparative Resist 2 | 95 | 40 | n-butyl acetate | inversely tapered | 3.8 |
| | 1-3 | Comparative Resist 3 | 95 | 38 | n-butyl acetate | inversely tapered | 3.7 |
| | 1-4 | Comparative Resist 4 | 95 | 38 | n-butyl acetate | inversely tapered | 3.6 |
| | 1-5 | Comparative Resist 5 | 95 | 37 | n-butyl acetate | inversely tapered | 3.5 |
| | 1-6 | Comparative Resist 6 | 95 | 36 | n-butyl acetate | inversely tapered | 3.2 |
| | 1-7 | Comparative Resist 7 | 110 | 30 | n-butyl acetate | inversely tapered | 5.5 |

Examples 2-1 to 2-15 and Comparative Examples 2-1 to 2-7

ArF Lithography Patterning Test 2

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition shown in Table 1 was spin coated, then baked on a hot plate at 100° C. for 60 seconds to form a resist film of 80 nm thick.

Using an ArF excimer laser immersion lithography scanner NSR-610C (Nikon Corp., NA 1.30, σ 0.98/0.78, cross-pole opening 20 deg., azimuthally polarized illumination), exposure was performed in a varying dose through a 6% halftone phase shift, mask bearing a line-and-space pattern with a pitch of 100 nm and a line width of 50 nm (on-wafer size). After the exposure, the wafer was baked (PEB) at the temperature shown in Table 3 for 60 seconds and developed. Specifically, the developer shown in Table 3 was injected from a development nozzle while the wafer was spun at 30 rpm for 3 seconds, which was followed by stationary puddle development for 27 seconds. The wafer was rinsed with 4-methyl-2-pentanol, spin dried, and baked at 100° C. for 20 seconds to evaporate off the rinse liquid, yielding a negative pattern.

A hole pattern resulted from image reversal by solvent development. The size of holes was measured under TDSEM CG-4000. The LWR of those spaces having a size of 50 nm±5 nm was determined. The minimum size of spaces which remained open without bridging when the exposure dose was increased was determined. The results are shown in Table 3.

TABLE 3

| | | Resist | PEB temp. (° C.) | Developer | LWR (nm) | Minimum space size (nm) |
|---|---|---|---|---|---|---|
| Example | 2-1 | Resist 1 | 95 | n-butyl acetate | 4.6 | 40 |
| | 2-2 | Resist 2 | 90 | n-butyl acetate | 4.4 | 37 |
| | 2-3 | Resist 3 | 95 | n-butyl acetate | 4.4 | 38 |
| | 2-4 | Resist 4 | 90 | n-butyl acetate | 4.3 | 37 |
| | 2-5 | Resist 5 | 95 | n-butyl acetate | 4.2 | 37 |
| | 2-6 | Resist 6 | 90 | n-butyl acetate | 4.1 | 38 |
| | 2-7 | Resist 7 | 95 | n-butyl acetate | 4.0 | 37 |
| | 2-8 | Resist 8 | 90 | n-butyl acetate | 4.5 | 34 |
| | 2-9 | Resist 9 | 95 | n-butyl acetate | 4.6 | 35 |
| | 2-10 | Resist 1 | 95 | 2-heptanone | 5.1 | 39 |
| | 2-11 | Resist 1 | 95 | methyl benzoate | 4.5 | 35 |
| | 2-12 | Resist 1 | 95 | ethyl benzoate | 4.6 | 32 |
| | 2-13 | Resist 14 | 95 | n-butyl acetate | 4.2 | 35 |
| | 2-14 | Resist 15 | 95 | n-butyl acetate | 4.3 | 34 |
| | 2-15 | Resist 16 | 95 | n-butyl acetate | 4.2 | 36 |
| Comparative Example | 2-1 | Comparative Resist 1 | 95 | n-butyl acetate | 6.2 | 43 |
| | 2-2 | Comparative Resist 2 | 95 | n-butyl acetate | 6.1 | 42 |
| | 2-3 | Comparative Resist 3 | 95 | n-butyl acetate | 5.7 | 41 |

TABLE 3-continued

| | Resist | PEB temp. (° C.) | Developer | LWR (nm) | Minimum space size (nm) |
|---|---|---|---|---|---|
| 2-4 | Comparative Resist 4 | 95 | n-butyl acetate | 5.7 | 40 |
| 2-5 | Comparative Resist 5 | 95 | n-butyl acetate | 5.6 | 43 |
| 2-6 | Comparative Resist 6 | 95 | n-butyl acetate | 5.5 | 41 |
| 2-7 | Comparative Resist 7 | 110 | n-butyl acetate | 6.9 | 48 |

Examples 3-1 to 3-3 and Comparative Example 3-1

EB Lithography Patterning Test

Using a coater/developer system Clean Track Mark 5 (Tokyo Electron Ltd.), the resist composition was spin coated onto a silicon substrate (diameter 6 inches, vapor primed with hexamethyldisilazane (HMDS)) and pre-baked on a hot plate at 110° C. for 60 seconds to form a resist film of 100 nm thick. Using a system HL-800D (Hitachi Ltd.) at a HV voltage of 50 kV, the resist film was exposed imagewise to EB in a vacuum chamber.

Using Clean Track Mark 5, immediately after the imagewise exposure, the resist film was baked (PEB) on a hot plate at the temperature shown in Table 4 for 60 seconds and puddle developed in the developer shown in Table 4 for 30 seconds. The substrate was rinsed with diisoamyl ether, spin dried, and baked at 100° C. for 20 seconds to evaporate off the rinse liquid, yielding a negative pattern.

Sensitivity is the exposure dose ($\mu C/cm^2$) that provides a 1:1 resolution of a 100-nm line-and-space pattern. Resolution is a minimum size at the exposure dose. The 100-nm L/S pattern was measured for LWR under SEM. The results are shown in Table 4.

TABLE 4

| | Resist | PEB temp. (° C.) | Developer | Sensitivity ($\mu C/cm^2$) | LWR (nm) |
|---|---|---|---|---|---|
| Example | 3-1 Resist 13 | 95 | n-butyl acetate | 56 | 4.8 |
| | 3-2 Resist 13 | 95 | methyl benzoate | 57 | 4.7 |
| | 3-3 Resist 13 | 95 | ethyl benzoate | 59 | 4.9 |
| Comparative Example | 3-1 Comparative Resist 8 | 95 | n-butyl acetate | 52 | 8.6 |

As is evident from the data shown in Tables 2 to 4, the resist compositions within the scope of the invention form patterns of perpendicular profile and improved dimensional uniformity after organic solvent development.

While the invention has been described with reference to a preferred embodiment, it will be understood by those skilled in the art that various changes may be made and equivalents may be substituted for elements thereof without departing from the scope of the invention. Therefore, it is intended that the invention not be limited to the particular embodiment disclosed as the best mode contemplated for carrying out this invention, but that the invention will include all embodiments falling within the scope of the appended claims.

Japanese Patent Application No. 2012-177800 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monomer having the general formula (1):

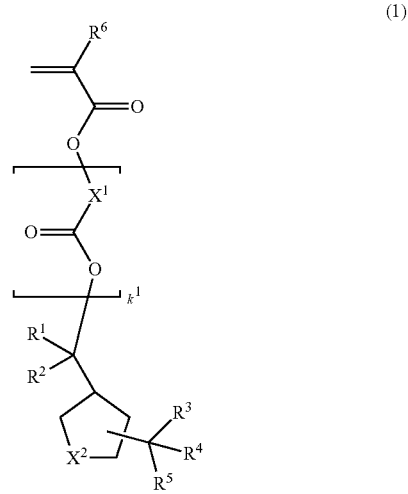

(1)

wherein $R^1$ and $R^2$ are each independently straight, branched or cyclic $C_1$-$C_{10}$ alkyl, $R^1$ and $R^2$ may bond together to form a ring with the carbon atom to which they are attached, $R^3$, $R^4$ and $R^5$ are each independently hydrogen, methyl or ethyl, excluding that at least two of $R^3$, $R^4$ and $R^5$ are hydrogen at the same time, $R^6$ is hydrogen or methyl, $X^1$ is a $C_1$-$C_{10}$ alkylene group which may have an ether radical, ester radical, lactone ring or hydroxyl radical, or $C_6$-$C_{10}$ arylene group, $X^2$ is methylene or ethylene, and $k^1$ is 0 or 1.

2. A polymer comprising recurring units having the general formula (A1):

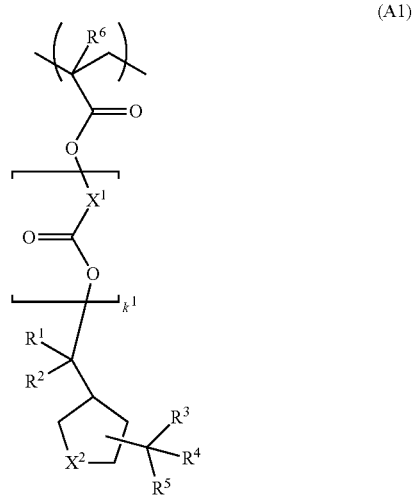

(A1)

wherein $R^1$ and $R^2$ are each independently straight, branched or cyclic $C_1$-$C_{10}$ alkyl, $R^1$ and $R^2$ may bond together to form a ring with the carbon atom to which they are attached, $R^3$, $R^4$ and $R^5$ are each independently hydrogen, methyl or ethyl, excluding that at least two of $R^3$, $R^4$ and $R^5$ are hydrogen at the same time, $R^6$ is hydrogen or methyl, $X^1$ is a $C_1$-$C_{10}$ alkylene group which may have an ether radical, ester radical, lactone ring or hydroxyl radical, or $C_6$-$C_{10}$ arylene group, $X^2$ is methylene or ethylene, and $k^1$ is 0 or 1.

3. A pattern forming process comprising the steps of:

applying a resist composition comprising the polymer of claim 2 and an optional acid generator onto a substrate, prebaking the composition to form a resist film, exposing a selected region of the resist film to high-energy radiation, baking, and developing the exposed film in an organic solvent-based developer to form a negative pattern wherein the unexposed region of resist film is dissolved away and the exposed region of resist film is not dissolved.

4. The process of claim 3 wherein the developer comprises at least one organic solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3 ethoxypropionate, methyl lactate, ethyl lactate, propyl lactate, butyl lactate, isobutyl lactate, amyl lactate, isoamyl lactate, methyl 2-hydroxyisobutyrate, ethyl 2 hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

5. The process of claim 3 wherein the step of exposing the resist film to high-energy radiation includes KrF excimer laser lithography of wavelength 248 nm, ArF excimer laser lithography of wavelength 193 nm, EUV lithography of wavelength 13.5 nm or EB lithography.

6. A pattern forming process according to claim 3, comprising the steps of:

applying a resist composition onto a substrate, the resist composition comprising the polymer, an optional acid generator, and an organic solvent, prebaking the composition to form a resist film, forming a protective film on the resist film, exposing a selected region of the resist film to high-energy radiation, baking, and applying an organic solvent-based developer to dissolve away the protective film and the unexposed region of resist film for forming a negative pattern wherein the exposed region of resist film is not dissolved.

7. A negative pattern-forming resist composition comprising a polymer, an acid generator, and an organic solvent, said polymer comprising recurring units having the general formula (A1):

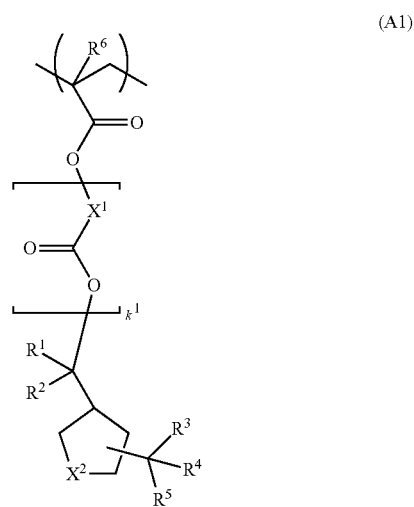

(A1)

wherein $R^1$ and $R^2$ are each independently straight, branched or cyclic $C_1$-$C_{10}$ alkyl, $R^1$ and $R^2$ may bond together to form a ring with the carbon atom to which they are attached, $R^3$, $R^4$ and $R^5$ are each independently hydrogen, methyl or ethyl, excluding that at least two of $R^3$, $R^4$ and $R^5$ are hydrogen at the same time, $R^6$ is hydrogen or methyl, $X^1$ is a $C_1$-$C_{10}$ alkylene group which may have an ether radical, ester radical, lactone ring or hydroxyl radical, or $C_6$-$C_{10}$ arylene group, $X^2$ is methylene or ethylene, and $k^1$ is 0 or 1, said polymer being dissolvable in a developer selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

8. The polymer of claim 2 wherein the recurring units having the general formula (A1) are recurring units derived from a monomer selected from the group consisting of the following formulae:

123
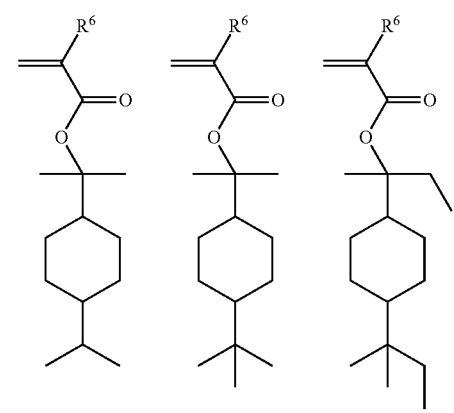
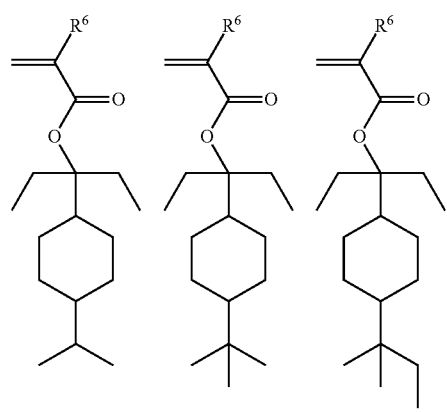
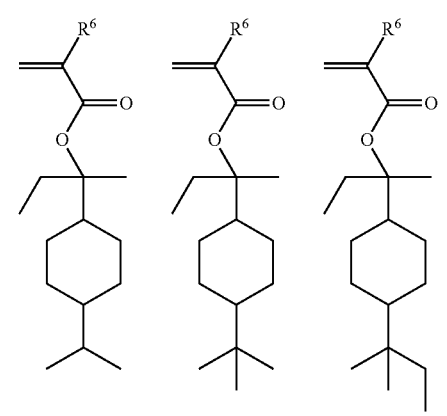
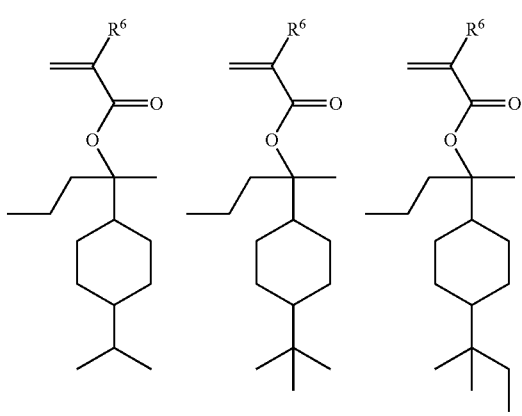
124
-continued
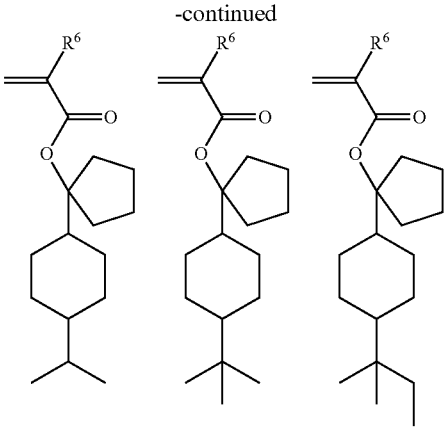
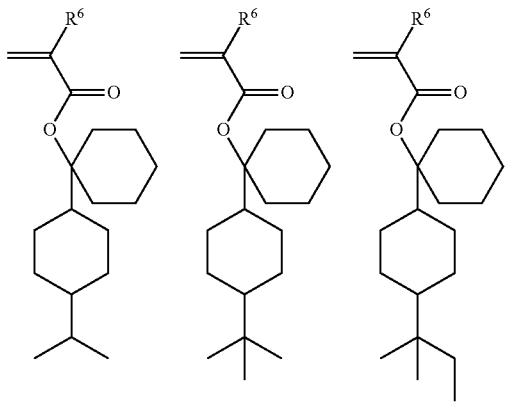
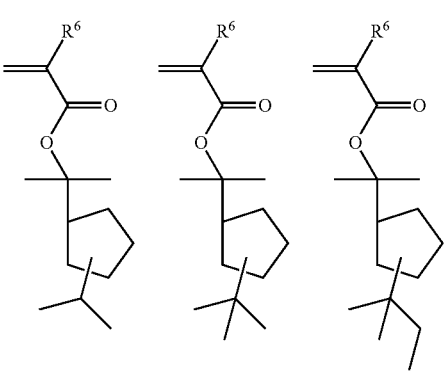
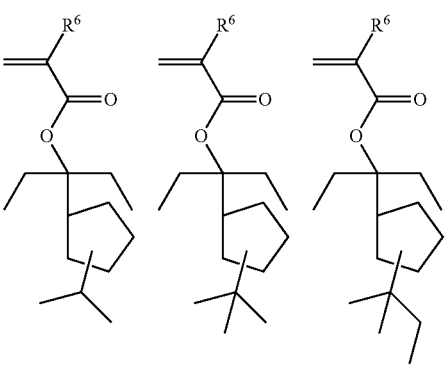

125
-continued
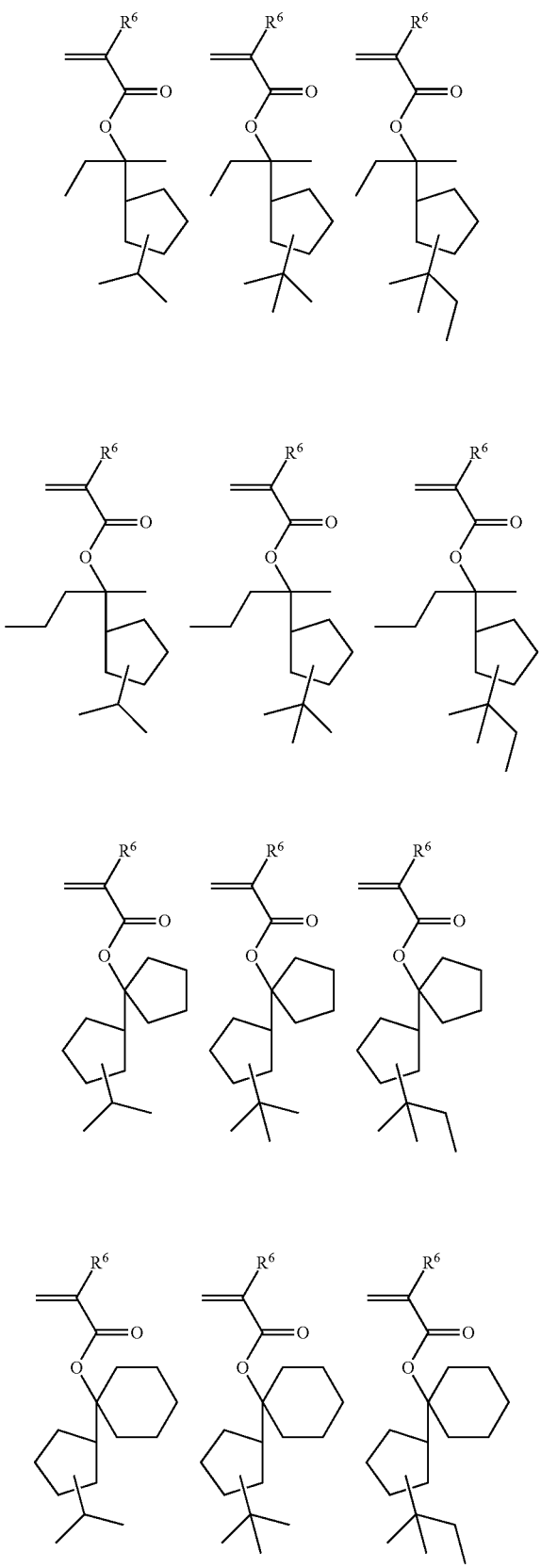
126
-continued
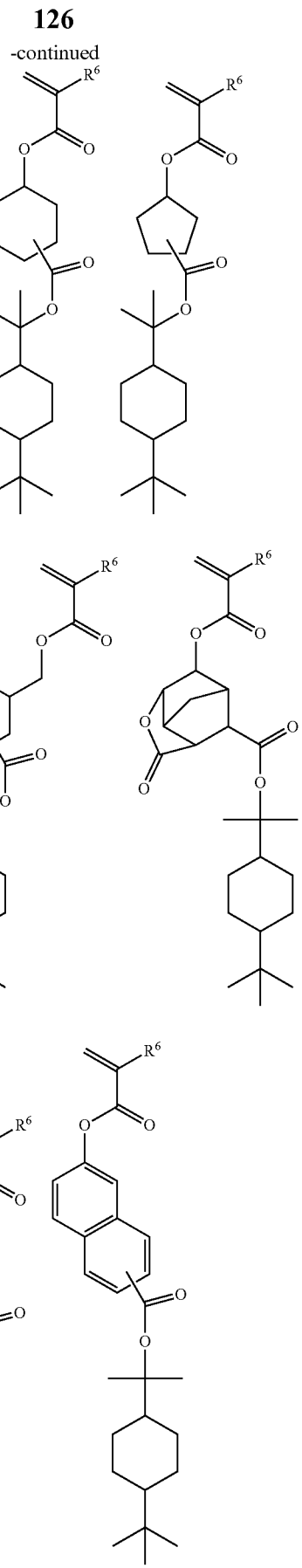

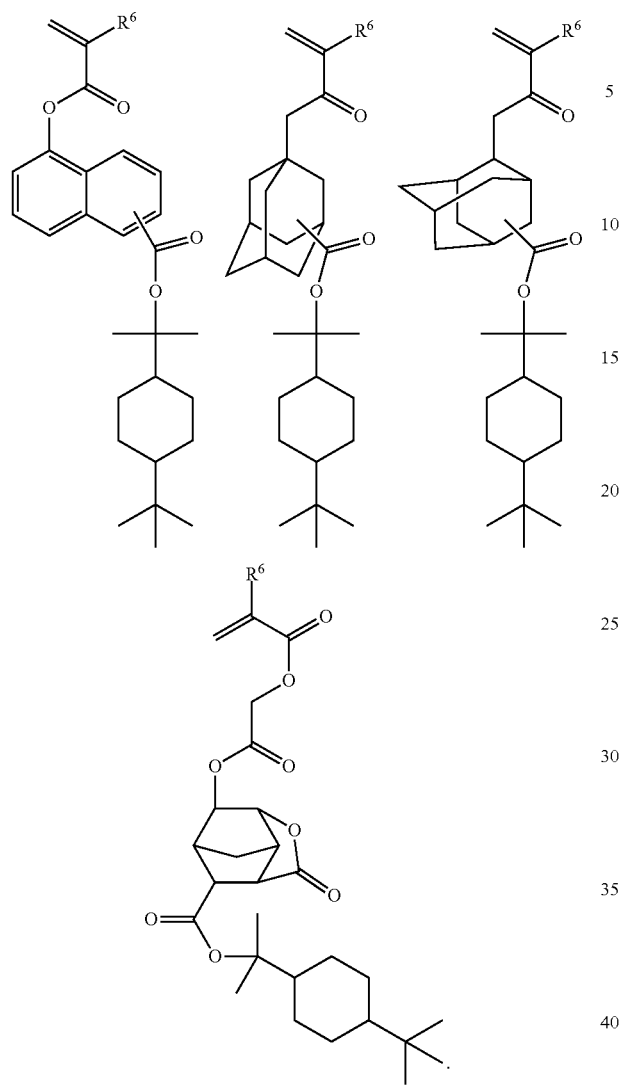

9. The polymer of claim 2 which further comprises recurring units having the following formula (A2):

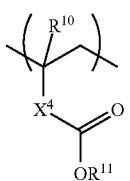

wherein, $R^{10}$ is hydrogen or methyl, $R^{11}$ is an acid labile group, and $X^4$ is a single bond, phenylene, naphthylene, or —C(=O)—O—$R^{12}$— wherein $R^{12}$ is a straight, branched or cyclic $C_1$-$C_{10}$ alkylene group which may contain an ether radical, ester radical, lactone ring or hydroxyl radical, or a phenylene or naphthylene group.

10. The polymer of claim 2 which further comprises recurring units selected from the group consisting of the following general formulae (B1) to (B4):

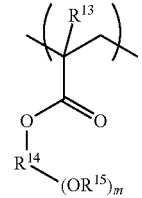

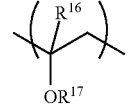

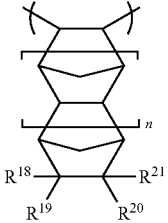

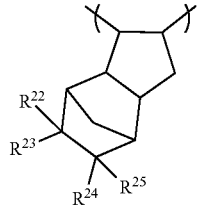

wherein $R^{13}$ and $R^{16}$ are each independently hydrogen or methyl; $R^{14}$ is a di- to pentavalent, straight, branched or cyclic $C_1$-$C_{16}$ aliphatic hydrocarbon group which may contain an ether or ester radical; $R^{15}$ and $R^{17}$ each are an acid labile group; $R^{18}$ to $R^{21}$ and $R^{22}$ to $R^{25}$ are each independently hydrogen, cyano, a straight, branched or cyclic $C_1$-$C_6$ alkyl group, alkoxycarbonyl, or a group having an ether radical or lactone ring, at least one of $R^{18}$ to $R^{21}$ and $R^{22}$ to $R^{25}$ has a hydroxyl group substituted with an acid labile group; m is an integer of 1 to 4, and n is 0 or 1.

11. The polymer of claim 2 which further comprises recurring units (C1) derived from monomers having adhesive groups such as hydroxy, cyano, carbonyl, ester, ether groups, lactone rings, carboxyl, carboxylic anhydride, sulfonic acid ester, disulfone or carbonate groups.

12. The polymer of claim 2 which further comprises recurring units selected from the group consisting of the following general formulae (D1) to (D3):

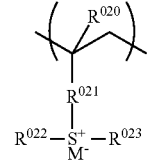

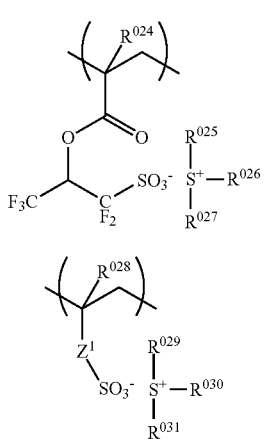

wherein $R^{020}$, $R^{024}$ and $R^{028}$ each are hydrogen or methyl, $R^{021}$ is a single bond, phenylene, —O—$R^{033}$—, or —C(=O)—Y—$R^{033}$— wherein Y is oxygen or NH, and $R^{033}$ is a straight, branched or cyclic $C_1$-$C_6$ alkylene group, alkenylene group or phenylene group, which may contain a carbonyl (—CO—), ester (—COO—), ether (—O—) or hydroxyl radical, $R^{022}$, $R^{023}$, $R^{025}$, $R^{026}$, $R^{027}$, $R^{029}$, $R^{030}$, and $R^{031}$ are each independently a straight, branched or cyclic $C_1$-$C_{12}$ alkyl group which may contain a carbonyl, ester or ether radical, or a $C_6$-$C_{12}$ aryl, $C_7$-$C_{20}$ aralkyl, or thiophenyl group, $Z^1$ is a single bond, methylene, ethylene, phenylene, fluorophenylene, —O—$R^{032}$—, or —C(=O)—$Z^2$—$R^{032}$— wherein $Z^2$ is oxygen or NH, and $R^{032}$ is a straight, branched or cyclic $C_1$-$C_6$ alkylene group, alkenylene group or phenylene group, which may contain a carbonyl, ester, ether or hydroxyl radical, and $M^-$ is a non-nucleophilic counter ion.

* * * * *